(12) United States Patent
Shitara et al.

(10) Patent No.: US 7,666,418 B2
(45) Date of Patent: Feb. 23, 2010

(54) METHOD FOR TREATING TH2-MEDIATED DISEASE

(75) Inventors: Kenya Shitara, Machida (JP); Nobuo Hanai, Machida (JP); Emi Shoji, Machida (JP); Mikiko Sakurada, Machida (JP); Akiko Furuya, Machida (JP); Kazuyasu Nakamura, Machida (JP); Rinpei Niwa, Machida (JP); Kenji Shibata, Machida (JP); Motoo Yamasaki, Machida (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 69 days.

(21) Appl. No.: 11/094,718

(22) Filed: Mar. 31, 2005

(65) Prior Publication Data

US 2005/0187380 A1     Aug. 25, 2005

Related U.S. Application Data

(62) Division of application No. 09/796,744, filed on Mar. 2, 2001, now Pat. No. 6,989,145.

(30) Foreign Application Priority Data

Mar. 3, 2000   (JP)  ............... P.2000-059508
Dec. 28, 2000  (JP)  ............... P.2000-401563

(51) Int. Cl.
  *A61K 39/395*   (2006.01)
  *A61K 39/00*    (2006.01)
(52) U.S. Cl. ............... 424/143.1; 424/130.1; 424/133.1; 424/134.1; 424/141.1
(58) Field of Classification Search ............... None
  See application file for complete search history.

(56) References Cited

U.S. PATENT DOCUMENTS

| | | | |
|---|---|---|---|
| 5,891,996 A | 4/1999 | Mateo de Acosta del Rio et al. | |
| 5,932,703 A | 8/1999 | Godiska et al. | ............ 530/351 |
| 6,150,132 A | 11/2000 | Wells et al. | ................ 435/69.1 |
| 6,245,332 B1 | 6/2001 | Butcher et al. | |
| 6,488,930 B1 | 12/2002 | Wu et al. | ................ 424/143.1 |
| 6,498,015 B1 | 12/2002 | Godiska et al. | ............ 435/7.24 |
| 2002/0019341 A1 | 2/2002 | Butcher et al. | ................ 514/8 |
| 2002/0160015 A1 | 10/2002 | Wells et al. | .............. 424/185.1 |
| 2002/0187930 A1 | 12/2002 | Wells et al. | ................... 514/12 |

FOREIGN PATENT DOCUMENTS

| | | |
|---|---|---|
| WO | WO 96/23068 | 8/1996 |
| WO | WO 97/10354 | 3/1997 |
| WO | WO 99/15666 | 4/1999 |
| WO | WO 99/25380 | 5/1999 |
| WO | WO 00/00219 | 1/2000 |
| WO | WO 00/41724 | 7/2000 |
| WO | WO 00/42074 | 7/2000 |
| WO | WO 00/67791 | 11/2000 |

OTHER PUBLICATIONS

Wells et al. Inflamm. Res. 1999, 48:353-362.*
Chantry et al. Current Drug Targets-Inflammation & Allergy, 2002 1:109-116.*
Power et al., "Molecular Cloning and Functional Expression of a Novel CC Chemokine Receptor . . . ", *J. of Biological Chemistry*, vol. 270, No. 33 (1995), pp. 19495-19500.
Jones, et al., "Expression pattern to T-cell-associated chemokine receptors and their chemokines correlates with . . . ", *Blood*, vol. 96, No. 2 (2000), pp. 685-690.
Mueller, et al., "Enhancement of Antibody-Dependent Cytotoxicity with a Chimeric Anti-GD2/Antibody", *J. of Immunology*, vol. 144, No. 4 (1990), pp. 1382-1386.
Riechman, et al., "Reshaping human antibodies for Therapy", *Nature*, vol. 332 (1988), pp. 323-327.
van den Berg, et al., "High Expression of the CC Chemokine TARC in Reed-Sternberg Cells", *Am. J. of Pathology*, vol. 154, No. 6 (1999), pp. 1685-1691.
D'Ambrosio, et al., "Cutting Edge: Selective Up-Regulation of Chemokine Receptors CCR4 and CCR8 upon Activating of Polarized . . . ", *J. of Immunology*, Cutting Edge, 0022-1767/98/502. 00, pp. 5111-5115, 1998.
Bonecchi, et al., "Differential Expression of Chemokine Receptors and Chemotactic Responsiveness of Type 1 T Helper . . . ", J. Exp. Med., vol. 87, No. 1 (1998), pp. 129-134.
Youn et al., "Molecular Cloning and Characterization of a cDNA, CHEMR, Encoding a Chemokine Receptor with . . . ", *Blood*, vol. 89, No. 12 (1997), pp. 4448-4460.
Frade, et al., "The Amino-terminal Domain of the CCR2 Chemokine Receptor Acts as Coreceptor for HIV-1 Infection", *J. Clin. Invest.*, vol. 100, No. 3, (1997), pp. 497-502.
Sims, et al., "A Humanized CD18 Antibody Can Block Function without cell Destruction", *The Journal of Immunology*, vol. 151, No. 4 (1993), pp. 2177-2335.
Brams et al., "A humanized anti-human CD154 monoclonal antibody blocks CD154-CD40 mediated human B cell activation", *Int. Immunopharmacol.*, (2001); vol. 1, pp. 277-294.
Bendig, *Methods: A Companion to Methods in Enzymology*, vol. 8 (1995), pp. 83-93.
Yoneyama et al., *J. Clin. Invest.*, vol. 102, No. 11 (1998), pp. 1933-1941.

(Continued)

*Primary Examiner*—Phillip Gambel
*Assistant Examiner*—Sharon Wen
(74) *Attorney, Agent, or Firm*—Sughrue Mion, PLLC

(57) ABSTRACT

A recombinant antibody or the antibody fragment thereof which specifically reacts with an extracellular domain of human CCR4; a DNA which encodes the recombinant antibody or the antibody fragment thereof; a method for producing the recombinant antibody or the antibody fragment thereof; a method for immunologically detecting CCR4, a method for immunologically detecting a cell which expressed CCR4 on the cell surface, a method for depleting a cell which expresses CCR4 on the cell surface, and a method for inhibiting production of Th2 cytokine, which comprise using the recombinant antibody according or antibody fragment thereof; a therapeutic or diagnostic agent for Th2-mediated immune diseases; and a therapeutic or diagnostic agent for a blood cancer.

32 Claims, 18 Drawing Sheets

OTHER PUBLICATIONS

Suzuki, et al., *Int. Immunol.*, vol. 11, No. 4 (1999), pp. 553-559.

Imai, et al., "Selective recruitement of CCR4-bearing $T_h2$ cells toward antigen-presenting cells by the CC chemokines thymus and activation-regulated . . . ", *International Immunology*, vol. 11, No. 1 (1999), pp. 81-88.

Andrew, et al., *J. Immunol.*, vol. 166, No. 1 (2001), pp. 103-111.

Landolfi, et al., *J. Immunol.*, vol. 166, No. 3 (2001), pp. 1748-1754.

He, et al., *J. Immunol.*, vol. 160, No. 2 (1998), pp. 1029-1035.

Brown, et al., *Proc. Natl. Acad. Sci.* USA, vol. 88, No. 7 (1991), pp. 2663-2667.

Co, et al., *Proc. Natl. Acad. Sci.* USA, vol. 88, No. 7 (1991), pp. 2869-2873.

Junghans, et al., *Cancer Res.*, vol. 50, No. 5 (1990), pp. 1495-1502.

Queen et al, *Proc. Natl. Acad. Sci.* USA, vol. 86, No. 24, pp. 10029-10033, 1989.

\* cited by examiner

FIG.10
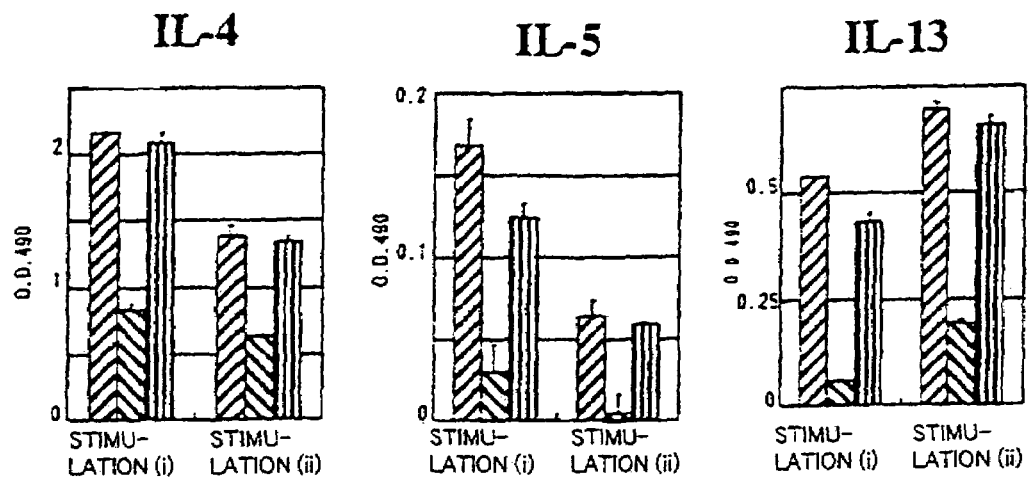
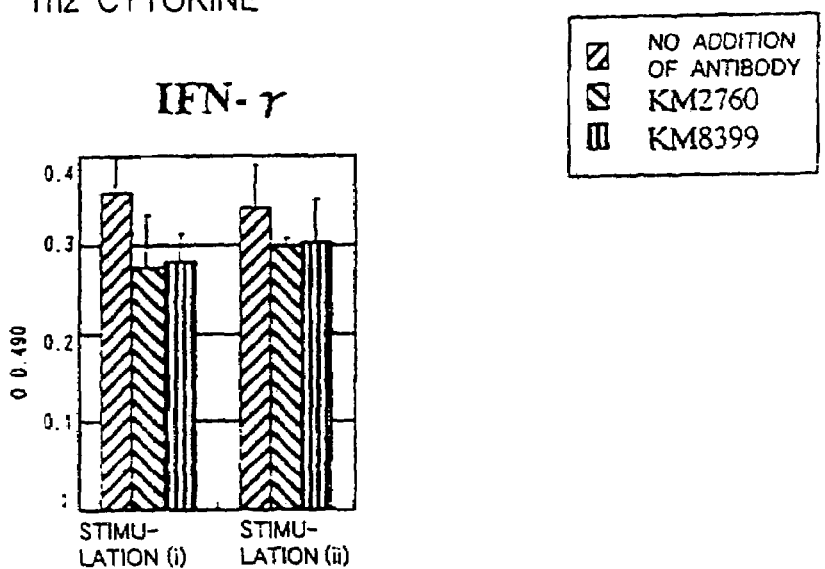

SEQUENCE LISTING

<160> NUMBER OF SEQ ID NOS: 17

<210> SEQ ID NO 1
<211> LENGTH: 28
<212> TYPE: PRT
<213> ORGANISM: Homo sapiens

<400> SEQUENCE: 1

```
Asn Pro Thr Asp Ile Ala Asp Thr Thr Leu Asp Glu Ser Ile Tyr Ser
  1               5                  10                  15

Asn Tyr Tyr Leu Tyr Glu Ser Ile Pro Lys Pro Cys
             20                  25
```

<210> SEQ ID NO 2
<211> LENGTH: 28
<212> TYPE: PRT
<213> ORGANISM: Mus musculus

<400> SEQUENCE: 2

```
Asn Ala Thr Glu Val Thr Asp Thr Thr Gln Asp Glu Thr Val Tyr Asn
  1               5                  10                  15

Ser Tyr Tyr Phe Tyr Glu Ser Met Pro Lys Pro Cys
             20                  25
```

<210> SEQ ID NO 3
<211> LENGTH: 414
<212> TYPE: DNA
<213> ORGANISM: Mus musculus
<220> FEATURE:
<221> NAME/KEY: CDS
<222> LOCATION: (1)..(414)

<400> SEQUENCE: 3

```
atg aac ctc ggg ctc agt ttg att ttc ctt gcc ctc att tta aaa ggt      48
Met Asn Leu Gly Leu Ser Leu Ile Phe Leu Ala Leu Ile Leu Lys Gly
  1               5                  10                  15 gtc cag tgt gag gtg cag ctg gtg gag tct ggg gga gac tta atg aag      96
Val Gln Cys Glu Val Gln Leu Val Glu Ser Gly Gly Asp Leu Met Lys
             20                  25                  30 cct gga ggg tcc ctg aaa atc tcc tgt gca gcc tct gga ttc att ttc     144
Pro Gly Gly Ser Leu Lys Ile Ser Cys Ala Ala Ser Gly Phe Ile Phe
         35                  40                  45
```

```
agt aat tat ggc atg tct tgg gtt cgc cag act cca gac atg agg ctg      192
Ser Asn Tyr Gly Met Ser Trp Val Arg Gln Thr Pro Asp Met Arg Leu
     50                  55                  60 gaa tgg gtc gca acc att agt agt gct agt act tat tcc tat tat cca      240
Glu Trp Val Ala Thr Ile Ser Ser Ala Ser Thr Tyr Ser Tyr Tyr Pro
 65                  70                  75                  80 gac agt gtg aag gga cga ttc acc ata tcc agg gac aac gcc gag aac      288
Asp Ser Val Lys Gly Arg Phe Thr Ile Ser Arg Asp Asn Ala Glu Asn
             85                  90                  95 tcc cta tat ctg caa atg aat agt ctg agg tct gag gac aca ggc ata      336
Ser Leu Tyr Leu Gln Met Asn Ser Leu Arg Ser Glu Asp Thr Gly Ile
            100                 105                 110 tat tac tgt gga aga cat agc gat gga aac ttc gcg ttt ggt tat tgg      384
Tyr Tyr Cys Gly Arg His Ser Asp Gly Asn Phe Ala Phe Gly Tyr Trp
        115                 120                 125 ggc cga ggg act ctg gtc act gtc tct gca                              414
Gly Arg Gly Thr Leu Val Thr Val Ser Ala
    130                 135

<210> SEQ ID NO 4
<211> LENGTH: 396
<212> TYPE: DNA
<213> ORGANISM: Mus musculus
<220> FEATURE:
<221> NAME/KEY: CDS
<222> LOCATION: (1)..(396)

<400> SEQUENCE: 4 atg aag ttg cct gtt agg ctg ttg gtg ctg atg ttc tgg att cct gct       48
Met Lys Leu Pro Val Arg Leu Leu Val Leu Met Phe Trp Ile Pro Ala
 1               5                  10                  15 tcc agc agt gat gtt ttg atg acc caa act cca ctc tcc ctg cct gtc       96
Ser Ser Ser Asp Val Leu Met Thr Gln Thr Pro Leu Ser Leu Pro Val
             20                  25                  30 agt ctt gga gat caa gcc tcc atc tct tgc aga tct agt cgg aac att      144
Ser Leu Gly Asp Gln Ala Ser Ile Ser Cys Arg Ser Ser Arg Asn Ile
         35                  40                  45 gtt cat att aat ggt gac aca tat tta gaa tgg tac ctg cag aga ccg      192
Val His Ile Asn Gly Asp Thr Tyr Leu Glu Trp Tyr Leu Gln Arg Pro
     50                  55                  60 ggc cag tct cca aag ctc cta atc tac aaa gtt tcc aac cga ttt tct      240
Gly Gln Ser Pro Lys Leu Leu Ile Tyr Lys Val Ser Asn Arg Phe Ser
 65                  70                  75                  80 ggg gtc cca gac agg ttc agt ggc agt gga tca ggg aca gat ttc aca      288
Gly Val Pro Asp Arg Phe Ser Gly Ser Gly Ser Gly Thr Asp Phe Thr
             85                  90                  95 ctc aag atc agc aga gtg gag gct gag gat ctg gga gtt tat tac tgc      336
Leu Lys Ile Ser Arg Val Glu Ala Glu Asp Leu Gly Val Tyr Tyr Cys
        100                 105                 110 ttt caa ggt tca ctt ctt ccg tgg acg ttc ggt gga ggc acc agg ctg      384
Phe Gln Gly Ser Leu Leu Pro Trp Thr Phe Gly Gly Gly Thr Arg Leu
    115                 120                 125 gaa atc aga cgg                                                       396
Glu Ile Arg Arg
    130

<210> SEQ ID NO 5
<211> LENGTH: 5
<212> TYPE: PRT
<213> ORGANISM: Mus musculus
```

```
<400> SEQUENCE: 5

Asn Tyr Gly Met Ser
 1               5

<210> SEQ ID NO 6
<211> LENGTH: 17
<212> TYPE: PRT
<213> ORGANISM: Mus musculus

<400> SEQUENCE: 6

Thr Ile Ser Ser Ala Ser Thr Tyr Ser Tyr Pro Asp Ser Val Lys
 1               5                  10                  15

Gly

<210> SEQ ID NO 7
<211> LENGTH: 10
<212> TYPE: PRT
<213> ORGANISM: Mus musculus

<400> SEQUENCE: 7

His Ser Asp Gly Asn Phe Ala Phe Gly Tyr
 1               5                  10

<210> SEQ ID NO 8
<211> LENGTH: 16
<212> TYPE: PRT
<213> ORGANISM: Mus musculus

<400> SEQUENCE: 8

Arg Ser Ser Arg Asn Ile Val His Ile Asn Gly Asp Thr Tyr Leu Glu
 1               5                  10                  15

<210> SEQ ID NO 9
<211> LENGTH: 7
<212> TYPE: PRT
<213> ORGANISM: Mus musculus

<400> SEQUENCE: 9

Lys Val Ser Asn Arg Phe Ser
 1               5

<210> SEQ ID NO 10
<211> LENGTH: 9
<212> TYPE: PRT
<213> ORGANISM: Mus musculus

<400> SEQUENCE: 10

Phe Gln Gly Ser Leu Leu Phe Trp Thr
 1               5

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: synthetic
      DNA oligonucleotide

<400> SEQUENCE: 11
aaggaaaaaa gcggccgcga cccctcacca tgaacctcg                          39
```

```
<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: synthetic
      DNA oligonucleotide

<400> SEQUENCE: 12
cgatgggccc ttggtggagg ctgcagagac agtgaccag                              39

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: synthetic
      DNA oligonucleotide

<400> SEQUENCE: 13
ccggaattcg cctcctcaaa atgaagttgc c                                      31

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: synthetic
      DNA oligonucleotide

<400> SEQUENCE: 14
agccaccgta cgtctgattt ccagcctggt g                                      31

<210> SEQ ID NO 15
<211> LENGTH: 138
<212> TYPE: PRT
<213> ORGANISM: Mus musculus

<400> SEQUENCE: 15

Met Asn Leu Gly Leu Ser Leu Ile Phe Leu Ala Leu Ile Leu Lys Gly
 1               5                  10                  15

Val Gln Cys Glu Val Gln Leu Val Glu Ser Gly Gly Asp Leu Met Lys
             20                  25                  30

Pro Gly Gly Ser Leu Lys Ile Ser Cys Ala Ala Ser Gly Phe Ile Phe
         35                  40                  45

Ser Asn Tyr Gly Met Ser Trp Val Arg Gln Thr Pro Asp Met Arg Leu
     50                  55                  60

Glu Trp Val Ala Thr Ile Ser Ser Ala Ser Thr Tyr Ser Tyr Tyr Pro
 65                  70                  75                  80

Asp Ser Val Lys Gly Arg Phe Thr Ile Ser Arg Asp Asn Ala Glu Asn
                 85                  90                  95

Ser Leu Tyr Leu Gln Met Asn Ser Leu Arg Ser Glu Asp Thr Gly Ile
            100                 105                 110

Tyr Tyr Cys Gly Arg His Ser Asp Gly Asn Phe Ala Phe Gly Tyr Trp
        115                 120                 125

Gly Arg Gly Thr Leu Val Thr Val Ser Ala
    130                 135

<210> SEQ ID NO 16
<211> LENGTH: 132
<212> TYPE: PRT
<213> ORGANISM: Mus musculus
```

<400> SEQUENCE: 16

```
Met Lys Leu Pro Val Arg Leu Leu Val Leu Met Phe Trp Ile Pro Ala
 1               5                  10                  15

Ser Ser Ser Asp Val Leu Met Thr Gln Thr Pro Leu Ser Leu Pro Val
             20                  25                  30

Ser Leu Gly Asp Gln Ala Ser Ile Ser Cys Arg Ser Ser Arg Asn Ile
         35                  40                  45

Val His Ile Asn Gly Asp Thr Tyr Leu Glu Trp Tyr Leu Gln Arg Pro
     50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Tyr Cys
            100                 105                 110

Phe Gln Gly Ser Leu Leu Pro Trp Thr Phe Gly Gly Gly Thr Arg Leu
        115                 120                 125

Glu Ile Arg Arg
        130
```

<210> SEQ ID NO 17
<211> LENGTH: 360
<212> TYPE: PRT
<213> ORGANISM: Homo sapiens

<400> SEQUENCE: 17

```
Met Asn Pro Thr Asp Ile Ala Asp Thr Thr Leu Asp Glu Ser Ile Tyr
 1               5                  10                  15

Ser Asn Tyr Tyr Leu Tyr Glu Ser Ile Pro Lys Pro Cys Thr Lys Glu
             20                  25                  30

Gly Ile Lys Ala Phe Gly Glu Leu Phe Leu Pro Pro Leu Tyr Ser Leu
         35                  40                  45

Val Phe Val Phe Gly Leu Leu Gly Asn Ser Val Val Val Leu Val Leu
     50                  55                  60

Phe Lys Tyr Lys Arg Leu Arg Ser Met Thr Asp Val Tyr Leu Leu Asn
 65                  70                  75                  80

Leu Ala Ile Ser Asp Leu Leu Phe Val Phe Ser Leu Pro Phe Trp Gly
                 85                  90                  95

Tyr Tyr Ala Ala Asp Gln Trp Val Phe Gly Leu Gly Leu Cys Lys Met
            100                 105                 110

Ile Ser Trp Met Tyr Leu Val Gly Phe Tyr Ser Gly Ile Phe Phe Val
        115                 120                 125

Met Leu Met Ser Ile Asp Arg Tyr Leu Ala Ile Val His Ala Val Phe
    130                 135                 140

Ser Leu Arg Ala Arg Thr Leu Thr Tyr Gly Val Ile Thr Ser Leu Ala
145                 150                 155                 160

Thr Trp Ser Val Ala Val Phe Ala Ser Leu Pro Gly Phe Leu Phe Ser
                165                 170                 175

Thr Cys Tyr Thr Glu Arg Asn His Thr Tyr Cys Lys Thr Lys Tyr Ser
            180                 185                 190

Leu Asn Ser Thr Thr Trp Lys Val Leu Ser Ser Leu Glu Ile Asn Ile
        195                 200                 205

Leu Gly Leu Val Ile Pro Leu Gly Ile Met Leu Phe Cys Tyr Ser Met
    210                 215                 220
```

-continued

```
Ile Ile Arg Thr Leu Gln His Cys Lys Asn Glu Lys Lys Asn Lys Ala
225                 230                 235                 240

Val Lys Met Ile Phe Ala Val Val Val Leu Phe Leu Gly Phe Trp Thr
            245                 250                 255

Pro Tyr Asn Ile Val Leu Phe Leu Glu Thr Leu Val Glu Leu Glu Val
            260                 265                 270

Leu Gln Asp Cys Thr Phe Glu Arg Tyr Leu Asp Tyr Ala Ile Gln Ala
        275                 280                 285

Thr Glu Thr Leu Ala Phe Val His Cys Cys Leu Asn Pro Ile Ile Tyr
        290                 295                 300

Phe Phe Leu Gly Glu Lys Phe Arg Lys Tyr Ile Leu Gln Leu Phe Lys
305                 310                 315                 320

Thr Cys Arg Gly Leu Phe Val Leu Cys Gln Tyr Cys Gly Leu Leu Gln
            325                 330                 335

Ile Tyr Ser Ala Asp Thr Pro Ser Ser Ser Tyr Thr Gln Ser Thr Met
            340                 345                 350

Asp His Asp Leu His Asp Ala Leu
            355                 360
```

METHOD FOR TREATING TH2-MEDIATED DISEASE

This application is a division of application Ser. No. 09/796,744 filed Mar. 2, 2001 (now U.S. Pat. No. 6,989,145, issued Jan. 24, 2006).

BACKGROUND OF THE INVENTION

1. Field of the Invention

The present invention relates to a recombinant antibody and an antibody fragment thereof which specifically react with the extracellular domain of human CC chemokine receptor 4 (hereinafter referred to as "CCR4"). Furthermore, the present invention relates to a recombinant antibody such as humanized antibody, human antibody and the like, and an antibody fragment thereof which specifically react with CCR4, have cytotoxic activity and activity of inhibiting production of cytokine by Th2 cells, and comprise a specific complementarity determining region (hereinafter referred to as "CDR"). Moreover, the present invention relates to a DNA encoding the above mentioned antibody. Also, the present invention relates to a vector comprising the DNA, and a transformant transformed with the vector. Still furthermore, the present invention relates to a method for producing the above mentioned antibody using the transformant, and a medicament such as a therapeutic agent, a diagnostic agent and the like, for Th2-mediated immune diseases such as allergic diseases and the like, which comprises using the antibody. Still moreover, the present invention relates to a medicament such as a therapeutic agent, a diagnostic agent and the like, for cancers such as blood cancers, e.g., leukemia, which comprises using the antibody.

2. Brief Description of the Background Art

Various factors such as eosinophils, mast cells, IgE and the like, relate to allergic diseases such as bronchial asthma. Eosinophils infiltrate into an inflammatory part, release a cytotoxic basic protein such as MBP (major basic protein) or the like, by degranulation to thereby induce injury of surrounding tissues. Mast cells release histamine by binding to an antigen immune complex with IgE produced from B cells to thereby induce an immediate allergic reaction. They are controlled by biologically functional molecules such as cytokine, chemokine, and the like, which take part in signal transduction between cells. Eosinophils are subjected to differentiation induction and life span prolongation by IL-5, and degranulation is further induced. IgE is produced from B cells activated by IL-4 and becomes an immune complex with the antigen to accelerate degranulation of mast cells. It has been found that IL-4, IL-13 and the like are also produced from mast cells and contribute to the production of IgE from B cells, and the presence of an allergy reinforcing loop has been confirmed (*Am. J. Respir. Crit. Care Med.*, 152: 2059 (1995), *Immunol. Today*, 15: 19 (1994)). Thus, an elaborately cytokine-chemokine network is present between inflammatory cells and keeps complicated balances.

The cytokine and chemokine are produced by helper T cells which express CD4 on the cell surface (hereinafter referred to as "CD4+ Th cells"). Actually, it has been found that infiltration of helper T cells is remarkably found in the airway inflammation part of bronchial asthma patients, wherein a considerably large number of the T cells are activated and that the degree of seriousness and airway hypersensitivity of asthma correlates with the number of activated T cells, as well as the activated T cells are also increased in the peripheral blood (*Am. Rev. Respir. Dis.*, 145: S22 (1992)).

The helper T cells are classified into Th1 cells and Th2 cells, depending on the kind of cytokine to be produced thereby (*Annu. Rev. Immunol.*, 7: 145 (1989)). Examples of the cytokine produced by Th2 cells include IL-4, IL-5, IL-13, and the like.

It has been found that an antigen-specific T cell clone isolated from an atopic disease patient releases Th2 cytokine when stimulated in vitro (*Proc. Natl. Acad. Sci., U.S.A.*, 88: 4538 (1991)), and Th2 cells are present in bronchoalveolar lavage fluid (hereinafter referred to as "BAL") and airway mucosa of asthma patients (*N. Engl. J. Med.*, 326: 298 (1992), *Eur. J. Immunol.*, 23: 1445 (1993)). IL-4 and IL-5 of Th2 cytokines are increased when the expression of mRNA in BAL is examined using an allergic inflammation animal model (*Clin. Immunol. Immunopathol.*, 75: 75 (1995)). Also, when induced Th2 cells in mice are administered into the vein and nasal cavity, an antigen-specific asthmatoid inflammatory symptom is induced in the lungs (*J. Exp. Med.*, 186: 1737 (1997), *J. Immunol.*, 160: 1378 (1998)) and causes eosinophilia (*J. Immunol.*, 161: 3128 (1998)). Expression of IL-5 is observed in the airway mucous membrane of asthma patients and the lesions of atopic dermatitis patients (*J. Clin. Invest.*, 87: 1541 (1991), *J. Exp. Med.*, 173: 775 (1991)), and the expression level of IL-13 in the mucous membrane of continuous allergic rhinitis well correlates with the amounts of serum total IgE and antigen-specific IgE (*Therapeutics*, 32: 19 (1998)).

Chemokine is a general term for basic heparin-binding proteins having leukocyte migration and leukocyte activation functions, and classified into subfamilies of CXC, CC, C and $CX_3C$ depending on the position of the cysteine residue preserved on the primary structure. Up to date, 16 kinds of chemokine receptors have been identified (*Curr. Opi. Immunol.*, 11: 626 (1999)), and it has been shown that expression of each chemokine receptor is different on the surface of each leukocyte such as Th1 cell, Th2 cell or the like (*Cell Engineering*, 17: 1022 (1998)).

Human CCR4 is a G protein complexed seven transmembrane receptor cloned as K5-5 from a human immature basophilic cell line KU-812, and has the amino acid sequence represented by SEQ ID NO:17. Since the transmembrane regions of CCR4 are considered to be positions 40-67, positions 78-97, positions 113-133, positions 151-175, positions 207-226, positions 243-270 and positions 285-308, it is considered that the extracellular domains are positions 1-39, positions 98-112, positions 176-206 and positions 271-284 in the amino acid sequence, and that the intracellular regions are positions 68-77, positions 134-150, positions 227-242 and positions 309-360 (*J. Biol. Chem.*, 270: 19495 (1995)). When cloning was carried out, it was reported that the ligand of CCR4 is MIP-1α (macrophage inflammatory protein-1α), RANTES (regulated on activation normal T-cell expressed and secreted) or MCP-1 (monocyte chemotactic protein) (*Biochem. Biophys. Res. Commun.*, 218: 337 (1996), WO 96/23068). However, thereafter, it has been found that TARC (thymus and activation-regulated chemokine) produced from stimulated human peripheral blood mononuclear cells (hereinafter referred to as "PBMC") and thymus cells (*J. Biol. Chem.*, 271: 21514 (1996)) specifically binds to CCR4 (*J. Biol. Chem.*, 272: 15036 (1997)). It has been also reported that MDC (macrophage-derived chemokine) isolated from macrophage (*J. Exp. Med.*, 185: 1595 (1997)), also known as STCP-1 (stimulated T cell chemotactic protein-1) (*J. Biol. Chem.*, 272: 25229 (1997)), bind to CCR4 more strongly than TARC (*J. Biol. Chem.*, 273: 1764 (1998)).

It has been shown that CCR4 is expressed on CD4+ Th cells which produce cytokine and/or chemokine (*J. Biol.*

*Chem.,* 272: 15036 (1997)), and it has been reported that CCR4 is expressed selectively on Th2 cells among CD4+ Th cells (*J. Exp. Med.,* 187: 129 (1998), *J. Immunol.,* 161: 5111 (1998)). In addition, CCR4+ cells have been found in a group of effector/memory T cells (CD4+/CD45RO+), and when CCR4+ cells were stimulated, IL-4 and IL-5 were produced but IFN-γ was not produced (*Int. Immunol.,* 11: 81 (1999)). Also, it has been reported that CCR4+ cells belong to a CLA (cutaneous lymphocyte antigen)-positive and α4β8 integrin-negative group among memory T cells, and CCR4 is expressed on memory T cells related not to gut immunity but to systemic immunity of the skin and the like (*Nature,* 400: 776 (1999)). These results strongly suggest a possibility that the memory T cells which are activated by induction of inflammation express CCR4, migrate into the inflammatory site by ligands, MDC and TARC, and accelerate activation of other inflammatory cells.

As the current method for treating Th2-mediated immune diseases, the followings have been developed: (1) antagonists for cytokine and chemokine such as a humanized anti-IL-5 antibody (SB-240563: Smith Kline Beecham, Sch-55700 (CDP-835): Shehling Plaw/Celltech), a humanized IL-4 antibody (U.S. Pat. No. 5,914,110), a soluble chemokine receptor (*J. Immunol.,* 160: 624 (1998)), etc.; (2) cytokine chemokine production inhibitors such as an IL-5 production inhibitor (Japanese Published Unexamined Patent Application No. 53355/96), a retinoid antagonist (WO 99/24024), splatast tosilate (IPD-1151T, manufactured by Taiho Pharmaceutical), etc.; (3) agents for eosinophil, mast cell and the like as final inflammatory cells, such as a humanized IL-5 receptor antibody (WO 97/10354), a CC chemokine receptor 3 (CCR3) antagonist (Japanese Published Unexamined Patent Application No. 147872/99), etc.; (4) inflammatory molecule inhibitors such as a humanized anti-IgE antibody (*Am. J. Respir. Crit. Care Med.,* 157: 1429 (1998)), etc.; and the like. But they inhibit only a part of the elaborate network among cytokine, chemokine and inflammatory cells and are therefore not radical. Anti-CD4 antibodies have an ability to control T cells, and have effects on serious steroid-dependent asthma. However, since the CD4 molecule is broadly expressed in various immune cells, they lack in specificity and have a drawback of accompanying strong immunosuppressive effect (*Int. Arch. Aller. Immunol.,* 118: 133 (1999)).

Thus, in order to inhibit all of them, it is required to control specifically upstream of the problematic allergic reaction, namely Th2 cells.

The currently used principal method for treating patients of serious Th2-mediated immune diseases is steroid administration, but side effects by steroids cannot be avoided. Also, there are drawbacks that the conditions of each patient return to the original pathology when the steroid administration is suspended, and that drug resistance is acquired when the steroid is administered for a long time.

To date, no monoclonal antibody which can detect CCR4-expressing cells and also has cytotoxicity against CCR4-expressing cells has been established. In addition, no therapeutic agent which can inhibit production of Th2 cytokine has been known so far.

Although it has been reported that CCR4 is also expressed on leukemia (*Blood,* 96: 685 (2000)), no therapeutic agent which injures leukemia cells has been known.

It is known in general that when an antibody derived from a non-human animal, e.g., a mouse antibody, is administered to human, it is recognized as an foreign substance and induces a human antibody against the mouse antibody (human anti-mouse antibody: hereinafter referred to as "HAMA") in the human body. It is known that the HAMA reacts with the administered mouse antibody to cause side effects (*J. Clin. Oncol.,* 2: 881 (1984), *Blood,* 65: 1349 (1985), *J. Natl. Cancer Inst.,* 80: 932 (1988), *Proc. Natl. Acad. Sci. U.S.A.,* 82: 1242 (1985)), to quicken disappearance of the administered mouse antibody from the body (*J. Nucl. Med.,* 26: 1011 (1985), *Blood,* 65: 1349 (1985), *J. Natl. Cancer Inst.,* 80: 937 (1988)), and to reduce therapeutic effects of the mouse antibody (*J. Immunol.,* 135: 1530 (1985), *Cancer Res.,* 46: 6489 (1986)).

In order to solve these problems, attempts have been made to convert an antibody derived from a non-human animal into a humanized antibody such as a human chimeric antibody, a human complementarity determining region (hereinafter referred to as "CDR")-grafted antibody or the like using genetic engineering technique. The human chimeric antibody is an antibody in which its antibody variable region (hereinafter referred to as "V region") is an antibody derived from a non-human animal and its constant region (hereinafter referred to as "C region") is derived from a human antibody (*Proc. Natl. Acad. Sci. U.S.A.,* 81: 6851 (1984)). The human CDR-grafted antibody is an antibody in which the amino acid sequence of CDR in the V region derived from a non-human animal antibody is grafted into an appropriate position of a human antibody (*Nature,* 321: 522 (1986)). In comparison with antibodies derived from non-human animals such as mouse antibodies and the like, these humanized antibodies have various advantages for clinical applications. For example, regarding immunogenicity and stability in blood, it has been reported that blood half-life of a human chimeric antibody became about 6 times as long as a mouse antibody when administered to human (*Proc. Natl. Acad. Sci. U.S.A.,* 86: 4220 (1989)). In the case of a human CDR-grafted antibody, it has been reported that its immunogenicity was reduced and its serum half-life became 4 to 5 times as long as a mouse antibody in experiment using a monkey (*J. Immunol.,* 147: 1352 (1991)). Thus, it is expected that the humanized antibodies have less side effects and their therapeutic effects continue for a longer time than antibodies derived from non-human animals. Also, in treatment particularly for reducing the number of CCR4-expressing cells, higher cytotoxic activity such as complement-dependent cytotoxic activity (hereinafter referred to as "CDC activity"), antibody-dependent cell-mediated cytotoxic activity (hereinafter referred to as "ADCC activity") and the like, via the Fc region (the region in and after the hinge region of an antibody heavy chain) of an antibody are important for the therapeutic effects. It has been reported that on such cytotoxic activities, the human antibodies are superior to antibodies derived from non-human animals since the Fc region of human antibodies more efficiently activates human complement components and human effector cells having Fc receptor on the cell surface such as monocytes, macrophages, NK cells, and the like, than the Fc region of antibodies derived from non-human animals. For example, it has been reported that tumor cytotoxic activity by human effector cells was increased in a human chimeric antibody prepared by converting the Fc region of an mouse antibody for GD2 into the Fc region of a human antibody (*J. Immunol.,* 144: 1382 (1990)), and similar results have also been reported on a human CDR-grafted antibody for CAMPATH-1 antigen (*Nature,* 332: 323 (1988)).

These results clearly show that humanized antibodies are preferred to antibodies derived from non-human animals such as mouse antibodies and the like, as antibodies for clinical applications to human.

Furthermore, according to the recent advances in protein engineering and genetic engineering, antibody fragments having a smaller molecular weight such as Fab, Fab', F(ab')$_2$, a single chain antibody (hereinafter referred to as "scFv") (*Science*, 242: 423 (1988)), a disulfide stabilized V region fragment (hereinafter referred to as "dsFv") (*Molecular Immunol.*, 32: 249 (1995)) and the like, can be produced. Since the fragments are smaller in molecular weight than the complete antibody molecules, they are excellent in transitional ability into target tissues (*Cancer Res.*, 52: 3402 (1992)). It is considered that these fragments derived from humanized antibodies are more desirable than those derived from antibodies derived from non-human animals such as mouse antibodies, when used in clinical applications to human.

As described above, diagnostic and therapeutic effects can be expected from humanized antibodies and fragments thereof when used alone, but attempts have been made to further improve the effects by using other molecules in combination. For example, cytokine can be used as one of such molecules. Cytokine is a general term for various soluble factors which control intercellular mutual functions in immune reactions. CDC activity and ADCC activity, for example, are known as the cytotoxic activities of antibodies, and ADCC activity is controlled by effector cells having Fc receptors on the cell surface such as monocytes, macrophages, NK cells and the like (*J. Immunol.*, 138: 1992 (1987)). Since various cytokines activate these effector cells, they can be administered in combination with an antibody in order to improve ADCC activity of the antibody and the like.

SUMMARY OF THE INVENTION

Antibodies bind to the corresponding antigen via the CDRs of V regions of a heavy chain (hereinafter referred to as "H chain") and a light chain (hereinafter referred to as "L chain"), and the amino acid sequence of the CDR regulates binding reactivity and binding specificity of the antibody (*J. Exp. Med.*, 132: 211 (1970)). Thus, there is a demand for an anti-CCR4 antibody which contains CDRs having a novel amino acid sequence and specifically binds to human CCR4 having certain properties such as binding reactivity, cytotoxic activity and the like, which are different from those of known CCR4 antibodies. Furthermore, there is a demand for an antibody which can selectively deplete CCR4-expressing Th2 cells as cytokine-producing cells, an antibody which inhibits production of Th2 cytokine, and a diagnostic agent and therapeutic agent using the antibody. Moreover, there is a demand for a method useful in diagnosing and treating blood cancers such as leukemia which is a disease caused by tumorigenic transformation of hemopoietic cells, and the like.

The present inventors have obtained cDNAs encoding antibody H chain and L chain from hybridoma KM2160 which produces a mouse monoclonal antibody for CCR4 belonging to IgG1 class, have found that the V region CDRs have novel amino acid sequences, and have constructed a humanized antibody expression vector by cloning cDNAs encoding H chain V region and L chain V region having the novel CDRs into an animal cell expression vector having cDNAs encoding human antibody H chain C region and human antibody L chain C region. Anti-CCR4 chimeric antibody KM2760 was expressed and purified by introducing the expression vector into animal cells. The present invention has been accomplished by confirming that this antibody specifically reacts with human CCR4 and reduces the number of antigen-positive cells through its potent cytotoxic activity and by showing utility of the antibody in using in the human body.

In addition, the present inventors have accomplished the present invention by confirming that a recombinant antibody for CCR4 reacts with leukemia cells, particularly T cell leukemia cells, at a high frequency and reduces the number of CCR4-positive leukemia cells through its potent cytotoxic activity and by showing utility of the antibody in diagnosing and treating blood cancers such as human leukemia and the like.

The present invention relates to the following (1) to (47).

(1) A recombinant antibody or the antibody fragment thereof which specifically reacts with an extracellular domain of human CCR4.

(2) The recombinant antibody or the antibody fragment thereof according to (1), wherein the extracellular domain is an extracellular domain selected from the group consisting of positions 1-39, positions 98-112, positions 176-206, and positions 271-284 in the amino acid sequence represented by SEQ ID NO:17.

(3) The recombinant antibody or the antibody fragment thereof according to (1) or (2), which recognizes an epitope present in positions 2-29 in the amino acid sequence represented by SEQ ID NO:17.

(4) The recombinant antibody or the antibody fragment thereof according to any one of (1) to (3), which specifically reacts with a CCR4-expressing cell.

(5) The recombinant antibody or the antibody fragment thereof according to any one of (1) to (4), which has cytotoxic activity against a CCR4-expressing cell.

Examples of the cytotoxic activity include CDC activity, ADCC activity, and the like.

(6) The recombinant antibody or the antibody fragment thereof according to (5), wherein the cytotoxic activity against a CCR4-expressing cell is higher than that of a monoclonal antibody produced by a hybridoma derived from a non-human animal.

The term "cytotoxic activity higher than that of a monoclonal antibody produced by a hybridoma derived from a non-human animal" means that a cytotoxic activity of the obtained recombinant antibody is higher than that of a monoclonal antibody produced by a hybridoma derived from a non-human animal, which specifically reacts with CCR4 used in producing a recombinant antibody that will be described later.

(7) The recombinant antibody or the antibody fragment thereof according to (5), wherein the cytotoxic activity is antibody-dependent cell-mediated cytotoxic (ADCC) activity.

(8) The recombinant antibody or the antibody fragment thereof according to (7), wherein the antibody-dependent cell-mediated cytotoxic activity is activity of inducing apoptosis of a Th2 cell.

(9) The recombinant antibody or the antibody fragment thereof according to any one of (1) to (8), which has activity of depleting a Th2 cell.

(10) The recombinant antibody or the antibody fragment thereof according to any one of (1) to (9), which has activity of inhibiting production of Th2 cytokine.

(11) The recombinant antibody or the antibody fragment thereof according to (10), wherein the Th2 cytokine is IL-4, IL-5 or IL-13.

(12) The recombinant antibody according to any one of (1) to (11), wherein the recombinant antibody is selected from a humanized antibody and a human antibody.

(13) The recombinant antibody according to (12), wherein the humanized antibody is a human chimeric antibody or a human CDR-grafted antibody.

(14) The recombinant antibody according to any one of (1) to (13), which belongs to a human IgG antibody.

(15) The recombinant antibody according to (12), wherein the humanized antibody comprises:

complementarity determining region (CDR) 1, CDR2 and CDR3 of an antibody heavy chain (H chain) variable region (V region) having the amino acid sequences represented by SEQ ID NOs:5, 6 and 7, respectively; and CDR1, CDR2 and CDR3 of an antibody light chain (L chain) V region having the amino acid sequences represented by SEQ ID NOs:8, 9 and 10, respectively.

(16) The recombinant antibody according to (13), wherein the human chimeric antibody comprises:

an antibody heavy chain (H chain) variable region (V region) and antibody light chain (L chain) V region of a monoclonal antibody which specifically reacts with CCR4; and an H chain constant region (C region) and L chain C region of a human antibody.

(17) The recombinant antibody according to (16), wherein the human chimeric antibody comprises:

a complementarity determining region (CDR) 1, CDR2 and CDR3 of an H chain V region having the amino acid sequences represented by SEQ ID NOs:5, 6 and 7, respectively; and CDR1, CDR2 and CDR3 of an L chain V region having the amino acid sequences represented by SEQ ID NOs:8, 9 and 10, respectively.

(18) The recombinant antibody according to (13), wherein the human chimeric antibody comprises:

an H chain V region having amino acids 20-138 of the amino acid sequence represented by SEQ ID NO:15; and an L chain V region having amino acids 20-132 of the amino acid sequence represented by SEQ ID NO:16.

(19) The recombinant antibody according to (13), wherein the human chimeric antibody is an antibody KM2760 produced by a transformant KM2760 (FERM BP-7054), and wherein its antibody H chain C region belongs to human IgG1 subclass.

(20) The recombinant antibody according to (13), wherein the human CDR-grafted antibody comprises:

complementarity determining regions (CDRs) of an antibody heavy chain (H chain) variable region (V region) and an antibody light chain (L chain) V region of a monoclonal antibody which specifically reacts with CCR4; and C regions of an H chain and an L chain and a V region framework region of a human antibody.

(21) The recombinant antibody according to (20), wherein the human CDR-grafted antibody comprises:

CDR1, CDR2 and CDR3 of an H chain V region having the amino acid sequences represented by SEQ ID NOs:5, 6 and 7, respectively; and CDR1, CDR2 and CDR3 of an L chain V region having the amino acid sequences represented by SEQ ID NOs:8, 9 and 10, respectively.

(22) A DNA which encodes the recombinant antibody or the antibody fragment thereof according to any one of (1) to (21).

(23) A recombinant vector comprising the DNA according to (22) and a tandem vector for humanized antibody expression.

(24) A transformant to which the recombinant vector according to (23) is introduced into a host cell.

(25) The transformant according to (24), wherein the transformant is KM2760 (FERM BP-7054).

(26) A method for producing a recombinant antibody or the antibody fragment thereof, which comprises culturing the transformant according to (24) or (25) to produce and accumulate the recombinant antibody or the antibody fragment thereof in a culture medium, and recovering the recombinant antibody or the antibody fragment thereof from the culture medium.

(27) The recombinant antibody according to (12), wherein the human antibody comprises an antibody heavy chain (H chain) variable region (V region) and/or an antibody light chain (L chain) V region.

(28) The recombinant antibody according to (27), wherein complementarity determining regions (CDRs) of the H chain V region and L chain V region of the human antibody comprise amino acid sequences which are the same as amino acid sequences of CDRs of an H chain V region and an L chain V region, respectively, of a monoclonal antibody which specifically reacts with CCR4.

(29) The recombinant antibody according to (28), wherein the human antibody comprises:

CDR1, CDR2 and CDR3 of an H chain V region having the amino acid sequences represented by SEQ ID NOs:5, 6 and 7, respectively, and CDR1, CDR2 and CDR3 of an L chain V region having the amino acid sequences represented by SEQ ID NOs:8, 9 and 10, respectively.

(30) The recombinant antibody according to (27), wherein the H chain V region and L chain V region of the human antibody comprise amino acid sequences which are the same as amino acid sequences of an H chain V region and an L chain V region, respectively, of a monoclonal antibody which specifically reacts with CCR4.

(31) The recombinant antibody according to (30), wherein the human antibody comprises:

an H chain V region having amino acids of positions 20-138 in the amino acid sequence represented by SEQ ID NO:15; and/or an L chain V region having amino acids of positions 20-132 in the amino acid sequence represented by SEQ ID NO:16.

(32) The recombinant antibody according to any one of (27) to (31), wherein the human antibody is an antibody obtained from a human antibody phage library or a transgenic animal which produces a human antibody.

(33) The antibody fragment according to any one of (1) to (11), which is Fab, Fab', F(ab')$_2$, a single stranded antibody, a disulfide stabilized V region fragment, or a peptide comprising a complementarity determining region (CDR) of an antibody.

(34) The antibody fragment according to (33), which comprises an antibody heavy chain (H chain) variable region (V region) and/or an antibody light chain (L chain) V region of an antibody.

(35) The antibody fragment according to (34), wherein complementarity determining regions (CDRs) of the H chain V region and L chain V region of the antibody fragment comprise amino acid sequences which are the same as amino acid sequences of CDRs of an H chain V region and an L chain V region, respectively, of a monoclonal antibody which specifically reacts with CCR4.

(36) The antibody fragment according to (35), which comprises:

CDR1, CDR2 and CDR3 of the H chain V region having the amino acid sequences represented by SEQ ID NOs:5, 6 and 7, respectively; and CDR1, CDR2 and CDR3 of the L chain V region having the amino acid sequences represented by SEQ ID NOs:8, 9 and 10, respectively.

(37) The antibody fragment according to (34), wherein the H chain V region and L chain V region of the antibody fragment comprise amino acid sequences which are the same as amino acid sequences of an H chain V region and an L chain V region, respectively, of a monoclonal antibody which specifically reacts with CCR4.

(38) The antibody fragment according to (37), which comprises:

an H chain V region having amino acids of positions 20-138 in the amino acid sequence represented by SEQ ID NO:15; and an L chain V region having amino acids of positions of 20-132 in the amino acid sequence represented by SEQ ID NO:16.

(39) A recombinant antibody or the antibody fragment, which is the recombinant antibody or the antibody fragment thereof according to any one of (1) to (21) and (27) to (38) which is chemically or genetically conjugated with a radioisotope, a protein or an agent.

(40) A method for immunologically detecting CCR4, which comprises using the recombinant antibody or the antibody fragment thereof according to any one of (1) to (21) and (27) to (39).

For example, CCR4 in a sample can be immunologically detected by allowing the recombinant antibody or the antibody fragment thereof to contact with the sample.

(41) A method for immunologically detecting a cell which expresses CCR4 on the cell surface, which comprises using the recombinant antibody or the antibody fragment thereof according to any one of (1) to (21) and (27) to (39).

For example, a cell which expresses CCR4 on the cell surface can be immunologically detected by allowing the recombinant antibody or the antibody fragment thereof to contact with the cell.

(42) A method for reducing or depleting a cell which expressed CCR4 on the cell surface, which comprises using the recombinant antibody or the antibody fragment thereof according to any one of (1) to (21) and (27) to (39).

For example, the cell which expresses CCR4 on the cell surface can be reduced or depleted by administering an effective amount of the recombinant antibody or the antibody fragment thereof to human or an animal.

(43) A method for inhibiting production of Th2 cytokine, which comprises using the recombinant antibody or the antibody fragment thereof according to any one of (1) to (21) and (27) to (39).

For example, production of Th2 cytokine can be inhibited by administering an effective amount of the recombinant antibody or the antibody fragment thereof to human or an animal.

(44) A medicament comprising, as an active ingredient, the recombinant antibody or the antibody fragment thereof according to any one of (1) to (21) and (27) to (39).

(45) A therapeutic or diagnostic agent for Th2-mediated immune diseases, comprising, as an active ingredient, the recombinant antibody or the antibody fragment thereof according to any one of (1) to (21) and (27) to (39).

For example, a Th2-mediated immune disease can be treated by administering an effective amount of the recombinant antibody or the antibody fragment thereof to human or an animal, and a Th2-mediated immune disease can be diagnosed by allowing the recombinant antibody or the antibody fragment thereof to contact with a sample to be tested.

(46) A therapeutic or diagnostic agent for a blood cancer, comprising, as an active ingredient, the recombinant antibody or the antibody fragment thereof according to any one of (1) to (21) and (27) to (39).

For example, a blood cancer can be treated by administering an effective amount of the recombinant antibody or antibody fragment thereof to human or an animal, and a blood cancer can be diagnosed by allowing the recombinant antibody or antibody fragment thereof to contact with a sample to be tested.

(47) The therapeutic or diagnostic agent according to (46), wherein the blood cancer is leukemia.

BRIEF EXPLANATION OF THE DRAWINGS

FIG. 10 is a drawing showing the effect of inhibiting production of IL-4, IL-5, IL-13 and IFN-γ from human PBMC.

DETAILED DESCRIPTION OF THE INVENTION

Figure 1:
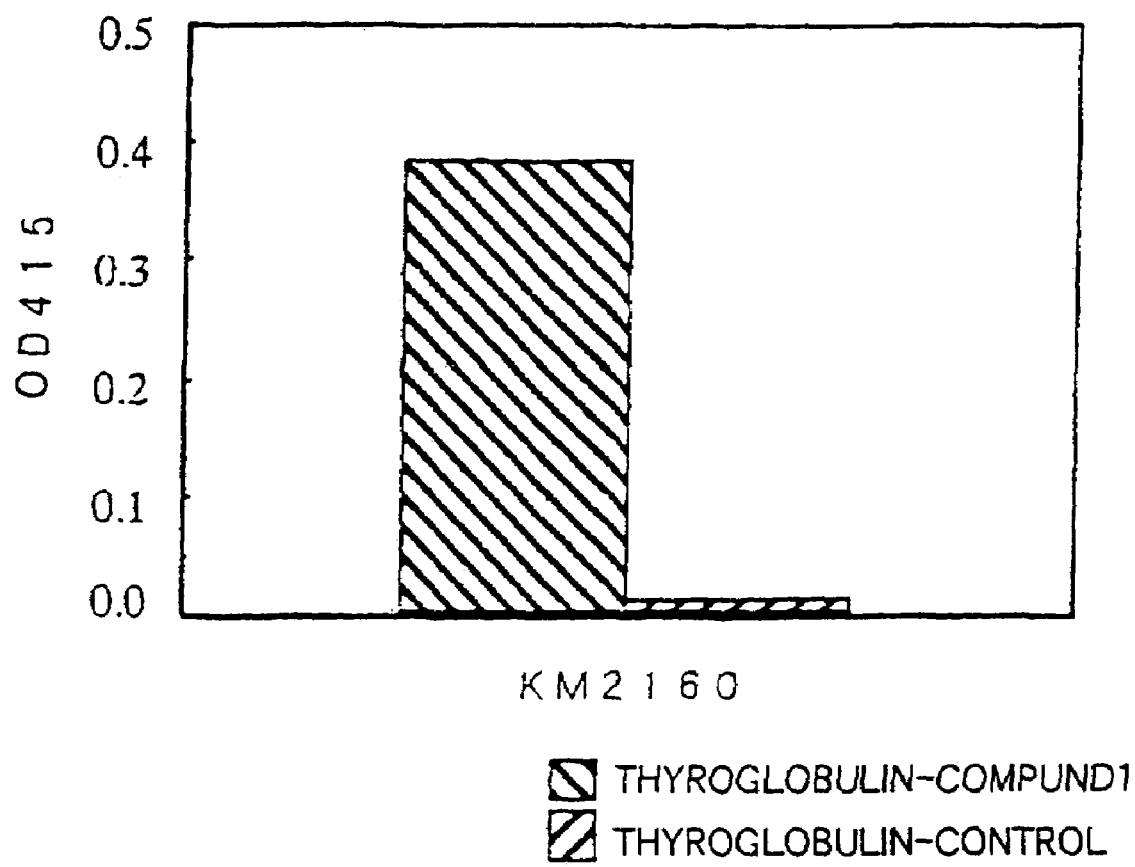
FIG. 1 is a drawing showing reactivity of KM2160 with a compound according to ELISA.

This application is based on Japanese applications No. 2000-59508 filed on Mar. 3, 2000 and No. 2000-401563 filed on Dec. 28, 2000, the entire contents of which are incorporated hereinto by reference.

Examples of the Th2-mediated immune diseases in the present invention include acute or chronic airway hypersensitivity or bronchial asthma, atopic skin diseases including atopic dermatitis, allergic rhinitis, pollinosis and the like.

Examples of the cancer in the present invention include blood cancers, and particularly leukemia.

Any recombinant antibody or the antibody fragment thereof according to the present invention (hereinafter referred to as the "antibody of the present invention") may be used, so long as it can react specifically with the extracellular domain of human CCR4. A preferred antibody is an antibody which specifically reacts with a domain comprising positions 1-39, positions 98-112, positions 176-206 or positions 271-284 of the amino acid sequence represented by SEQ ID NO:17. More preferred antibodies are an antibody comprising CDR1, CDR2 and CDR3 of an H chain V region having the amino acid sequences represented by SEQ ID NOs:5, 6 and 7, respectively, and CDR1, CDR2 and CDR3 of an L chain V region having the amino acid sequences represented by SEQ ID NOs:8, 9 and 10, respectively; and an antibody comprising an H chain V region having amino acids of positions 20-138 in the amino acid sequence represented by SEQ ID NO:15, and an L chain V region having amino acids of positions 20-132 in the amino acid sequence represented by SEQ ID NO:16. Antibodies and antibody fragments in which one or more amino acids are deleted, added, substituted and/or inserted in these amino acid sequences and which specifically react with CCR4 are also included within the scope of the present invention.

In the present invention, one or more amino acid deletion, substitution, insertion or addition in the amino acid sequence means that one or more amino acids are deleted, substituted, inserted and/or added to at one or plural positions in the amino acid sequence. The deletion, substitution, insertion and/or addition may be caused in the same amino acid sequence simultaneously. Also, the amino acid residue substituted, inserted or added can be natural or non-natural. Examples of the natural amino acid residue include L-alanine, L-asparagine, L-aspartic acid, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, L-cysteine, and the like.

Thereinafter, examples of amino acid residues which are substituted with each other are shown. The amino acid residues in the same group can be substituted with each other.

Group A:
leucine, isoleucine, norleucine, valine, norvaline, alanine, 2-aminobutanoic acid, methionine, O-methylserine, t-butylglycine, t-butylalanine, cyclohexylalanine;

Group B:
aspartic acid, glutamic acid, isoaspartic acid, isoglutamic acid, 2-aminoadipic acid, 2-aminosuberic acid;

Group C:
asparagine, glutamine;

Group D:
lysine, arginine, ornithine, 2,4-diaminobutanoic acid, 2,3-diaminopropionic acid;

Group E:
proline, 3-hydroxyproline, 4-hydroxyproline;

Group F:
serine, threonine, homoserine;

Group G:
phenylalanine, tyrosine.

Examples of the antibody of the present invention include a humanized antibody, a human antibody and the antibody fragment thereof as described below.

Examples of the humanized antibody include a human chimeric antibody and a human CDR-grafted antibody.

A human chimeric antibody is an antibody comprising an antibody H chain V region (hereinafter also referred to as "VH") and an antibody L chain V region (hereinafter also referred to as "VL") of a non-human animal, a human antibody H chain C region (hereinafter also referred to as "CH") and a human antibody L chain C region (hereinafter also referred to as "CL"). The non-human animal may be any of mouse, rat, hamster, rabbit and the like, so long as a hybridoma can be prepared therefrom.

The human chimeric antibody of the present invention can be produced by obtaining cDNAs encoding VH and VL from a hybridoma which produces a monoclonal antibody which reacts specifically with CCR4, inserting the cDNAs into an animal cell expression vector having genes encoding a human antibody CH and a human antibody CL to construct a human chimeric antibody expression vector, and introducing the vector into an animal cell to express the antibody.

Any CH of a human chimeric antibody may be used, so long as it belongs to human immunoglobulin (hereinafter referred to as "hIg"), but those of hIgG class are preferred, and any one of subclasses further belonging to hIgG such as hIgG1, hIgG2, hIgG3 and hIgG4, can be used. Also, any CL of a human chimeric antibody may be used, so long as it belongs to hIg, and those of κ class or λ class can be used.

Examples of the anti-CCR4 chimeric antibody include KM2760 in which VH of the antibody comprises an amino acid sequence of positions 20-138 in the amino acid sequence represented by SEQ ID NO:15, CH of the antibody comprises the amino acid sequence of hIgG1 subclass, VL of the antibody comprises an amino acid sequence of positions 20-132 of the amino acid sequence represented by SEQ ID NO:16, and CL of the antibody has the amino acid sequence of human antibody κ class.

A human CDR-grafted antibody is an antibody in which CDR amino acid sequences of VH and VL of an antibody derived from a non-human animal are grafted into appropriate positions of VH and VL of an human antibody.

The human CDR-grafted antibody of the present invention can be produced by grafting CDR sequences of VH and VL of an antibody which specifically reacts with CCR4 of a non-human animal into CDR sequences of VH and VL of an optional human antibody to construct cDNAs encoding V regions obtained, inserting the cDNAs into an animal cell expression vector having genes encoding human antibody CH and human antibody CL to construct a human CDR-grafted antibody expression vector, and then introducing the expression vector into an animal cell to express the antibody.

Any CH of human CDR-grafted antibody may be used, so long as it belongs to hIg, but those of hIgG class are preferred and any one of subclasses further belonging to hIgG such as hIgG1, hIgG2, hIgG3 and hIgG4, can be used. Also, any CL of human CDR-grafted antibody may be used so long as it belongs to hIg, and those of κ class or λ class can be used.

Originally, a human antibody is an antibody naturally existing in the human body, but it also includes antibodies obtained from a human antibody phage library and a human antibody producing transgenic animal, prepared based on the recent advance in genetic engineering, cell engineering and developmental engineering techniques.

The antibody existing in the human body can be obtained, for example, by isolating a human peripheral blood lymphocyte, immortalizing it by infection with EB virus or the like, followed by cloning, culturing a lymphocyte which produces the antibody, and purifying the antibody from the culture supernatant.

The human antibody library is a library in which an antibody fragment such as Fab, scFv or the like, is expressed on the surface of a phage by inserting an antibody gene prepared from human B cell into the phage gene. A phage which expresses an antibody fragment having desired antigen binding activity can be recovered from the library by using the binding activity to an antigen-immobilized substrate as the index. The antibody fragment can be further converted into a human antibody molecule comprising two complete H chains and two complete L chains by genetic engineering techniques.

A human antibody-producing transgenic animal is an animal in which a human antibody gene is introduced into its cell. Specifically, a human antibody-producing transgenic animal can be produced by introducing a human antibody gene into a mouse ES cell, inoculating the ES cell into an initial stage embryo of other mouse, and developing an animal. The human antibody may be produced and accumulated by obtaining a hybridoma producing a human antibody according to a hybridoma preparation method usually carried out in mammals other than human and then culturing the hybridoma to obtain the human antibody in a culture supernatant.

Examples of the antibody fragment include Fab, Fab', F(ab')$_2$, scFv, dsFv, a peptide comprising CDR, and the like.

An Fab is an antibody fragment having a molecular weight of about 50,000 and antigen binding activity, in which about a half of the N-terminal side of H chain and the entire L chain, among fragments obtained by treating IgG with a protease, papain (cut at the 224th position amino acid residue of the H chain), are bound together through a disulfide bond.

The Fab of the present invention can be obtained by treating an antibody which specifically reacts with CCR4, with a protease, papain. Alternatively, the Fab can be produced by inserting DNA encoding Fab of the antibody into an expression vector for prokaryote or an expression vector for eukaryote, and introducing the vector into a prokaryote or eukaryote to express the Fab.

An F(ab')$_2$ is an antibody fragment having a molecular weight of about 100,000 and antigen binding activity, which is slightly larger than the Fab bound via a disulfide bond of the hinge region, among fragments obtained by treating IgG with a protease, pepsin (cut at the 234th position amino acid residue of the H chain).

The F(ab')$_2$ of the present invention can be obtained by treating an antibody which specifically reacts with CCR4, with a protease, pepsin. Alternatively, it can be produced by binding Fab' described below via a thioether bond or a disulfide bond.

An Fab' is an antibody fragment having a molecular weight of about 50,000 and antigen binding activity, which is obtained by cutting a disulfide bond of the hinge region of the F(ab')$_2$.

The Fab' of the present invention can be obtained by treating the F(ab')$_2$ which specifically reacts with CCR4, with a reducing agent, dithiothreitol. Alternatively, the Fab' can be produced by inserting DNA encoding Fab' of the antibody into an expression vector for prokaryote or an expression vector for eukaryote, and introducing the vector into a prokaryote or eukaryote to express the Fab'.

An scFv is a VH-P-VL or VL-P-VH polypeptide in which one chain VH and one chain VL are linked using an appropriate peptide linker (hereinafter referred to as "P")) The VH and VL in the scFv of the present invention may be any antibody of the present invention which specifically reacts with CCR4 such as a humanized antibody or a human antibody.

The scFv of the present invention can be produced by obtaining cDNAs encoding VH and VL of an antibody which specifically reacts with CCR4, constructing DNA encoding scFv, inserting the DNA into an expression vector for prokaryote or an expression vector for eukaryote, and then introducing the expression vector into a prokaryote or eukaryote to express the scFv.

A dsFV is obtained by binding polypeptides in which one amino acid residue of each of VH and VL is substituted with a cysteine residue via a disulfide bond between the cysteine residues. The amino acid residue to be substituted with a cysteine residue can be selected based on a three-dimensional structure estimation of the antibody in accordance with the method shown by Reiter et al. (*Protein Engineering*, 7: 697 (1994)). As the VH and VL contained in the dsFv of the present invention, any antibody of the present invention which specifically reacts with CCR4 such as a humanized antibody or a human antibody, can be used.

The dsFv of the present invention can be produced by obtaining cDNAs encoding VH and VL of an antibody which specifically reacts with CCR4, constructing DNA encoding dsFv, inserting the DNA into an expression vector for prokaryote or an expression vector for eukaryote, and then introducing the expression vector into a prokaryote or eukaryote to express the dsFv.

A peptide comprising CDR is constituted by including at least one region of H chain and L chain CDRs. Plural CDRs can be bound directly or via an appropriate peptide linker.

The peptide comprising CDR of the present invention can be produced by obtaining cDNA encoding VH or VL of an antibody which specifically reacts with CCR4, constructing DNA encoding CDR, inserting the DNA into an expression vector for prokaryote or an expression vector for eukaryote, and then by introducing the expression vector into a prokaryote or eukaryote to express the peptide.

The peptide comprising CDR can also be produced by a chemical synthesis method such as an Fmoc method (fluorenylmethoxycarbonyl method), a tBoc method (t-butyloxycarbonyl method), or the like.

The antibody of the present invention includes antibody derivatives in which a radioisotope, a protein or an agent is chemically or genetically conjugated to an antibody which specifically reacts with CCR4 such as a humanized antibody, a human antibody or the antibody fragment thereof.

The antibody derivatives of the present invention can be produced by chemically conjugating a radioisotope, a protein or a agent to the N-terminal side or C-terminal side of an H chain or an L chain of an antibody or antibody fragment which specifically reacts with CCR4, to an appropriate substituent group or side chain of the antibody or antibody fragment or to a sugar chain in the antibody or antibody fragment (*Antibody Engineering Handbook*, edited by Osamu Kanemitsu, published by Chijin Shokan (1994)).

Alternatively, it can be genetically produced by linking a DNA encoding an antibody or antibody fragment which specifically reacts with CCR4 to other DNA encoding a protein to be bound, inserting the DNA into an expression vector, and introducing the expression vector into a host cell.

Examples of the isotope include $^{131}$I, $^{125}$I and the like, and they can be conjugated to antibodies by, e.g., a chloramine T method.

As the agent, a low molecular weight compound is preferred. Examples include anticancer agents such as alkylating agents (e.g., nitrogen mustard, cyclophosphamide, etc.), metabolic antagonists (e.g., 5-fluorouracil, methotrexate, etc.), antibiotics (e.g., daunomycin, bleomycin, mitomycin C, daunorubicin, doxorubicin, etc.), plant alkaloids (e.g., vincristine, vinblastine, vindesine, etc.), hormone drugs (e.g., tamoxifen, dexamethasone, etc.), and the like (*Clinical Oncology*, edited by Japanese Society of Clinical Oncology, published by Cancer and Chemotherapy (1996)); anti-inflammatory agents such as steroid agents (e.g., hydrocortisone, prednisone, etc.), non-steroidal drugs (e.g., aspirin, indometacin, etc.), immunomodulators (e.g., aurothiomalate, penicillamine, etc.), immunosuppressing agents (e.g., cyclophosphamide, azathioprine, etc.), antihistaminic agents (e.g., chlorpheniramine maleate, clemastine, etc.), and the like (*Inflammation and Anti-inflammatory Therapy*, Ishiyaku Shuppan (1982)); and the like. Examples of the method for conjugating daunomycin to an antibody include a method in which daunomycin and an amino group of an antibody are conjugated via glutaraldehyde, a method in which an amino group of daunomycin and a carboxyl group of an antibody are conjugated via a water-soluble carbodiimide, and the like.

As the protein, cytokine which activates immune cells is preferred as the protein. Examples include human interleukin 2 (hereinafter referred to as "hIL-2"), human granulocyte macrophage colony-stimulating factor (hereinafter referred to as "hGM-CSF"), human macrophage colony-stimulating factor (hereinafter referred to as "hM-CSF"), human interleukin 12 (hereinafter referred to as "hIL-12"), and the like. Also, in order to inhibit cancer cells directly, a toxin such as ricin, diphtheria toxin and the like, can be used. For example, a fusion antibody with a protein can be produced by linking a cDNA encoding an antibody or antibody fragment to other cDNA encoding the protein, constructing DNA encoding the fusion antibody, inserting the DNA into an expression vector for prokaryote or an expression vector for eukaryote, and then introducing it into a prokaryote or eukaryote to express the fusion antibody.

Methods for producing a human chimeric antibody which reacts specifically with CCR4 and has novel amino acid sequences in the V regions of H chain and L chain are explained below based on examples.

1. Production of Anti-CCR4 Monoclonal Antibody Produced by Hybridoma (1) Preparation of Antigen A recombinant CCR4 protein is obtained by introducing an expression vector containing cDNA encoding CCR4 into a host cell such as *Escherichia coli*, yeast, an insect cell, an animal cell or the like. Alternatively, a cultured tumor cell which expresses CCR4, a CCR4 protein purified from the cell or a synthetic peptide having a CCR4 partial sequence can be used as the antigen.

A partial protein sequence having approximately 5 to 30 residues is selected as a partial peptide for an antigen. In order to obtain an antibody which recognizes the protein having an unmodified natural structure, it is necessary to select a partial sequence existing on the surface of the three-dimensional structure of the protein as the antigen peptide. The part existing on the surface of the three-dimensional structure of the protein can be expected by estimating a partial sequence having high hydrophilicity using a commercially available protein sequence analyzing software such as Genetyx Mac™ or the like. In general, portions having low hydrophilicity are mostly present inside the three-dimensional protein structure, while portions having high hydrophilicity are mostly present on the protein surface. Also, the N-terminal and C-terminal of a protein are present on the protein surface in many cases. However, a partial peptide selected in this method does not always function as an antigen which establishes the target antibody.

In order to crosslink the partial peptide with the protein, a cysteine residue is added to the terminal region of the partial peptide. When an internal sequence of the protein is selected, N-terminal and C-terminal of the peptide are acetylated and amidated, respectively, if necessary.

The partial peptide can be synthesized by a usual liquid phase or solid phase peptide synthesis method, the combined method thereof or the modified method thereof (*The Peptides, Analysis, Synthesis, Biology*, vol. 1, edited by Erhard Gross and Johannes Meinhofer, Academic Press (1979), vol. 2 (1980), vol. 3 (1981); *Fundamentals and Experiments on Peptide Synthesis*, Nobuo Izumiya, Maruzen (1985); *Development of Drugs—Second Series*, vol. 14, Peptide Synthesis, edited by Haruaki Yajima, Hirokawa Shoten (1991); *International Journal of Peptide Protein Research*, 35: 161 (1990)).

Also, an automatic peptide synthesizer can be used. A peptide can be synthesized by a peptide synthesizer using amino acids with appropriate protected side chains such as Nα-Fmoc-amino acid, Nα-Boc-amino acid, and the like, on a commercially available peptide synthesizer, for example, a peptide synthesizer manufactured by Shimadzu, a peptide synthesizer manufactured by Applied Biosystems, Inc., USA (hereinafter referred to as "ABI"), a peptide synthesizer manufactured by Advanced ChemTech Inc., USA (hereinafter referred to as "ACT"), or the like, according to the synthesis program of each synthesizer.

Protected amino acids and carrier resins as starting materials can be purchased from ABI, Shimadzu, Kokusan Kagaku, Nova Biochem, Watanabe Kagaku, ACT, Peptide Institute or the like. Also, the protected amino acids, protected organic acids and protected organic amines as starting materials can be synthesized by known synthesis methods or modified methods thereof (*The Peptides, Analysis, Synthesis, Biology*, vol. 1, edited by Erhard Gross and Johannes Meinhofer, Academic Press (1979), vol. 2 (1980), vol. 3 (1981); *Fundamentals and Experiments on Peptide Synthesis*, Nobuo Izumiya, Maruzen (1985); Development of Drugs—Second Series, vol. 14, Peptide Synthesis, edited by Haruaki Yajima, Hirokawa Shoten (1991); *International Journal of Peptide Protein Research*, 35: 161 (1990)).

(2) Immunization of Animal and Preparation of Antibody-Producing Cell

Any animal such as mice, rats, hamsters, rabbits and the like, can be used in the immunization, so long as a hybridoma can be produced. An example using mice and rats is described below.

A 3- to 20-weeks-old mouse or rat is immunized with the antigen prepared in the above 1(1), and antibody-producing cells are collected from the spleen, lymph node or peripheral blood of the animal. The immunization is carried out by administering the antigen to the animal several times through subcutaneous, intravenous or intraperitoneal injection together with an appropriate adjuvant. Examples of the adjuvant include a complete Freund's adjuvant, a combination of aluminum hydroxide gel with pertussis vaccine, and the like. When the antigen is a partial peptide, a conjugate is produced with a carrier protein such as BSA (bovine serum albumin), KLH (keyhole limpet hemocyanin) or the like, which is used as the antigen. Three to seven days after each administration, a blood sample is collected from the fundus of the eye or caudal vein of the animal, the reactivity with the antigen used, CCR4, is tested, for example, by enzyme immunoassay (*Enzyme-linked Immunosorbent Assay* (*ELISA*), published by Igaku Shoin (1976)), and then a mouse or rat showing a sufficient antibody titer in their sera is used as the supply source of antibody-producing cells. On the 3rd to 7th days after final administration of the antigen, the spleen is excised from the immunized mouse or rat to carry out fusion of the spleen cells with myeloma cells according to the known method (*Antibodies—A Laboratory Manual*, Cold Spring Harbor Laboratory (1988)).

(3) Preparation of Myeloma Cell

Any myeloma cell can be used, so long as it proliferates in vitro. Examples include established cell lines obtained from mouse such as 8-azaguanine-resistant mouse (BALB/c) myeloma cell line P3-X63Ag8-U1 (P3-U1) (*Europ. J. Immunol*, 6: 511 (1976)), SP2/0-Ag14 (SP-2) (*Nature*, 276: 269 (1978)), P3-X63-Ag8653 (653) (*J. Immunol.*, 123: 1548 (1979)), P3-X63-Ag8 (X63) (*Nature*, 256: 495 (1975)), and the like. These cell lines are cultured and subcultured according to the known method (*Antibodies—A Laboratory Manual*, Cold Spring Harbor Laboratory (1988)) and $2 \times 10^7$ or more of the cells are secured until cell fusion.

(4) Cell Fusion

The above-obtained antibody-producing cells are washed, a cell aggregating medium such as polyethylene glycol-1000 (PEG-1000) or the like, was added thereto to fuse the cells, and the cells are suspended in the medium. For washing the cells, MEM medium, PBS (1.83 g of disodium hydrogen phosphate, 0.21 g of potassium dihydrogen phosphate, 7.65 g of sodium chloride, 1 liter of distilled water, pH 7.2) or the like can be used. Also, in order to obtain the target fused cells selectively, HAT medium {normal medium (a medium prepared by adding glutamine (1.5 mM), 2-mercaptoethanol ($5 \times 10^{-5}$ M), gentamicin (10 μg/ml) and fetal calf serum (FCS) (10%, manufactured by CSL) to RPHT-1640 medium further supplemented with hypoxanthine ($10^{-4}$ M), thymidine ($1.5 \times 10^{-5}$ M) and aminopterin ($4 \times 10^{-7}$ M)} can be used as the medium for suspending the fused cells.

After the culturing, a portion of the culture supernatant is sampled and a sample which reacts with an antigen protein but does not react to a non-antigen protein is selected by enzyme immunoassay. Thereafter, cloning is carried out by a limiting dilution method, and a hybridoma which shows a stably high antibody titer is selected as the monoclonal antibody-producing hybridoma.

(5) Selection of Hybridoma Producing Anti-CCR4 Monoclonal Antibody

A hybridoma producing an anti-CCR4 monoclonal antibody is selected by the assay described below according to the method described in *Antibodies, A Laboratory Manual*, Cold Spring Harbor Laboratory (1988) or the like. According to the assay, the binding activity of the anti-CCR4 human antibody contained in a culture supernatant of a transformant producing the anti-CCR4 human chimeric antibody described below or antibody fragment, or all purified anti-CCR4 antibodies can be measured.

Enzyme Immunoassay:

An antigen is coated on a 96-well ELISA plate. A reaction is carried out using a hybridoma culture supernatant or a purified antibody obtained in the above method as a first antibody.

After the reaction of the first antibody, the plate is washed and a second antibody is added thereto.

The second antibody is obtained by labeling an antibody which can recognize immunoglobulin of the first antibody with biotin, an enzyme, a chemiluminescent substance, a radioactive compound or the like. If a mouse is used for the production of the hybridoma, an antibody which can recognize mouse immunoglobulin is used as a second antibody.

After the reaction, a reaction suitable for the substance used for labeling the second antibody is carried out to select a hybridoma producing a monoclonal antibody which specifically reacts with the antigen.

Examples of the hybridoma include hybridoma KM2160.

(6) Purification of Monoclonal Antibody

The hybridoma cells producing an anti-CCR4 monoclonal antibody obtained in the above 1(4) are administered by intraperitoneal injection into 8- to 10-weeks-old mice or nude mice treated with pristane (0.5 ml of 2,6,10,14-tetramethylpentadecane (pristane) is intraperitoneally administred, followed by feeding for 2 weeks) at a dose of $2 \times 10^7$ to $5 \times 10^6$ cells/animal. The hybridoma causes ascites tumor in 10 to 21 days. The ascitic fluid is collected from the mice or nude mice, centrifuged, subjected to salting out with 40 to 50% saturated ammonium sulfate or to caprylic acid precipitation, and then passed through a DEAE-Sepharose column, protein A column or Cellulofine GSL 2000™ (manufactured by Seikagaku Corporation) to collect an IgG or IgM fraction as a purified monoclonal antibody.

The subclass of the purified monoclonal antibody can be determined using a mouse monoclonal antibody typing kit or a rat monoclonal antibody typing kit. The amount of the protein can be determined by the Lowry method or by absorbance at 280 nm.

The subclass of an antibody means isotypes within the class such as IgG1, IgG2a, IgG2b and IgG3 in the case of mouse, and IgG1, IgG2, IgG3 and IgG4 in the case of human.

The mouse IgG2a, IgG2b and IgG3 and human IgG1 and IgG3 types have relatively high cytotoxic activity such as CDC activity, ADCC activity and the like, so that they are useful in applying to medical treatments.

2. Production of Humanized Antibody (1) Construction of Humanized Antibody Expression Vector A humanized antibody expression vector is an expression vector for animal cell into which genes encoding an H chain C region and an L chain C region of a human antibody have been inserted, and is constructed by cloning each of the H chain C region and L chain C region of a human antibody into an expression vector for animal cell.

The C region of a human antibody may be an H chain C region and an L chain C region of any human antibody. Examples include a C region belonging to IgG1 subclass of an H chain of a human antibody (hereinafter referred to as "hCγ1"), a C region belonging to κ class of an L chain of a human antibody (hereinafter referred to as "hCκ"), and the like. As the gene encoding the H chain C region and L chain C region of a human antibody, a chromosomal DNA comprising an exon and an intron or cDNA can be used.

As the expression vector for animal cell, any expression vector can be used, so long as a C region of a human antibody can be inserted thereinto and expressed therein. Examples include pAGE107 (*Cytotechnology*, 3: 133 (1990)), pAGE103 (*J. Biochem.*, 101: 1307 (1987)), pHSG274 (*Gene*, 27: 223 (1984)), pKCR (*Proc. Natl. Acad. Sci. USA*, 78: 1527 (1981)), pSGI βd2-4 (*Cytotechnology*, 4: 173 (1990)), and the like. Examples of a promoter and enhancer used for an expression vector for animal cell include an SV40 early promoter and enhancer (*J. Biochem.*, 101: 1307 (1987)), a Moloney mouse leukemia virus LTR promoter and enhancer (*Biochem. Biophys. Res. Comun.*, 149: 960 (1987)), an immunoglobulin H chain promoter (*Cell*, 41: 479 (1985)) and enhancer (*Cell*, 33: 717 (1983)), and the like.

The humanized antibody expression vector may be either of a type in which a gene encoding an antibody H chain and a gene encoding an antibody L chain exist on separate vectors or of a type in which both genes exist on the same vector (tandem type). In respect of easiness of construction of a humanized antibody expression vector, easiness of introduction into animal cells, and balance between the expression amounts of antibody H and L chains in animal cells, a tandem type of the humanized antibody expression vector is more preferred (*J. Immunol. Methods*, 167: 271 (1994)). Examples of the tandem type of the humanized antibody expression vector include pKANTEX93 (WO 97/10354), pEE18 (HYBRIDOMA, 17: 559 (1998)), and the like.

The constructed humanized antibody expression vector can be used for expression of a human chimeric antibody and a human CDR-grafted antibody in animal cells.

(2) Preparation of cDNA Encoding V Region of Antibody Derived from Non-Human Animal and Analysis of Amino Acid Sequence cDNAs encoding the H chain V region and L chain V region of an antibody derived from an non-human animal such as a mouse antibody are obtained as follows.

mRNA is extracted from hybridoma cells producing a mouse antibody or the like to synthesize cDNA. The synthesized cDNA is inserted into a vector such as a phage, a plasmid or the like, to prepare a cDNA library. Each of a recombinant phage or recombinant plasmid containing cDNA encoding an H chain V region and a recombinant phage or recombinant plasmid containing cDNA encoding an L chain V region is isolated from the library using a part of the C region or V region of a mouse antibody as the probe. The full nucleotide sequences of the H chain V region and L chain V region of the mouse antibody of interest on the recombinant phage or recombinant plasmid are determined, and the full amino acid sequences of the H chain V region and L chain V region are deduced from the nucleotide sequences.

The non-human animal may be any animal such as mouse, rat, hamster, rabbit or the like, so long as a hybridoma cell can be produced therefrom.

Examples of the method for preparing total RNA from a hybridoma cell include a guanidine thiocyanate-cesium trifluoroacetate method (*Methods in Enzymol.*, 154: 3 (1987)) and the like. Examples of the method for preparing mRNA from total RNA include an oligo (dT) immobilized cellulose column method (*Molecular Cloning: A Laboratory Manual*, Cold Spring Harbor Lab. Press, New York (1989)) and the like. Also, examples of a kit for preparing mRNA from a hybridoma cell include Fast Track mRNA Isolation Kit™ (manufactured by Invitrogen), Quick Prep mRNA Purification Kit™ (manufactured by Pharmacia) and the like.

Examples of the method for synthesizing cDNA and preparing a cDNA library include known methods (*Molecular Cloning: A Laboratory Manual*, Cold Spring Harbor Lab. Press, New York (1989); *Current Protocols in Molecular Biology*, Supplement 1-34); a method using a commercially available kit such as Super Script™ Plasmid System for cDNA Synthesis and Plasmid Cloning (manufactured by GIBCO BRL), ZAP-cDNA Kit™ (manufactured by Stratagene), etc.; and the like.

The vector into which the cDNA synthesized using mRNA extracted from a hybridoma cell as the template is inserted for preparing a cDNA library may be any vector, so long as the cDNA can be inserted. Examples include ZAP Express (*Strategies*, 5: 58 (1992)), pBluescript II SK(+) (*Nucleic Acids Research*, 17: 9494 (1989)), λzapII (manufactured by Stratagene), λgt10 and λgt11 (*DNA Cloning: A Practical Approach*, I, 49 (1985)), Lambda BlueMid™ (manufactured by Clontech), λExCell and pT7T3 18U (manufactured by Pharmacia), pcD2 (*Mol. Cell. Biol.*, 3: 280 (1983)), pUC18 (*Gene*, 33: 103 (1985)), and the like.

Any *E. coli* for introducing the cDNA library constructed by a phage or plasmid vector may be used, so long as the cDNA library can be introduced, expressed and maintained. Examples include XL1-Blue MRF' (*Strategies*, 5: 81 (1992)), C600 (*Genetics*, 39: 440 (1954)), Y1088 and Y1090 (*Science*, 222: 778 (1983)), NM522 (*J. Mol. Biol.*, 166: 1 (1983)), K802 (*J. Mol. Biol.*, 16: 118 (1966)), JM105 (*Gene*, 38: 275 (1985)), and the like.

A colony hybridization or plaque hybridization method using an isotope- or fluorescence-labeled probe may be used for selecting cDNA clones encoding an H chain V region and an L chain V region of an antibody derived from a non-human animal in the cDNA library (*Molecular Cloning: A Laboratory Manual*, Cold Spring Harbor Lab. Press, New York (1989)). Also, the cDNAs encoding an H chain V region and an L chain V region can be prepared through polymerase chain reaction (hereinafter referred to as "PCR"; *Molecular Cloning: A Laboratory Manual*, Cold Spring Harbor Lab. Press, New York, 1989; *Current Protocols in Molecular Biology*, Supplement 1-34) by preparing primers and using cDNA prepared from mRNA or a cDNA library as the template.

The nucleotide sequence of the cDNA can be determined by digesting the cDNA selected by the above method with appropriate restriction enzymes and the like, cloning the fragments into a plasmid such as pBluescript SK(−)™ (manufactured by Stratagene) or the like, carrying out the reaction by a usually used nucleotide analyzing method such as the dideoxy method of Sanger, F. et al. (*Proc. Natl. Acad. Sci. USA*, 74: 5463 (1977)) or the like, and then analyzing the sequence using an automatic nucleotide sequence analyzer such as A.L.F. DNA sequencer (manufactured by Pharmacia) or the like.

Whether the obtained cDNAs encode the full amino acid sequences of the H chain V region and L chain V region of the antibody containing a secretory signal sequence can be confirmed by estimating the full amino acid sequences of the H chain V region and L chain V region from the determined nucleotide sequence and comparing them with full amino acid sequences of the H chain V region and L chain V region of known antibodies (*Sequences of Proteins of Immunological Interest*, US Dept. Health and Human Services (1991)). The length of the secretory signal sequence and N-terminal amino acid sequence can be deduced by comparing the full amino acid sequences of the H chain V region and L chain V region of the antibody comprising a secretory signal sequence with full amino acid sequences of the H chain V region and L chain V region of known antibodies (*Sequences of Proteins of*

Immunological Interest, US Dept. Health and Human Services (1991)), and the subgroup to which they belong can be known. Furthermore, the amino acid sequence of each of CDRs of the H chain V region and L chain V region can be found by comparing the obtained amino acid sequences with amino acid sequences of the H chain V region and L chain V region of known antibodies (Sequences of Proteins of Immunological Interest, US Dept. Health and Human Services (1991)).

Moreover, the novelty of the sequence can be examined by carrying out a homology search with sequences in any database, for example, SWISS-PROT, PIR-Protein or the like using the full amino acid sequences of the H chain V region and L chain V region, for example, according to the BLAST method (J. Mol. Biol., 215: 403 (1990)) or the like.

(3) Construction of Human Chimeric Antibody Expression Vector

A human chimeric antibody expression vector can be constructed by cloning cDNAs encoding an H chain V region and an L chain V region of an antibody derived from a non-human animal in a region upstream of genes encoding an H chain C region and an L chain C region of a human antibody on the humanized antibody expression vector as described in the above 2 (1). For example, each of cDNAs encoding an H chain V region and an L chain V region of an antibody derived from a non-human animal is linked with a synthesized DNA comprising nucleotide sequences at the 3' ends of an H chain V region and an L chain V region of an antibody derived from a non-human animal and nucleotide sequences at the 5' ends of an H chain C region and an L chain C region of a human antibody and having a recognition sequence of an appropriate restriction enzyme at both ends, and each cDNA is cloned so that it is appropriately expressed in upstream of genes encoding the H chain C region and L chain C region of the humanized antibody expression vector as described in the above 2(1) to thereby construct a human chimeric antibody expression vector. Also, cDNAs of the H chain V region and L chain V region of an antibody derived from a non-human animal are amplified by PCR using a synthetic DNA having a recognition sequence of an appropriate restriction enzyme at both ends, and each can be cloned into the humanized antibody expression vector as described in the above 2(1).

(4) Construction of cDNA Encoding V Region of Human CDR-Grafted Antibody cDNAs encoding an H chain V region and an L chain V region of a human CDR-grafted antibody can be obtained as follows. First, amino acid sequences of FRs in an H chain V region and an L chain V region of a human antibody to which amino acid sequences of CDRs in an H chain V region and an L chain V region of an antibody derived from a non-human animal antibody are grafted are selected. Any amino acid sequences of FRs in an H chain V region and an L chain V region of a human antibody can be used, so long as they are derived from human. Examples include amino acid sequences of FRs in an H chain V region and an L chain V region of human antibodies registered in database such as Protein Data Bank or the like, and amino acid sequences common to subgroups of FRs in the H chain V region and L chain V region of human antibodies (Sequences of Proteins of Immunological Interest, US Dept. Health and Human Services (1991)), and the like. In order to produce a human CDR-grafted antibody having potent activity, amino acid sequences having high homology (at least 60% or more) with amino acid sequence of FRs of an H chain V region and an L chain V region of a target antibody derived from a non-human animal is preferably selected. Then, amino acid sequences of CDRs of an H chain V region and an L chain V region of the antibody derived from a non-human animal are grafted to the selected amino acid sequences of FRs of an H chain V region and an L chain V region of a human antibody to design amino acid sequences of the H chain V region and L chain V region of a human CDR-grafted antibody. The designed amino acid sequences are converted to DNA sequences by considering the frequency of codon usage found in nucleotide sequences of genes of antibodies (Sequence of Proteins of Immunological Interest, US Dept. Health and Human Services (1991)), and the DNA sequences encoding the amino acid sequences of the H chain V region and L chain V region of a human CDR-grafted antibody are designed. Several synthetic DNAs having a length of about 100 nucleotides are synthesized, and PCR is carried out using them. In this case, it is preferred in each of the H chain and the L chain that 6 synthetic DNAs are designed in view of the reaction efficiency of PCR and the lengths of DNAs which can be synthesized.

Furthermore, they can be easily cloned into the humanized antibody expression vector constructed in the above 2(1) by introducing the recognition sequence of an appropriate restriction enzyme to the 5' end of the synthetic DNAs present on the both ends. After the PCR, an amplified product is cloned into a plasmid such as pBluescript SK (−)™ (manufactured by Stratagene) or the like, and the nucleotide sequences are determined according to the method described in the above 2(2) to obtain a plasmid having DNA sequences encoding the H chain V region and L chain V region of a designed human CDR-grafted antibody.

(5) Modification of Amino Acid Sequence of V Region of Human CDR-Grafted Antibody It is known that when a human CDR-grafted antibody is produced by simply grafting only CDRs in an H chain V region and an L chain V region of an antibody derived from a non-human animal in FRs of an H chain V region and an L chain V region of a human antibody, its antigen-binding activity is lower than that of the original antibody derived from a non-human animal (BIO/TECHNOLOGY, 9: 266 (1991)). As the reason, it is considered that several amino acid residues in not only CDRs but also FRs directly or indirectly relate to antigen-binding activity in the H chain V region and the L chain V region of the original antibody derived from a non-human animal, and that they are changed to different amino acid residues of different FRs in the H chain V region and the L chain V region of a human antibody. In order to solve the problem, in human CDR-grafted antibodies, among the amino acid sequences of FRs in an H chain V region and an L chain V region of a human antibody, an amino acid residue which directly relates to binding to an antigen, or an amino acid residue which indirectly relates to binding to an antigen by interacting with an amino acid residue in CDR or by maintaining the three-dimensional structure of an antibody is identified and modified to an amino acid residue which is found in the original non-human animal antibody to thereby increase the antigen binding activity which has been decreased (BIO/TECHNOLOGY, 9: 266 (1991)). In the production of a human CDR-grafted antibody, how to efficiently identify the amino acid residues relating to the antigen binding activity in FR is most important, so that the three-dimensional structure of an antibody is constructed and analyzed by X-ray crystallography (J. Mol. Biol., 112: 535 (1977)), computer-modeling (Protein Engineering, 7: 1501 (1994)) or the like. Although the information of the three-dimensional structure of antibodies has been useful in the production of a human CDR-grafted antibody, no method for producing a human CDR-grafted antibody which can be applied to any antibodies has been established yet. Therefore, various attempts must be currently be necessary, for example, several modified antibodies of each antibody are produced and the relationship between each of the modified antibodies and its antibody binding activity is examined.

The modification of the selected amino acid sequence of FR in the H chain V region and the L chain V region of a human antibody can be accomplished using various synthetic DNA for modification according to PCR as described in the above 2(4). With regard to the amplified product obtained by the PCR, the nucleotide sequence is determined according to the method as described in the above 2(2) so that whether the objective modification has been carried out is confirmed.

(6) Construction of Human CDR-Grafted Antibody Expression Vector

A human CDR-grafted antibody expression vector can be constructed by cloning cDNAs encoding the H chain V region and the L chain V region of the human CDR-grafted antibody constructed in the above 2(4) and 2(5) into upstream of the genes encoding the H chain C region and the L chain C region of the human antibody in the humanized antibody expression vector as described in the above 2(1).

For example, when recognition sites for an appropriate restriction enzymes are introduced to the 5'-terminal of synthetic DNAs positioned at both ends among synthetic DNAs used in the construction of the H chain V region and the L chain V region of the human CDR-grafted antibody in the above 2(4) and 2(5), cloning can be carried out so that they are expressed in an appropriate form in upstream of genes encoding the H chain C region and the L chain C region of the human antibody in the humanized antibody expression vector as described in the above 2(1).

(7) Transient Expression of Humanized Antibodies

In order to efficiently evaluate the antigen binding activity of various humanized antibodies produced, the humanized antibodies can be expressed transiently using the humanized antibody expression vector as described in the above 2(3) and 2(6) or the modified expression vector thereof. Any cell can be used as a host cell, so long as the host cell can express a humanized antibody. Generally, COS-7 cell (ATCC CRL1651) is used in view of its high expression amount (*Methods in Nucleic Acids Res.*, CRC Press, p. 283 (1991)). Examples of the method for introducing the expression vector into COS-7 cell include a DEAE-dextran method (*Methods in Nucleic Acids Res., CRC Press, p.* 283 (1991)), a lipofection method (*Proc. Natl. Acad. Sci. USA,* 84: 7413 (1987)), and the like.

After introduction of the vector, the expression amount and antigen binding activity of the humanized antibody in the culture supernatant can be determined by the enzyme immunoassay ((ELISA); *Antibodies: A Laboratory Manual*, Cold Spring Harbor Laboratory, Chapter 14 (1988), *Monoclonal Antibodies: Principles and Practice*, Academic Press Limited (1996)), and the like.

(8) Stable Expression of Humanized Antibody

A transformant which produces a humanized antibody stably can be obtained by introducing into an appropriate host cell the humanized antibody expression vector described in the above 2(3) and 2(6).

Examples of the method for introducing the expression vector into a host cell include electroporation (Japanese Published Unexamined Patent Application No. 257891/90, *Cytotechnology,* 3: 133 (1990)) and the like.

Any cell can be used as the host cell into which the humanized antibody expression vector is to be introduced, provided that it can express a humanized antibody. Examples include mouse SP2/0-Ag14 cell (ATCC CRL1581), mouse P3×63-Ag8.653 cell (ATCC CRL1580), CHO cell in which a dihydrofolate reductase gene (hereinafter referred to as "DHFR gene") is detective (*Proc. Natl. Acad. Sci. U.S.A.,* 77: 4216 (1980)), rat YB2/3HL.P2.G11.16Ag.20 cell (ATCC CRL1662, hereinafter referred to as "YB2/0 cell"), and the like.

A host cell for producing an antibody having antibody-dependent cell-mediated cytotoxic activity is preferably a cell having a low enzyme activity or no enzyme activity relating to a reaction in which fucose is added to N-acetylglucosamine bound to the Fc region of the antibody.

Examples of an enzyme for adding fucose to N-acetylglucosamine include enzymes relating to α1,6-bond such as α1,6-fucosyltransferase, enzymes relating to biosynthesis of GDP-fucose, e.g., GDP-mannose 4,6-dehydratase, GDP-β-L-fucosepyrophosphorylase, focokinase, and the like. Accordingly, cells obtained by subjecting cells used as the host cell to artificial mutation in which the gene of the enzyme is deleted or the gene is mutated to thereby reduce or neutralize the enzyme activity can also be used as the host cell.

As the host cell, any cell of bacteria, yeast, animal cells, insect cells, plant cells and the like can be used, so long as the recombinant antibody can be produced therein. Animal cells are preferred, and examples include YB2/0 cells, mouse myeloma cells such as NS0 cell and SP2/0 cell, Chinese hamster ovarian cells such as CHO/dhfr cell and CHO/DG44 cell, monkey cells such as COS cell, human myeloma cells such as Namalwa cell, and the like.

An antibody containing the sugar chain bound to the Fc region of the antibody having a high N-glucoside binding sugar chain content in which fucose does not bind to N-acetylglucosamine can be obtained by using the host cell. The antibody shows higher antibody-dependent cell-mediated cytotoxic activity against CCR4-expressing cells than a monoclonal antibody produced by a hybridoma derived from a non-human animal.

After introduction of the expression vector, transformants which express a humanized antibody stably are selected in accordance with the method disclosed in Japanese Published Unexamined Patent Application No. 257891/90, by culturing in a medium for animal cell culture containing an agent such as G418 sulfate (hereinafter referred to as "G418", manufactured by Sigma) or the like. Examples of the medium for animal cell culture include PRMI1640 medium (manufactured by Nissui Pharmaceutical), GIT medium (manufactured by Nissui Pharmaceutical), EX-CELL302 Medium™ (manufactured by JRH), IMDM medium (manufactured by GIBCO BRL), Hybridoma-SFM Medium™ (manufactured by GIBCO BRL), media obtained by adding various additives such as FCS to these media, and the like. The humanized antibody can be produced and accumulated in a culture medium by culturing the selected transformants in a medium. The expression amount and antigen binding activity of the humanized antibody in the culture medium can be measured by ELISA or the like. Also, in the transformant, the expression amount of the humanized antibody can be increased by using dhfr amplification system or the like according to the method disclosed in Japanese Published Unexamined Patent Application No. 257891/90.

The humanized antibody can be purified from the culture medium of the transformant by using a protein A column (*Antibodies, A Laboratory Manual*, Cold Spring Harbor Laboratory, Chapter 8 (1988), *Monoclonal Antibodies: Principles and Practice*, Academic Press Limited (1996)). Any other conventional methods for protein purification can be used. For example, the humanized antibody can be purified by a combination of gel filtration, ion-exchange chromatography, ultrafiltration and the like. The molecular weight of the H chain or the L chain of the purified humanized antibody or the antibody molecule as a whole is determined by polyacrylamide gel electrophoresis (hereinafter referred to as "SDS-PAGE") [*Nature*, 227: 680 (1970)], Western blotting (*Antibodies, A Laboratory Manual*, Cold Spring Harbor Laboratory, Chapter 12 (1988), *Monoclonal Antibodies: Principles and Practice*, Academic Press Limited (1996)), and the like.

(9) Evaluation of Activity of Humanized Antibody

The binding reactivity to an antigen and the binding activity to a CCR4-expressing cell line of the purified humanized antibody can be determined by ELISA, an immunofluorescent method (*Cancer Immuno Immunother.*, 36: 373 (1993)). The cytotoxic activity against an antigen positive culture cell line can be evaluated by measuring the CDC activity, the ADCC activity or the like (*Cancer Immunol. Immunother.*, 36: 373 (1993)).

3. Method for Detecting and Determining CCR4 Using Anti-CCR4-Antibody

The present invention relates to a method for immunologically detecting and determining CCR4 or a cell expressing CCR4 on the surface thereof using the antibody of the present invention.

The method for immunologically detecting and determining CCR4 or a cell expressing CCR4 on the surface thereof using the antibody of the present invention include an immunofluorescent method, an enzyme-linked immunosorbent assay (ELISA), a radioactive material labeled immunoassay (RIA), an immunohitsochemical staining method such as an immunocyte staining method, an immunotissue staining method, or the like (ABC method, CSA method, etc.), the above enzyme immunoassay, a sandwich ELISA (*Monoclonal Antibody Experiment Manual* (published by Kodansha Scientific, 1987), *Second Series Biochemical Experiment Course*, Vol. 5, *Immunobiochemistry Research Method*, published by Tokyo Kagaku Dojin (1986)).

The immunofluorescent method comprises reacting a separated cell, tissue, or the like with the antibody of the present invention, reacting the reactant with an anti-immunoglobulin antibody or binding fragment labeled with a fluorescence substance such as fluorescein isothiocyanate (FITC) or the like, and then measuring the fluorescence substance with a flow cytometer.

The enzyme-linked immunosorbent assay (ELISA) comprises reacting a separated cell or crushing solution thereof, tissue or crushing solution thereof, cell culture supernatant, serum, preural fluid, ascites fluid, ocular fluid or the like with the antibody of the present invention, reacting the reactant with an anti-immunoglobulin antibody or binding fragment labeled with an enzyme such as peroxydase, biotin, or the like, and then measuring the resultant developed dye with an absorption photometer.

The radioactive material labeled immunoassay (RIA) comprises reacting a separated cell or crushing solution thereof, tissue or crushing solution thereof, cell culture supernatant, serum, preural fluid, ascites fluid, ocular fluid or the like with the antibody of the present invention, further reacting the reactant with an anti-immunoglobulin antibody or binding fragment labeled with radioisotope, and then measuring the radioactivity with a scintillation counter or the like.

The immunocyte staining and immunotissue staining methods comprise reacting a separated cell, tissue or the like with the antibody of the present invention, reacting the reactant with an anti-immunoglobulin antibody or binding fragment labeled with a fluorescence substance such as fluorescein isothiocyanate (FITC) or the like, or an enzyme such as peroxydase, biotin or the like, and then observing the cell, tissue or the like with a microscope.

The sandwich ELISA is a method which comprises adsorbing, on a plate, one of two antibodies having a different epitope among the antibodies of the present invention; labeling another antibody with a fluorescence substance such as FITC or the like, or an enzyme such as peroxydase, biotin or the like; reacting a separated cell or crushing solution thereof, tissue or crushing solution thereof, cell culture supernatant, serum, preural fluid, ascites fluid, ocular fluid, or the like with the antibody-adsorbing plate; and then reacting it with the labeled antibody for carrying out a reaction according to the labeled substance.

4. Diagnosis and Treatment of Th2-Mediated Immune Disease or Cancer

Since the humanized antibody of the present invention specifically binds to CCR4 which is expressed on a cultured cell line and shows cytotoxic activity such as CDC activity, ADCC activity and the like, it will be useful in diagnosing and treating Th2-mediated diseases and the like. Also, since the proportion of amino acid sequences derived from human antibody in the humanized antibody is higher than that in antibodies of a non-human animal, it is expected that it shows strong cytotoxic activity in the human body, it does not show immunogenicity, and its effects continues for a long time.

In addition, the production of Th2 cytokines which are produced by cells such as IL-4, IL-5, IL-13 and the like, can be inhibited by administering the antibody of the present invention to cells or tissues of an experimental subject.

The Th2 cell used in the present invention is preferably activated Th2 cell or memory Th2 cell. Specific examples include cells having CD45RA− and CD4+ properties.

The cytotoxic activities of the recombinant antibody of the present invention are generated, e.g., when the antibody of the present invention binds to a Th2 cell to thereby induce apoptosis in the cell. Also, the cell can be obstructed and depleted by inducing apoptosis.

Also, examples of the method for diagnosing Th2-mediated immune diseases or cancers include a method in which a human CCR4 positive cell existing in cells or tissues of an experimental subject is immunologically detected as described above.

Furthermore, the antibody of the present invention can be used as a diagnostic agent for Th2-mediated immune diseases or cancers, or diseases in which the morbid states advance due to abnormal increase or decrease of Th2 cells.

Moreover, since the antibody of the present invention can reduce or deplete CCR4-expressing cells by its cytotoxic activity, it can provide a diagnostic method or therapeutic method for Th2-mediated immune diseases or cancers, which uses the antibody of the present invention, and therapeutic and preventive agents for Th2-mediated immune diseases or cancers, which comprises the antibody of the present invention as an active ingredient.

The Th2-mediated immune diseases include, irrespective of slight or serious, inflammatory diseases such as acute or chronic airway hypersensitivity or bronchial asthma, atopic skin diseases including atopic dermatitis, allergic rhinitis, pollinosis, and the like; diseases caused by inflammation competent cells such as eosinophil, mast cell and the like which can be propagated or activated by cytokine and chemokine released from Th2 cells, biologically functional molecules such as IgE and the like which are produced by cytokine and chemokine released from Th2 cells, and the like; and immune diseases in which the morbid states advance due to abnormal changes in Th2 cells.

The antibody of the present invention can be administered alone, but it is generally preferred to provide it in the form of a pharmaceutical formulation produced by mixing it with at least one pharmaceutically acceptable carrier in accordance with a method well known in the technical field of pharmaceutics.

It is preferred to select a route of administration which is the most effective in carrying out the intended treatment such as oral administration or parenteral administration, e.g., intraoral administration, tracheal administration, rectal administration, subcutaneous injection, intramuscular injection, intravenous injection, and the like. Intravenous injection is preferred in an antibody or peptide formulation.

The dosage form includes sprays, capsules, tablets, granules, syrups, emulsions, suppositories, injections, ointments, tapes, and the like.

Examples of formulation suitable for oral administration include emulsions, syrups, capsules, tablets, powders, granules, and the like.

Liquid preparations such as emulsions and syrups, can be produced using additives such as water; saccharides, e.g., sucrose, sorbitol, fructose, etc.; glycols, e.g., polyethylene glycol, propylene glycol, etc.; oils, e.g., sesame oil, olive oil, soybean oil, etc.; antiseptics, e.g., p-hydroxybenzoate, etc.; flavors, e.g., strawberry flavor, peppermint, etc.; and the like.

Capsules, tablets, powders, granules and the like can be produced using additives such as fillers, e.g., lactose, glucose, sucrose, mannitol, etc.; disintegrating agents, e.g., starch, sodium alginate, etc.; lubricants, e.g., magnesium stearate, etc.; binders, e.g., polyvinyl alcohol, hydroxypropylcellulose, gelatin, etc.; surfactants, e.g., fatty acid esters, etc.; plasticizers, e.g., glycerine, etc.; and the like.

Examples of formulations suitable for parenteral administration include injections, suppositories, sprays, and the like.

Injections can be prepared using a carrier such as a salt solution, glucose solution or a mixture thereof, or the like.

Suppositories can be prepared using a carrier such as cacao butter, hydrogenated fat, a carboxylic acid, or the like.

Also, sprays can be prepared from the antibody or peptide itself or using a carrier or the like which does not stimulate oral and airway mucous membranes of patients and can facilitate absorption of the antibody or peptide by dispersing it as minute particles.

Examples of the carrier include lactose, glycerine, and the like. Depending on the properties of the antibody or peptide and the carrier to be used, aerosols, dry powders and the like can be produced. The additives exemplified in the oral preparations can also be added to the parenteral preparations.

The dose and frequency of administration vary depending on intended therapeutic effect, administration method, treating period, age, body weight and the like, but the dose is generally from 10 μg/kg to 8 mg/kg per day per adult.

As discussed above, according to the present invention, a recombinant antibody and an antibody fragment thereof, which binds specifically to human CCR4 and contains novel CDRs for CCR4, are provided. The antibody of the present invention is useful for the immunological detection of a human Th2 cell by immunocyte staining and for the diagnosis or treatment of all Th2-mediated immune diseases including bronchial asthma and atopic skin diseases, diseases in which the morbid states advance due to abnormal balance of Th2 cells and cancers including blood cancers such as leukemia.

Examples of the present invention are shown below, but the present invention is not limited thereto.

EXAMPLE 1

Production of hybridoma cell which produces mouse anti-CCR4 monoclonal antibody:

Hybridoma cells which produce mouse anti-CCR4 monoclonal antibody KM2160 (*Int. Immunol.*, 11: 81 (1999)) were produced according to the following procedure.

(1) Preparation of Antigen

The amino acid sequence (SEQ ID NO:17) of human CCR4 (hereinafter referred to as "hCCR4") protein was analyzed by using Genetyx Mac™, and Compound 1 (SEQ ID NO:1) was selected as a partial sequence considered to be appropriate as the antigen among portions having high hydrophilicity, N-terminal and C-terminal. Also, a portion of the amino acid sequence of a mouse CCR4 (hereinafter referred to as "mCCR4") (*BBRC*, 218: 337 (1996)) protein corresponding to Compound 1 was selected as Compound 2 (SEQ ID NO:2). SEQ ID NOs:1 and 2 correspond to positions 2-29 from the N-terminal amino acids of human CCR4 and mouse CCR4, respectively.

Abbreviations of the amino acids and their protecting groups used in the present invention were used according to the recommendation by IUPAC-IUB Joint Commission on Biochemical Nomenclature (*European Journal of Biochemistry*, 138: 9 (1984)).

Unless otherwise indicated, the following abbreviations represent the following amino acids.

Ala: L-Alanine

Asn: L-Asparagine

Asp: L-Aspartic acid

Asx: L-Aspartic acid or L-asparagine

Cys: L-Cysteine

Gln: L-Glutamine

Glu: L-Glutamic acid

Glx: L-Glutamic acid or L-glutamine

Gly: Glycine

Ile: L-Isoleucine

Leu: L-Leucine

Lys: L-Lysine

Met: L-Methionine

Phe: L-Phenylalanine

Pro: L-Proline

Ser: L-Serine

Thr: L-Threonine

Tyr: L-Tyrosine

Val: L-Valine

The following abbreviations represent protecting groups of corresponding amino acids and side chain-protecting amino acids.

Fmoc: 9-Fluorenylmethyloxycarbonyl tBu: t-Butyl

Trt: Trityl

Boc: t-Butyloxycarbonyl

Fmoc-Thr(tBu)-OH:
Nα-9-Fluorenylmethyloxycarbonyl-O-t-butyl-L-threonine

Fmoc-Ser(tBu)-OH:
Nα-9-Fluorenylmethyloxycarbonyl-O-t-butyl-L-serine

Fmoc-Tyr(tBu)-OH:
Nα-9-Fluorenylmethyloxycarbonyl-O-t-butyl-L-tyrosine

Fmoc-Lys(Boc)-OH:
Nα-9-Fluorenylmethyloxycarbonyl-Nε-t-butyloxycarbonyl-L-lysine Fmoc-Asn(Trt)-OH:
Nα-9-Fluorenylmethyloxycarbonyl-Nγ-trityl-L-asparagine Fmoc-Gln(Trt)-OH:
Nα-9-Fluorenylmethyloxycarbonyl-Nδ-trityl-L-glutamine Fmoc-Asp(OtBu)-OH:
Nα-9-Fluorenylmethyloxycarbonyl-L-aspartic acid β-t-butyl ester Fmoc-Glu(OtBu)-OH:
Nα-9-Fluorenylmethyloxycarbonyl-L-glutamic acid γ-t-butyl ester Fmoc-Cys(Trt)-OH:
Nα-9-Fluorenylmethyloxycarbonyl-5-trityl-L-cysteine The following abbreviations represent corresponding reaction solvents and reaction reagents.

PyBOP: Benzotriazol-1-yloxytripyrrolidinophosphonium hexafluorophosphate
HOBt: N-Hydroxybenzotriazole
DMF: N,N-Dimethylformamide
DCM: Dichloromethane
TFA: Trifluoroacetic acid
NMM: N-Methylmorpholine
DTT: Dithiothreitol (i) Synthesis of Compound 1 (SEQ ID NO:1) (H-Asn-Pro-Thr-Asp-Ile-Ala-Asp-Thr-Thr-Leu-Asp-Glu-Ser-Ile-Tyr-Ser-Asn-Tyr-Tyr-Leu-Tyr-Glu-Ser-Ile-Pro-Lys-Pro-Cys-OH)

Into a reaction vessel of an automatic synthesizer (manufactured by Shimadzu), 30 mg of a carrier resin (chlorotrityl resin, manufactured by AnaSpec) to which 16.8 μmol of H-Cys(Trt) had been bound was placed, 1 ml of DCM/DMF (1:1) was added thereto, followed by stirring for 10 minutes, the solution was drained away, 1 ml of DMF was further added, followed by stirring for 1 minute, the solution was drained away, and then the following procedure was carried out in accordance with the synthesis program provided by Shimadzu.

(a) Fmoc-Pro-OH (168 μmol), PyBOP (168 μmol), HOBt·1H$_2$O (168 μmol) and NMM (252 μmol) were stirred in DMF (588.2 μl) for 5 minutes, the resulting solution was added to the resin, followed by stirring for 60 minutes, and then the solution was drained away.

(b) The carrier resin was washed for 1 minute with 707 μl of DMF, and this step was repeated 5 times. In this way, Fmoc-Pro-Cys(Trt) was synthesized on the carrier.

Next, the following Fmoc group-deprotection steps were carried out.

(c) 707 μl of 30% piperidine-DMF solution was added, followed by stirring for 4 minutes, and then the solution was drained away, and this procedure was repeated again.

(d) The carrier resin was washed for 1 minute with 707 μl of DMF and then the solution was drained away, and this step was repeated 5 times.

In this way, the carrier resin to which the Fmoc group-eliminated H-Pro-Cys(Trt) had been bound was obtained.

Next, a condensation reaction was carried out in the step (a) using Fmoc-Lys(Boc)-OH, and then H-Lys(Boc)-Pro-Cys(Trt) was synthesized on the carrier via the washing step of (b) and deprotection steps of (c) and (d). Next, the steps (a) to (d) were repeated by using Fmoc-Pro-OH, Fmoc-Ile-OH, Fmoc-Ser(tBu)-OH, Fmoc-Glu(OtBu)-OH, Fmoc-Tyr(tBu)-OH, Fmoc-Leu-OH, Fmoc-Tyr(tBu)-OH and Fmoc-Tyr(tBu)-OH in this order in the step (a). Next, the condensation reaction of step (a) was carried out using Fmoc-Asn(Trt)-OH, the washing step of (b) was carried out, the condensation reaction of step (a) using Fmoc-Asn(Trt)-OH and the washing step of (b) were repeated and then the deprotection steps of (c) and (d) were carried out. Subsequently, the steps (a) to (d) were repeated by using Fmoc-Ser(tBu)-OH, Fmoc-Tyr(tBu)-OH, Fmoc-Ile-OH, Fmoc-Ser(tBu)-OH, Fmoc-Glu(OtBu)-OH and Fmoc-Asp(OtBu)-OH in this order. Next, the condensation reaction of step (a) was carried out using Fmoc-Leu-OH, the washing step of (b) was carried out, the condensation reaction of step (a) using Fmoc-Leu-OH and the washing step of (b) were repeated and then the deprotection steps of (c) and (d) were carried out. Thereafter, the condensation reaction steps of (a) and (b) were repeated twice by using Fmoc-Thr(tBu)-OH, Fmoc-Thr(tBu)-OH, Fmoc-Asp(OtBu)-OH, Fmoc-Ala-OH, Fmoc-Ile-OH, Fmoc-Asp(OtBu)-OH, Fmoc-Thr(tBu)-OH, Fmoc-Pro-OH and Fmoc-Asn(Trt)-OH in that order in the step (a) and the deprotection steps of (c) and (d) were carried out, and then, after repetition of a series of these steps, the mixture was washed with methanol and butyl ether in this order and dried under a reduced pressure for 12 hours to obtain the carrier resin to which a side chain-protected peptide had been bound. A mixed solution (1 ml) of TFA (90%), thioanisole (5%) and 1,2-ethanedithiol (5%) was added thereto, and incubated at room temperature for 2 hours to thereby remove the side chain protecting groups and simultaneously cutting out the peptide from the resin. After removing the resin by filtration, about 10 ml of ether was added to the resulting solution, and the thus formed precipitate was recovered by centrifugation and decantation and dried under a reduced pressure to obtain 63.7 mg of crude peptide. The crude product was dissolved in 2 ml of DMF in the presence of 60 mg of DTT and then purified by HPLC using a reverse phase column (CAPCELL PAK C18™, 30 mm I.D.×25 mm, manufactured by Shiseido). Elution was carried out according to a linear density gradient method in which 90% acetonitrile aqueous solution containing 0.1% TFA was added to 0.1% TFA aqueous solution and detecting at 220 nm was carried out to obtain a fraction containing Compound 1. After freeze-drying of this fraction, 2.5 mg of Compound 1 was obtained.

Mass spectrometry (FAB MS): m/z=3227.5 (M+H$^+$)

Amino acid analysis: Asx 4.8 (5), Glx 2.7 (2), Ser 3.1 (3), Thr 2.0 (3), Ala 1.1 (1), Pro 3.1 (3), Tyr 3.8 (4), Leu 2.2 (2), Lys 1.2 (1), Ile 3.0 (3), Cys 1.2 (1)

(ii) Synthesis of compound 2 (SEQ ID NO:2) (H-Asn-Ala-Thr-Glu-Val-Thr-Asp-Thr-Thr-Gln-Asp-Glu-Thr-Val-Tyr-Asn-Ser-Tyr-Tyr-Phe-Tyr-Glu-Ser-Met-Pro-Lys-Pro-Cys-OH)

Using 50 mg of a carrier resin (chlorotrityl resin, manufactured by AnaSpec) to which 28.0 μmol of H-Cys(Trt) had been bound as the starting material, the steps (a) to (d) were repeated by using Fmoc-Pro-OH, Fmoc-Lys(Boc)-OH, Fmoc-Pro-OH, Fmoc-Met-OH, Fmoc-Ser(tBu)-OH, Fmoc-Glu(OtBu)-OH, Fmoc-Tyr(tBu)-OH, Fmoc-Phe-OH, Fmoc-Tyr(tBu)-OH and Fmoc-Tyr(tBu)-OH in this order in the step (a) in the same manner as in (i). Next, the condensation reaction of step (a) was carried out using Fmoc-Ser(tBu)-OH, the washing step of (b) was carried out, the condensation reaction of step (a) using Fmoc-Ser(tBu)-OH and the washing step of (b) were repeated and then the deprotection steps of (c) and (d) were carried out. Next, the condensation reaction of step (a) was carried out using Fmoc-Asn(Trt)-OH, the washing step of (b) was carried out, the condensation reaction of step (a) using Fmoc-Asn(Trt)-OH and the washing step of (b) were repeated and then the deprotection steps of (c) and (d) were carried out. Subsequently, the steps (a) to (d) were repeated by using Fmoc-Tyr(tBu)-OH, Fmoc-Val-OH, Fmoc-Thr(tBu)-OH, Fmoc-Glu(tBu)-OH, Fmoc-Glu(OtBu)-OH and Fmoc-Asp(OtBu)-OH in that order. Next, the condensation reaction of step (a) was carried out using Fmoc-Gln(Trt)-OH, the washing step of (b) was carried out, the condensation reaction of step (a) using Fmoc-Gln(Trt)-OH and the washing step of (b) were again repeated and then the deprotection steps of (c) and (d) were carried out. Thereafter, the condensation reaction steps of (a) and (b) were repeated twice by using Fmoc-Thr(tBu)-OH, Fmoc-Thr(tBu)-OH, Fmoc-Asp(OtBu)-OH, Fmoc-Thr(tBu)-OH, Fmoc-Val-OH, Fmoc-Glu(OtBu)-OH, Fmoc-Thr(tBu)-OH, Fmoc-Ala-OH and Fmoc-Asn(Trt)-OH in this order in the step (a) and the deprotection steps of (c) and (d) were carried out, and then, after repetition of a series of these steps, the mixture was washed and dried to obtain the carrier resin to which a side chain-protected peptide was bound. A crude peptide (96.3 mg) was obtained by eliminating the side chain protecting groups and cutting out the peptide from the resin in the same manner as in (i), and further purified by HPLC using a reverse phase column to obtain 5.8 mg of Compound 2.

Mass spectrometry (TOFMS): m/z=3297.7 (M+H$^+$)

Amino acid analysis: Asx 4.1 (4), Glx 4.3 (4), Ser 2.0 (2), Thr 4.6 (5), Ala 1.0 (1), Pro 2.2 (2), Tyr 3.9 (4), Val 1.9 (2), Met 1.0 (1), Phe 1.0 (1), Lys 1.1 (1), Cys 1.1 (1)

(2) Preparation of Immunogen

The hCCR4 partial peptide obtained in Example 1(1) was used as the immunogen after preparing its conjugate with KLH (Calbiochem) by the following method in order to increase its immunogenicity. That is, KLH was dissolved in PBS to obtain 10 mg/ml, and 1/10 volume of 25 mg/ml MBS (Nakalai Tesque) was added dropwise thereto, followed by stirring for 30 minutes. Free MBS was removed by a gel filtration column such as Sephadex G-25 column which had been equilibrated in advance with PBS or the like, and 2.5 mg of the resulting KLH-MB was mixed with 1 mg of the peptide dissolved in 0.1 M sodium phosphate buffer (pH 7.0), followed by stirring at room temperature for 3 hours. After the reaction, the mixture was dialyzed against PBS.

(3) Immunization of Animal and Production of Antibody Producing Cells

To 5-weeks-old female mice (Balb/c), 100 μg of the peptide-KLH conjugate prepared in Example 1(2) was administered together with 2 mg of aluminum gel and 1×10$^9$ cells of pertussis vaccine (manufactured by Chiba Serum Institute), and 2 weeks thereafter, 100 μg of the conjugate was administered once a week at a total of 4 times. A blood sample was taken from each animal from the venous plexus of the fundus of the eye, its serum titer was examined by an enzyme immunoassay described below, and the spleen was excised 3 days after the final immunization from a mouse which showed a sufficient antibody titer. The spleen was excised from a mouse on the 3rd day after the final administration and cut to pieces in MEM (manufactured by Nissui Pharmaceutical), and cells were unbound using a pair of forceps and centrifuged (1,200 rpm, 5 minutes), the supernatant was removed, followed by treatment with 3 ml of a Tris-ammonium chloride buffer (pH 7.65) for 1 to 2 minutes to eliminate erythrocytes. The remaining cells were further washed three times with MEM and used for cell fusion.

(4) Preparation of Mouse Myeloma Cell

An 8-azaguanine-resistant mouse myeloma cell line, P3X63Ag8U.1 (ATCC CRL-1597, hereinafter referred to as "P3-U1"), was cultured and used as the parent line in cell fusion.

(5) Preparation of Hybridoma Cells

The spleen cells and myeloma cells obtained in Example 1(3) and (4) were mixed to a ratio of 10:1, followed by centrifuging (1,200 rpm, 5 minutes) to remove the supernatant, 0.5 ml of a polyethylene glycol solution (a solution containing 2 g of polyethylene glycol-1000, 2 ml of MEM and 0.7 ml of DMSO) was added to the thus precipitated cells per 10$^8$ of spleen cells under conditions of 37° C., followed by thoroughly suspending. Thereafter, 1 to 2 ml of MEM was added several times at 1 to 2 minute intervals, and the final volume was adjusted to 50 ml with MEM. After removing the supernatant by centrifugation (900 rpm, 5 minutes), the precipitate was suspended in 100 ml of HAT medium, dispensed in 100 μl/well into a 96 well microtiter plate (manufactured by Sumitomo Bakelite), followed by culturing in a 5% CO$_2$ incubator at 37° C. for 10 to 14 days. Using wells in which propagation of the fused cell was observed, binding activity for the hCCR4 partial peptide (compound 1) in the culture supernatant was measured by the ELISA described in 2(3) of Example 2. Each well in which the activity was confirmed was cloned by a total of 2 times of limiting dilution, once by changing the medium to the HT medium and then changing the medium to the normal medium. In this way, a hybridoma cell KM2160 which produces the mouse antibody KM2160 was obtained. As shown in FIG. 1, KM2160 specifically reacted with the hCCR4 partial peptide (Compound 1).

Transformant clone KM2160 was received on Aug. 12, 2004 by the International Patent Organism Depository, National Institute of Advanced Industrial Science and Technology, AIST Tsukuba Central 6, 1-1, Higashi 1-chome Tsukuba-shi, Ibaraki-ken 305-8566 Japan, and accorded Accession Number FERM BP-10090.

EXAMPLE 2

Preparation of anti-CCR4 chimeric antibody:

1. Isolation and analysis of cDNA encoding the V region of anti-CCR4 mouse antibody:

(1) Preparation of mRNA from hybridoma cells which produces anti-CCR4 mouse antibody A mRNA was prepared from the hybridoma cell KM2160 described in Example 1. About 48 μg of mRNA was prepared from 8×10$^7$ cells of the hybridoma cell KM2160 using a mRNA preparation kit, Fast Track mRNA Isolation Kit™ (manufactured by Invitrogen) according to the manufacture's instructions.

(2) Production of H Chain and L Chain cDNA Library of Anti-CCR4 Mouse Antibody cDNA having EcoRI-NotI adapters on both termini was synthesized from 5 μg of the KM2160 mRNA obtained in 1(1) of Example 2 using cDNA Synthesis kit (manufactured by Amersham Pharmacia Biotech) according to the manufacture's instructions. The thus prepared cDNA was dissolved in 20 µl of sterile water and fractionated by agarose gel electrophoresis, and about 1.5 kb cDNA fragments corresponding to the H chain of IgG type antibody and about 1.0 kb cDNA fragments corresponding to the L chain of κ type were respectively recovered using QIAquick Gel Extraction Kit™ (manufactured by QIAGEN). Next, using λZAPII Predigested EcoRI/CIAP-Treated Vector Kit (manufactured by Stratagene), each of 0.1 µg of the about 1.5 kb cDNA fragments and 0.1 µg of the about 1.0 kb cDNA fragments was linked to 1 µg of the λZAPII vector which had been digested with a restriction enzyme EcoRI and terminus-dephosphorylated with Calf Intestine Alkaline Phosphatase according to the manufacture's instructions. A 2.5 µl portion of each reaction solution after the ligation was packaged into λ phage using GigapackIII Gold Packaging Extract™ (manufactured by Stratagene) according to the manufacture's instructions, and then *Escherichia coli* line XL1-Blue (*Biotechniques*, 5: 376 (1987)) was infected with an appropriate amount of the phage to obtain $9.3 \times 10^4$ of phage clones as the H chain cDNA library of KM2160 and $7.4 \times 10^4$ of phage clones as the L chain cDNA library. Thereafter, each phage was fixed on a nylon membrane filter Hybond-N+™ (manufactured by Amersham Pharmacia Biotech) according to the manufacture's instructions.

(3) Cloning of H Chain and L Chain cDNAs of Anti-CCR4 Mouse Antibody

Using ECL Direct Nucleic Acid Labeling and Detection System™ (manufactured by Amersham Pharmacia Biotech), according to the manufacture's instructions, clones on the nylon membrane filters of the KM2160H chain cDNA library and L chain cDNA library prepared in 1(2) of Example 2 were detected using cDNA of the C region of a mouse antibody (H chain is a BamHI-EcoRI fragment of mouse Cγ1 cDNA (*EMBO J.*, 3: 2047 (1984)), L chain is a HpaI-EcoRI fragment of Cκ cDNA (*Cell*, 22: 197 (1980)) as the probe, and phage clones strongly bound to the probe were obtained as 10 clones for each of the H chain and the L chain. Next, each phage clone was converted into plasmid by the in vivo excision method using λZAPII Cloning Kit™ according to the manufacture's instructions (manufactured by Stratagene). Using BigDye Terminator Cycle Sequencing FS Ready Reaction Kit™ (manufactured by PE Biosystems), the nucleotide sequence of cDNA contained in each plasmid obtained in this manner was analyzed by a DNA sequencer ABI PRISM 377™ of the same manufacturer according to the manufacture's instructions. As a result, a plasmid pKM2160H4 containing a full length functional H chain cDNA and a plasmid pKM2160L6 containing a full length L chain cDNA, in which an ATG sequence considered to be the initiation codon is present in the 5'-end of cDNA, were obtained.

(4) Analysis of Amino Acid Sequence of V Region of Anti-CCR4 Mouse Antibody

A full nucleotide sequence of the H chain V region contained in the plasmid pKM2160H4, a full amino acid sequence of the H chain V region deduced therefrom, a full nucleotide sequence of the L chain V region contained in the plasmid pKM2160L6 and a full amino acid sequence of the L chain V region deduced therefrom are shown in SEQ ID NOs:3, 15, 4 and 16, respectively. Also, there are many nucleotide sequences which correspond to the amino acid sequences represented by SEQ ID NOs:15 and 16 other than those represented SEQ ID NOs:3 and 4, and all of them are included within the scope of the present invention. Based on the comparison with sequence data of known mouse antibodies (*Sequences of Proteins of Immunological Interest*, US Dept. Health and Human Services (1991)) and the comparison with the results of analysis of the H chain and L chain N-terminal amino acid sequences of the purified anti-CCR4 mouse antibody KM2160 carried out using a protein sequencer (PPSQ-10, manufactured by Shimadzu), it was found that each cDNA thus isolated is a full length cDNA which encodes the anti-CCR4 mouse antibody KM2160 containing secretory signal sequences which are amino acids of positions 1-19 in the amino acid sequence shown in SEQ ID NO:15 in the H chain and amino acids of positions 1-19 in the amino acid sequence shown in SEQ ID NO:16 in the L chain.

Next, novelty of the amino acid sequences of the V regions of H chain and L chain of the anti-CCR4 mouse antibody KM2160 was examined. Using GCG Package™ (version 9.1, manufactured by Genetics Computer Group) as the sequence analyzing system, amino acid sequence data base of known proteins were searched by BLAST method (*Nucleic Acids Res.*, 25: 3389 (1997)). As a result, completely coincided sequences were not found for both of the H chain and L chain, so that it was confirmed that the H chain V region and L chain V region of the anti-CCR4 mouse antibody KM2160 are novel amino acid sequences.

Also, CDRs of the H chain V region and L chain V region of the anti-CCR4 mouse antibody KM2160 were identified by comparing with amino acid sequences of known antibodies. Amino acid sequences of CDR1, CDR2 and CDR3 in the H chain V region of the anti-CCR4 mouse antibody KM2160 are shown in SEQ ID NOs:5, 6 and 7, respectively, and amino acid sequences of CDR1, CDR2 and CDR3 in the L chain V region in SEQ ID NOs:8, 9 and 10, respectively.

2. Stable Expression of Anti-CCR4 Chimeric Antibody Using Animal Cell (1) Construction of Anti-CCR4 Chimeric Antibody Expression Vector pKANTEX2160

An anti-CCR4 chimeric antibody expression vector pKANTEX2160 was constructed as follows, using a humanized antibody expression vector pKANTEX93 which expresses a human IgG1 and κ type antibody and the plasmids pKM2160H4 and pKM2160L6 obtained in 1(3) of Example 2.

A synthetic DNA having the nucleotide sequences shown in SEQ ID NOs:11 and 12 was designed in order to obtain the H chain V region cDNA of KM2160 by PCR, and another synthetic DNA having the nucleotide sequences shown in SEQ ID NOs:13 and 14 for obtaining the L chain V region cDNA. Each synthetic DNA contains a restriction enzyme recognizing sequence in its 5'-end for its cloning into pKANTEX93, and synthesis of the DNA was entrusted to Genset Inc. The plasmid pKM2160H4 (20 ng) obtained in 1(3) of Example 2 was added to a buffer containing 50 µl of PCR Buffer #1 attached to KOD DNA Polymerase (manufactured by TOYOBO), 0.2 mM dNTPs, 1 mM magnesium chloride and 0.5 µM of the synthetic DNA having the nucleotide sequences represented by SEQ ID NOs:11 and 12, and the mixture was heated at 94° C. for 3 minutes. After 2.5 units of KOD DNA Polymerase (manufactured by TOYOBO) were added, the mixture was subjected to 25 cycles of the reaction each cycle including heating at 94° C. for 30 seconds, at 58° C. for 30 seconds and at 74° C. for 1 minute, using a DNA thermal cycler GeneAmp PCR System 9600 (manufactured by PERKIN ELMER). In the same manner, 20 ng of the plasmid pKM2160L6 obtained in 1(3) of Example 2 was added to a buffer containing 50 µl of PCR Buffer #1 attached to KOD DNA Polymerase (manufactured by TOYOBO), 0.2 mM dNTPs, 1 mM magnesium chloride and 0.5 µM of the synthetic DNA having the nucleotide sequences represented by SEQ ID NOs:13 and 14, and PCR was carried out in the same manner as described above. The reaction solution (10 μl) was subjected to agarose gel electrophoresis, and then an H chain V region PCR product of about 0.46 kb and an L chain V region PCR product of about 0.43 kb were each recovered using QIAquick Gel Extraction Kit (manufactured by QIAGEN).

Figure 2:
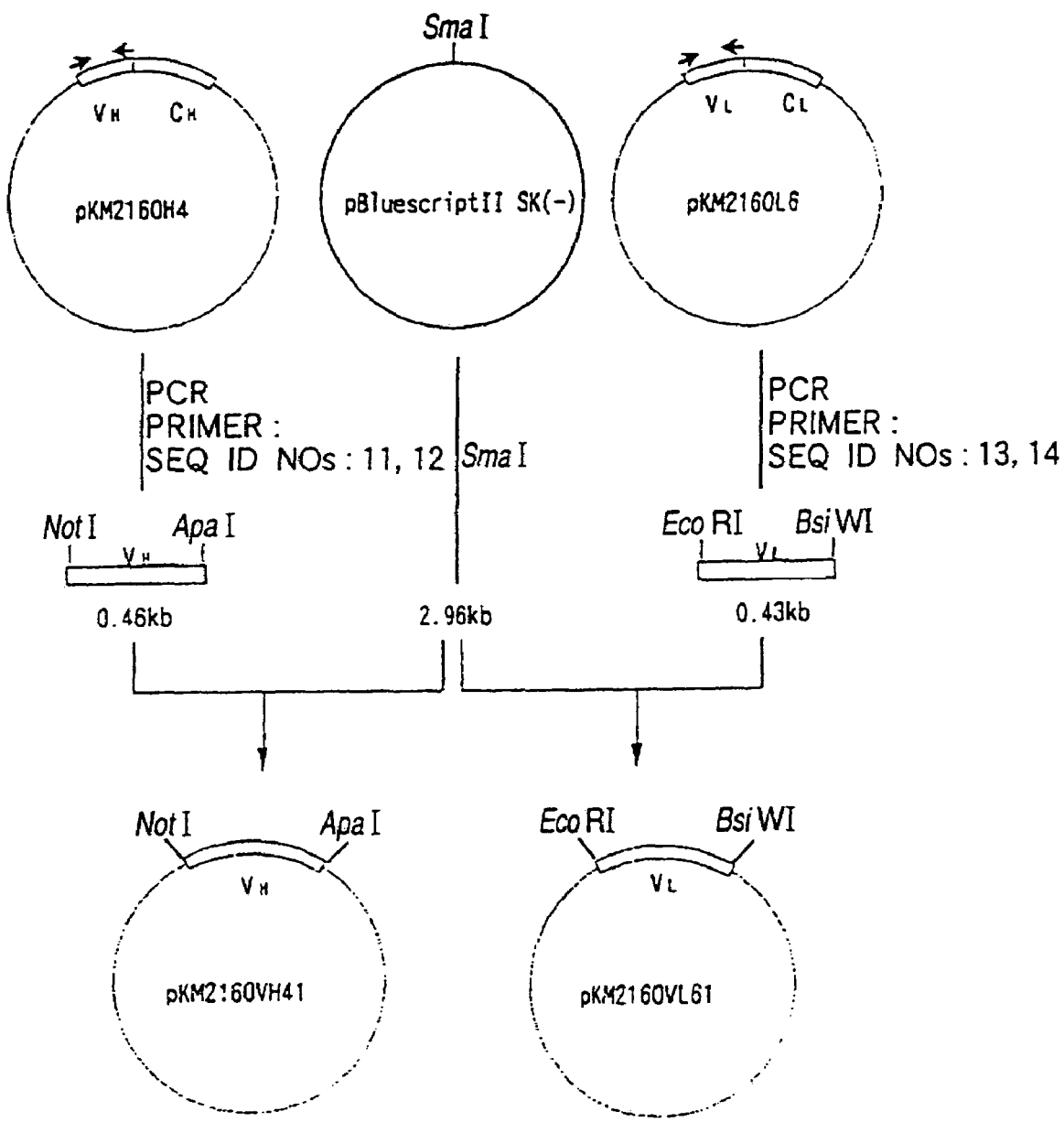
FIG. 2 is a drawing showing construction steps of plasmids pKM2160VH41 and pKM2160VL61.

Next, 0.1 μg of DNA obtained by digesting a plasmid pBluescript SK(−)™ (manufactured by Stratagene) with a restriction enzyme SmaI (manufactured by Takara Shuzo) and about 0.1 μg of each of the PCR products obtained above were added to give 7.5 μl in final volume of sterile water, and 7.5 μl of the solution I of TAKARA DNA Ligation Kit Ver. 2™ (manufactured by Takara Shuzo) and 0.3 μl of a restriction enzyme SmaI were added thereto, and the mixture was allowed to react at 22° C. overnight. Using the resulting recombinant plasmid DNA solution, E. coli DH5α (manufactured by TOYOBO) was transformed. Each plasmid DNA was prepared from the transformant clones and subjected to the reaction using BigDye Terminator Cycle Sequencing FS Ready Reaction Kit™ (manufactured by PE Biosystems) according to the manufacture's instructions, and the nucleotide sequence was analyzed by a DNA sequencer ABI PRISM 377™ of the same manufacturer. Thus, the plasmids pKM2160VH41 and pKM2160VL61 shown in FIG. 2 having the desired nucleotide sequences were obtained.

Figure 3:
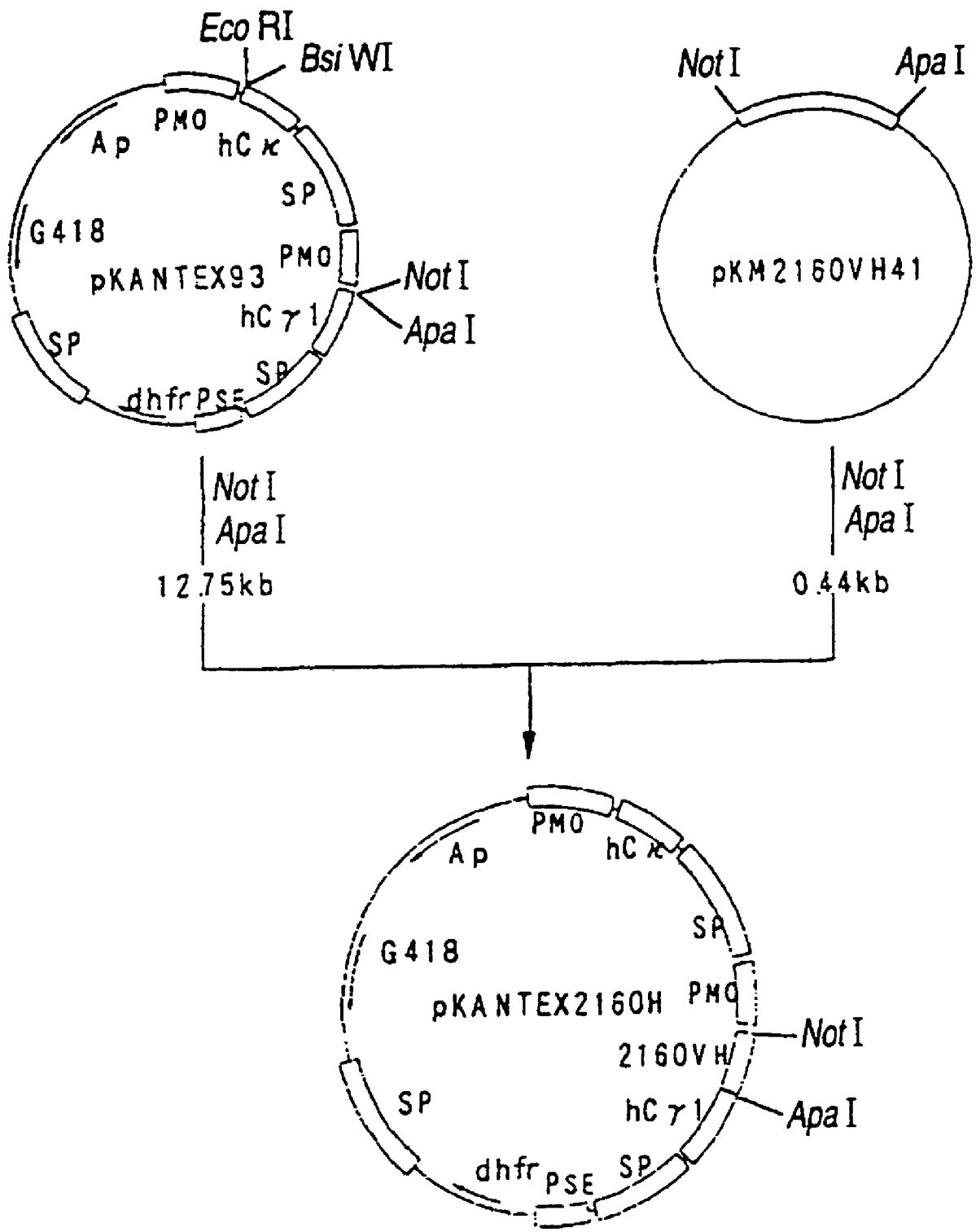
FIG. 3 is a drawing showing construction step of a plasmid pKANTEX2160H.

Next, 3 μg of the humanized antibody expression vector pKANTEX93 and 3 μg of the pKM2160VH41 obtained above were added to a buffer containing 30 μl of 10 mM Tris-HCl (pH 7.5), 10 mM magnesium chloride and 1 mM DTT, 10 units of a restriction enzyme ApaI (manufactured by Takara Shuzo) were added thereto, and the mixture was allowed to react at 37° C. for 1 hour. The reaction solution was subjected to ethanol precipitation, and the resulting precipitate was added to a buffer containing 10 μl of 50 mM Tris-HCl (pH 7.5), 100 mM sodium chloride, 10 mM magnesium chloride, 1 mM DTT, 100 μg/ml BSA and 0.01% Triton X-100, 10 units of a restriction enzyme NotI (manufactured by Takara Shuzo) were added thereto, and the mixture was allowed to react at 37° C. for 1 hour. The reaction mixture was fractionated by agarose gel electrophoresis, and about 12.75 kb and about 0.44 kb ApaI-NotI fragments of pKANTEX93 and pKM2160VH41, respectively, were recovered. The thus obtained two fragments were linked using TAKARA DNA Ligation Kit Ver. 2™ according to the manufacture's instructions, and E. coli DH5α (manufactured by TOYOBO) was transformed using the resulting recombinant plasmid DNA solution. Each plasmid DNA was prepared from the transformant clones and confirmed by a restriction enzyme treatment to thereby obtain a plasmid pKANTEX2160H shown in FIG. 3, in which about 0.44 kb of the desired ApaI-NotI fragment had been inserted.

Figure 4:
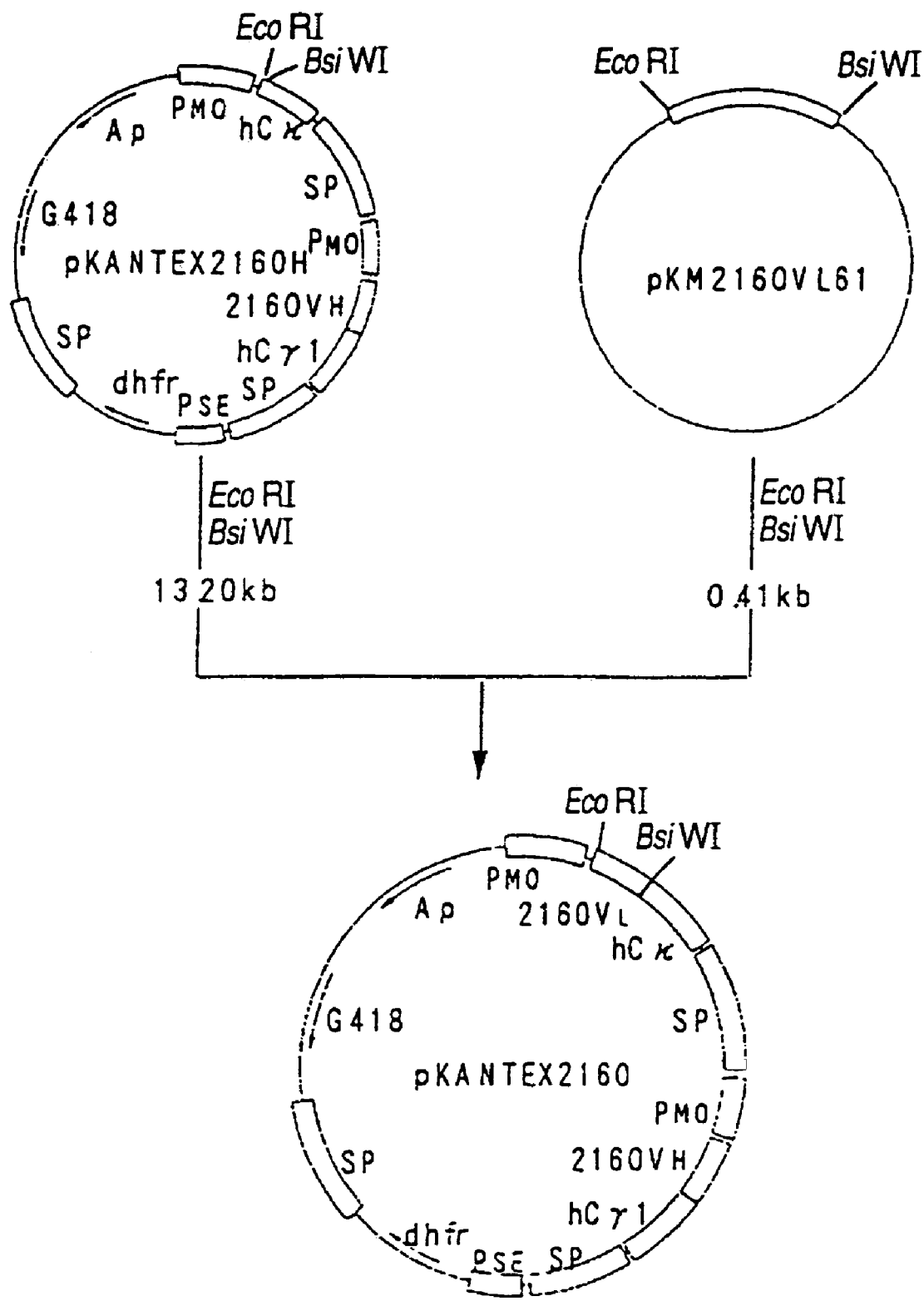
FIG. 4 is a drawing showing construction step of a plasmid pKANTEX2160.

Next, 3 μg of the pKANTEX2160H and 3 μg of the pKM2160VL61 obtained above were added to a buffer containing 50 mM Tris-HCl (pH 7.5), 100 mM sodium chloride, 10 mM magnesium chloride, 1 mM DTT and 100 μg/ml of BSA, the solution was adjusted to give a total volume of 30 μl, 10 units of a restriction enzyme BsiWI (manufactured by New England Biolabs) was added thereto, and the mixture was allowed to react at 55° C. for 1 hour. Then, a restriction enzyme EcoRI (manufactured by Takara Shuzo) was added thereto, and the mixture was allowed to react at 37° C. for 1 hour. The reaction mixture was fractionated by agarose gel electrophoresis, and about 13.20 kb and about 0.41 kb EcoRI-BsiWI fragments of pKANTEX2160H and pKM2160VL61, respectively, were recovered. The thus obtained two fragments were linked using TAKARA DNA Ligation Kit Ver. 2™ according to the manufacture's instructions, and E. coli DH5α (manufactured by TOYOBO) was transformed using the resulting recombinant plasmid DNA solution. Each plasmid DNA was prepared from the transformant clones and confirmed by a restriction enzyme treatment to thereby obtain a plasmid pKANTEX2160 shown in FIG. 4, in which about 0.41 kb of the desired EcoRI-BsiWI fragment had been inserted. When the plasmid was subjected to the reaction using BigDye Terminator Cycle Sequencing FS Ready Reaction Kit™ (manufactured by PE Biosystems) according to the manufacture's instructions, and the nucleotide sequence was analyzed by a DNA sequencer ABI PRISM 377™ of the same manufacturer, it was confirmed that the desired plasmid into which cDNA encoding the KM2160H chain and L chain V regions had been cloned was obtained.

(2) Stable Expression of Anti-CCR4 Chimeric Antibody Using Animal Cell

The anti-CCR4 chimeric antibody was expressed in animal cells as described below using the anti-CCR4 chimeric antibody expression vector pKANTEX2160 obtained in 2(1) of Example 2.

The plasmid pKANTEX2160 was converted into a linear form by digesting with a restriction enzyme AatII (manufactured by TOYOBO) and 10 μg thereof was introduced into $4 \times 10^6$ cells of rat myeloma cell line YB2/0 (ATCC CRL1662) by electroporation (Cytotechnology, 3: 133 (1990)), and the cells were suspended in 40 ml of H-SFM (manufactured by GIBCO-BRL) medium (supplemented with 5% FCS) and dispensed in 200 μl/well into a 96 well microtiter plate (manufactured by Sumitomo Bakelite). Twenty-four hours after incubation at 37° C. in a 5% $CO_2$ incubator, G418 was added to give a concentration of 1 mg/ml, followed by culturing for 1 to 2 weeks. A culture supernatant was recovered from a well in which a colony of G418-resistant transformant appeared and became confluent, and antigen-binding activity of the anti-CCR4 chimeric antibody in the supernatant was measured by ELISA shown in 2(3) of Example 2 (a peroxidase-labeled goat anti-human IgG(γ) antibody was used as the secondary antibody).

In order to increase the expressed amount of the antibody using a dhfr gene amplification system, the transformant in a well where expression of the anti-CCR4 chimeric antibody was found in the culture supernatant was suspended to give a density of 1 to $2 \times 10^5$ cells/ml in H-SFM medium containing 1 mg/ml G418 and 50 nM methotrexate (hereinafter referred to as "MTX": manufactured by Sigma) which is the inhibitor of a dhfr gene product dihydrofolate reductase (hereinafter referred to as "DHFR"), and the suspension was dispensed in 1 ml into wells of a 24 well plate (manufactured by Greiner). The mixture was cultured at 37° C. for 1 to 2 weeks in a 5% $CO_2$ incubator, so that a transformant showing resistance to 50 nM MTX was induced. When the transformant became confluent in a well, antigen-binding activity of the anti-CCR4 chimeric antibody in the culture supernatant was measured by ELISA shown in 2(3) of Example 2. Regarding the transformants in wells where expression of the anti-CCR4 chimeric antibody was found in culture supernatants, the MTX concentration was increased to 100 nM and then to 200 nM in the same manner to finally obtain a transformant which can grow in H-SFM medium containing 1 mg/ml of G418 and 200 nM of MTX and can also highly express the anti-CCR4 chimeric antibody. The thus obtained transformant was subjected to single cell isolation (cloning) by two times of limited dilution assay, and a transformant clone having the highest anti-CCR4 chimeric antibody expression was named KM2760. The expressed amount of the anti-CCR4 chimeric antibody by KM2760 was about 5 μg/10⁶ cells/24 hours. In addition, the antibody H chain C region of KM2760 belongs to human IgG1 subclass. KM2760 has been internationally deposited as FERM BP-7054 on Feb. 24, 2000, in National Institute of Bioscience and Human Technology, Agency of Industrial Science and Technology, the Ministry of International Trade and Industry (present name: International Patent Organism Depositary, National Institute of Advanced Industrial Science and Technology) (Higashi 1-1-3, Tsukuba-shi, Ibaraki Prefecture, Japan).

(3) Measurement of Binding Activity of Antibody to CCR4 Partial Peptide (ELISA)

The hCCR4 partial peptide (Compound 1) obtained in Example 1(1) was conjugated with thyroglobulin (hereinafter referred to as "THY") and used as the antigen for the assay. The production method was as described in Example 1(2), except that 4-(N-maleimidomethyl)cyclohexane-1-carboxylic acid N-hydroxysuccinimide ester (SMCC, manufactured by Sigma) was used instead of MBS as the crosslinking agent. The conjugate prepared in the above manner was dispensed at 10 μg/ml and 50 μl/well into a 96 well plate for EIA (manufactured by Greiner) and adhered thereto by incubating it at 4° C. overnight. After washing with PBS, 1% BSA-containing PBS (hereinafter referred to as "1% BSA-PBS") was added at 100 μl/well, and the mixture was allowed to react at room temperature for 1 hour to block the remaining active groups. After removing 1% BSA-PBS, diluted solutions of a transformant culture supernatant, a purified mouse antibody or a purified human chimeric antibody was dispensed at 50 μl/well, and the mixture was allowed to react at room temperature for 1 hour. After the reaction, each well was washed with 0.05% Tween 20-containing PBS (hereinafter referred to as "Tween-PBS"), a peroxidase-labeled rabbit anti-mouse Ig antibody solution (manufactured by DAKO) diluted 400 times with 1% BSA-PBS and a peroxidase-labeled goat anti-human IgG(γ) antibody solution (manufactured by American Qualex) diluted 3,000 times with 1% BSA-PBS were dispensed into the mouse antibody-added wells and the human chimeric antibody-added wells, respectively, as the secondary antibody solution at 50 μl/well, and the mixture was allowed to react at room temperature for 1 hour. After the reaction, each well was washed with Tween-PBS, ABTS solution (a solution prepared by dissolving 0.55 g of 2,2'-azino-bis(3-ethylbenzothiazoline-6-sulfonic acid)ammonium in 1 liter of 0.1 M citrate buffer (pH 4.2), and adding 1 μl/ml of hydrogen peroxide just before use) was dispensed at 50 μl/well for color developing, and the absorbance at 415 nm (hereinafter referred to as "$OD_{415}$") was measured.

(4) Purification of Anti-CCR4 Chimeric Antibody from Culture Medium

Figure 5:
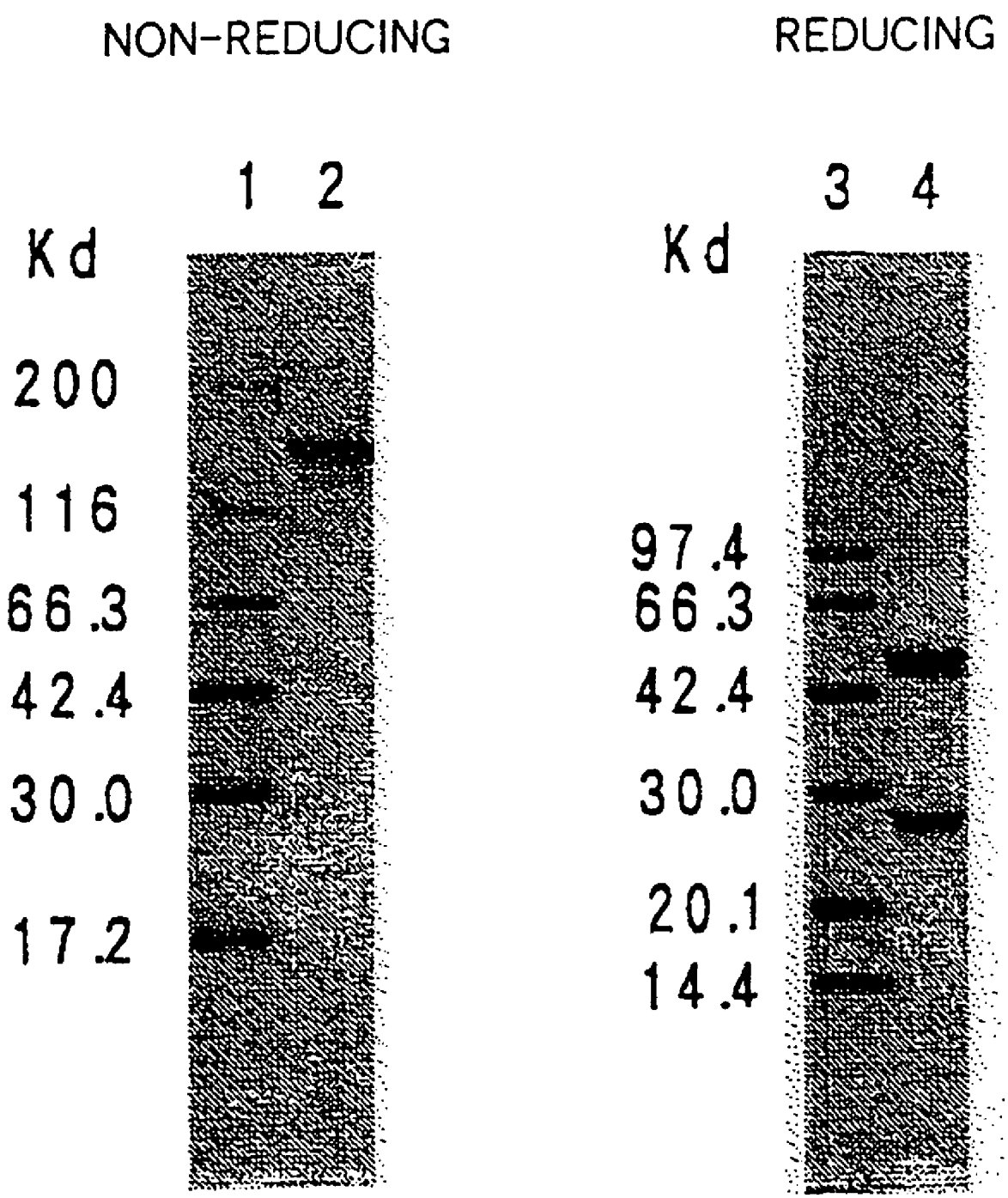
FIG. 5 is a drawing showing an SDS-PAGE (5 to 20% gradient gel) electrophoresis pattern of purified anti-CCR4 chimeric antibody KM2760. The left side shows a result of electrophoresis carried out under non-reducing conditions, and the right side under reducing conditions. Lanes 1, 2, 3 and 4 show electrophoresis patterns of high molecular weight markers, KM2760, low molecular weight markers and KM2760, respectively.

The transformant cell clone KM2760 which expresses the anti-CCR4 chimeric antibody obtained in 2(2) of Example 2 was suspended in H-SFM (manufactured by GIBCO-BRL) containing 200 nM MTX and 5% Daigo's GF21 (manufactured by Wako Pure Chemical Industries) to give a density of 1 to 2×10⁵ cells/ml, and dispensed at 100 ml into 175 cm² flasks (manufactured by Greiner). The cells were cultured at 37° C. for 5 to 7 days in a 5% CO₂ incubator, and the culture medium was recovered when they became confluent. The anti-CCR4 chimeric antibody KM2760 was purified from about 200 ml of the culture supernatant using Prosep-A™ (manufactured by Bioprocessing) column according to the manufacture's instructions to thereby obtain about 1.9 mg of the purified protein. About 3 μg of the resulting anti-CCR4 chimeric antibody KM2760 was applied to electrophoresis according to the known method (*Nature*, 227: 680 (1970)) to examine its molecular weight and purification degree. The results are shown in FIG. 5. As shown in FIG. 5, the purified anti-CCR4 chimeric antibody KM2760 was about 150 kilodaltons (hereinafter referred to as "Kd") under non-reducing conditions, and two bands of about 50 Kd and about 25 Kd were observed under reducing conditions. The sizes of the proteins almost coincided with the molecular weights deduced from the cDNA nucleotide sequences of H chain and L chain of KM2760 (H chain: 49,226, L chain: 24,168) and also coincided with reports disclosing that IgG type antibody has a molecular weight of about 150 Kd under non-reducing conditions and is degraded into an H chain having a molecular weight of about 50 Kd and an L chain having a molecular weight of about 25 Kd under reducing conditions due to cutting of the intramolecular disulfide bond (hereinafter referred to as "S—S bond") (*Antibodies: A Laboratory Manual*, Cold Spring Harbor Laboratory, Chapter 14 (1988), *Monoclonal Antibodies: Principles and Practice*, Academic Press Limited (1996)), so that it was confirmed that the anti-CCR4 chimeric antibody KM2760 was expressed as the antibody molecule having a correct structure. Also, the N-terminal amino acid sequences of the H chain and L chain of the purified anti-CCR4 chimeric antibody KM2760 were analyzed using a protein sequencer (PPSQ-10, manufactured by Shimadzu), it was confirmed that they coincide with N-terminal amino acid sequences of the H chain and L chain of the anti-CCR4 mouse antibody KM2160.

3. Establishment of hCCR4-High-Expressing Cell (1) Construction of Expression Vector CAG-pcDNA3 for Animal Cell An expression vector was constructed as descried below by producing an expression vector (CAG-pcDNA3) in which the promoter region of an expression vector for animal cell, pcDNA3™ (manufactured by INVITROGEN), was changed from cytomegalovirus (CMV) promoter to CAG (AG (modified chicken β actin) promoter with CMV-IE enhancer), and inserting the CCR4 gene into the vector.

pcDNA3™ (5 μg) was allowed to react with a restriction enzyme NruI (manufactured by Takara Shuzo) at 37° C. for 1 hour, and then DNA fragments were recovered by ethanol precipitation. Next, they were allowed to react with a restriction enzyme HindIII (manufactured by Takara Shuzo) at 37° C. for 1 hour and then fractionated by agarose gel electrophoresis to recover a DNA fragment of about 5.8 kb containing no CMV promoter region. Plasmid CAG-pBluescript IIKS(+) (3 μg) having CAG promoter (*Nuc. Acid. Res.*, 23: 3816 (1995)) region was allowed to react with a restriction enzyme SalI (manufactured by Takara Shuzo) at 37° C. for 1 hour and then DNA fragments were recovered by ethanol precipitation. They were blunt-ended with DNA Blunting Kit (manufactured by Takara Shuzo), further allowed to react with HindIII at 37° C. for 1 hour, and then fractionated by agarose gel electrophoresis to recover a DNA fragment of about 1.8 kb containing the CAG promoter region. The thus recovered respective DNA fragments were ligated using DNA Ligation Kit (manufactured by Takara Shuzo), and *E. coli* DH5α was transformed using the resulting recombinant plasmid DNA to obtain plasmid CAG-pcDNA3.

(2) Construction of hCCR4 Expression Vector

An hCCR4 expression vector was constructed as described below by using the CAG-pcDNA3 obtained in 3(1) of Example 2 and hCCR4DNA-inserted pcDNA3 (CCR4/pcDNA3). Both of the CAG-pcDNA3 and CCR4/pcDNA3 were allowed to react with HindIII at 37° C. for 1 hour and DNA fragments were recovered by ethanol precipitation. Next, they were allowed to react with BglII (manufactured by Takara Shuzo) at 37° C. for 1 hour and then fractionated by agarose gel electrophoresis to recover a DNA fragment of about 2.0 kb containing the CAG promoter region and a DNA fragment of about 5.5 kb containing the hCCR4 gene region. Thereafter, plasmid CAG-CCR4/pcDNA3 was obtained using both of the DNA fragments in the same manner as in 3(1) of Example 2.

(3) Expression of hCCR4 in Animal Cell

The plasmid was introduced into animal cells by electroporation in the same manner as described in 2(2) of Example 2. EL-4 cells (ATCC TIB-39) were suspended in PBS(−) (manufactured by GIBCO-BRL) to give a density of $1\times10^7$ cells/500 µl, 10 µg of the CAG-CCR4/pcDNA3 obtained in 3(2) of Example 2 was added thereto, and the mixture was incubated in ice for 10 minutes and then put into a cuvette for exclusive use (manufactured by Bio-Rad) to carry out gene introduction at 260 V and 500 µFD. After the mixture was further incubated in ice for 10 minutes, the cells were suspended in 200 ml of 10% FCS-RPMI medium and dispensed at 200 µl/well into a 96 well plate for cell culturing. Twenty-four hours after culturing, 100 µl of the culture supernatant was removed from each well, and 10% FCS-RPMI medium containing 1 mg/ml of G418 was dispensed at 100 µl/well to give a final concentration of 0.5 mg/ml. Two weeks thereafter, single clones of between 10 and 100 were selected and cultured again.

(4) Selection of hCCR4-High-Expressing Cell

They were selected by an immunofluorescent method using KM2160 prepared in Example 1 (5). Into a 96 well U shape plate, $2\times10^5$ cells of each of selected several tens of the gene-introduced clones was dispensed. KM2160 labeled with biotin by a known method (*Enzyme Antibody Method*, published by Gakusai Kikaku) was diluted to 5 µg/ml with a buffer for FACS (1% BSA-PBS, 0.02% EDTA, 0.05% $NaN_3$, pH 7.4), human IgG (manufactured by Welfide) was diluted to 3.75 mg/ml to prevent nonspecific staining, each of the thus diluted antibody solution was dispensed at 200 µl/well, and the mixture was allowed to react in ice for 30 minutes. As a negative control, biotinylated anti-IL-5R antibody (WO 97/10354) was used at the same concentration. After washing twice with 200 µl/well of the buffer, streptoavidin-PE (manufactured by Becton Dickinson Japan) was dispensed at 20 µl/well. Thirty minutes after the reaction in ice in the dark, the cells were washed three times with 200 µl/well and finally suspended to 500 µl, and the fluorescence intensity was measured by a flow cytometer to select one cell line having the highest fluorescence intensity.

EXAMPLE 3

Analysis of function of anti-CCR4 chimeric antibody:

1. Evaluation of Activity of Anti-CCR4 Chimeric Antibody (1) Reactivity of Anti-CCR4 Chimeric Antibody for Human and Mouse CCR4 (ELISA)

Figure 6:
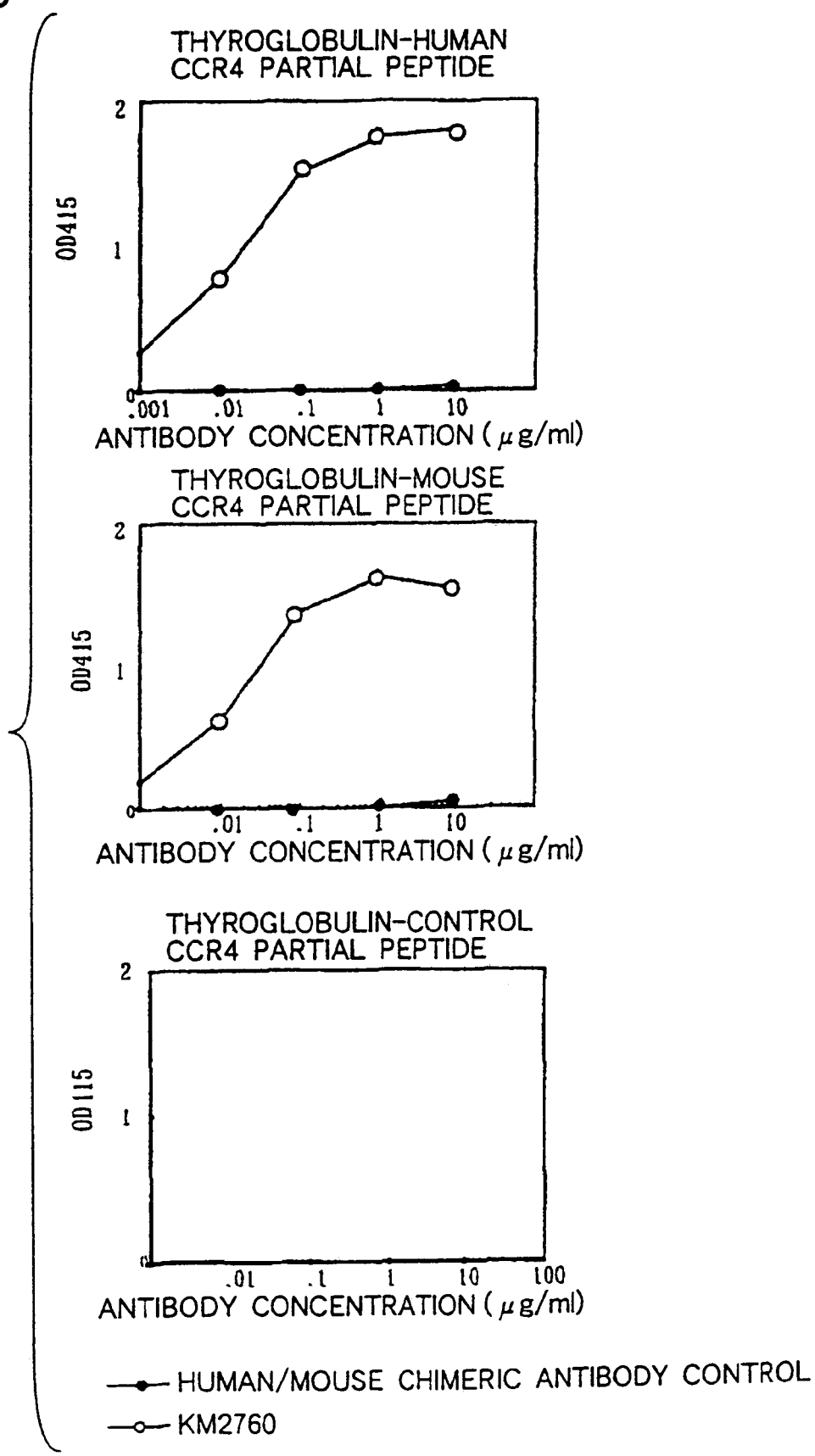
FIG. 6 is a drawing showing the activity of a purified anti-CCR4 chimeric antibody KM2760 to bind to a CCR4 partial peptide measured by changing the antibody concentration. The ordinate and abscissa represent the CCR4-binding activity and the antibody concentration, respectively.

Reactivity of the purified anti-CCR4 chimeric antibody KM2760 to human CCR4 and mouse CCR4 was measured by ELISA shown in 2(3) of Example 2. The hCCR4 partial peptide (Compound 1) and mCCR4 partial peptide (Compound 2) obtained in Example 1(2) were conjugated with THY and used as the antigen. The preparation was carried out in the same manner as in Example 1(2), except that SMCC (manufactured by Sigma) was used instead of MBS as the crosslinking agent. FIG. 6 shows a result of the examination of reactivity in which the CCR4 peptide conjugate to be adhered was fixed to each well of a ELISA plate to 10 µg/ml and 50 µl/well and the concentration of the anti-CCR4 chimeric antibody KM2760 to be added was changed. As shown in FIG. 6, the anti-CCR4 chimeric antibody KM2760 had almost binding activity to the hCCR4 partial peptide and mCCR4 partial peptide at a similar level. Based on this result, it was found that the anti-CCR4 chimeric antibody KM2760 recognizes the epitope existing in a region of positions 2-29 from the N-terminal amino acid of human CCR4 and mouse CCR4.

(2) Reactivity of Anti-CCR4 Chimeric Antibody with hCCR4-High-Expressing Cells (Immunofluorescent Method)

Figure 7:
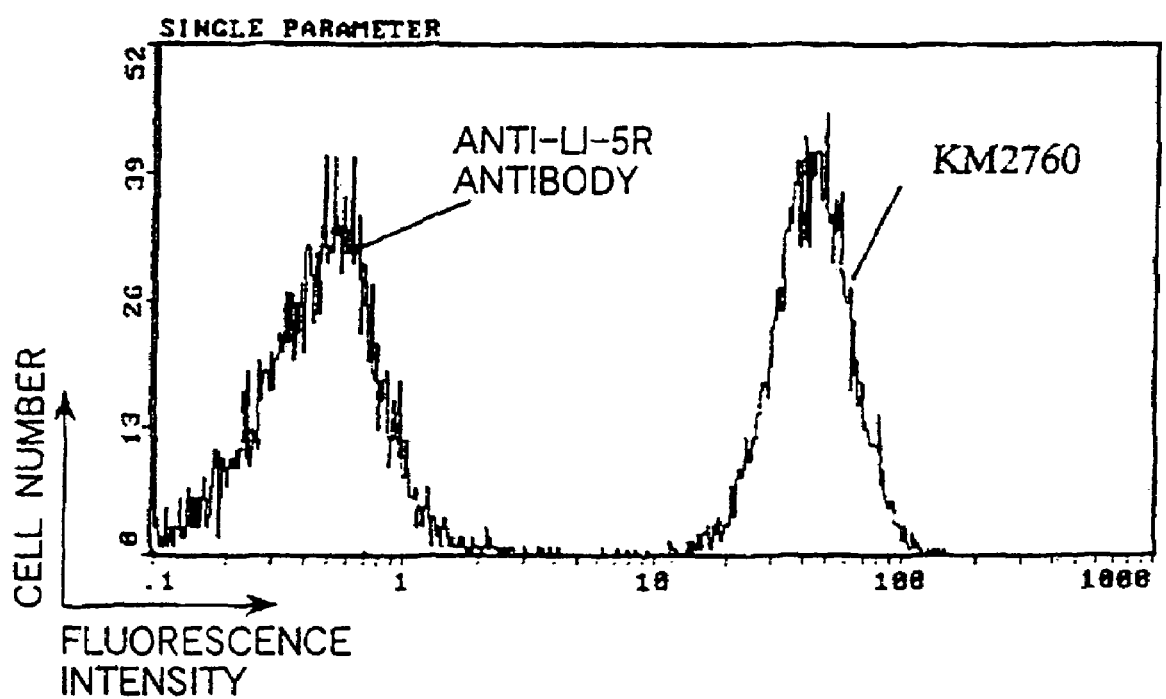
FIG. 7 is a drawing showing the reactivity of KM2760 with CCR4-high-expressing cells (CCR4/EL-4) measured by an immunofluorescence activating cell sorter.

Reactivity of the purified anti-CCR4 chimeric antibody KM2760 with the hCCR4-high-expressing cell (hereinafter referred to as "CCR4/EL-4") produced in 3(4) of Example 2 was measured in the same manner as in 3(4) of Example 2. As shown in FIG. 7, the anti-CCR4 chimeric antibody KM2760 showed strong reactivity with CCR4/EL-4 cells.

2. In Vitro Cytotoxic Activity of Anti-CCR4 Chimeric Antibody (ADCC Activity)

In order to evaluate in vitro cytotoxic activity of the purified CCR4 chimeric antibody obtained in 2(4) of Example 2, its ADCC activity was measured as described below.

(1) Preparation of Target Cell Suspension

The hCCR4-high-expressing cell CCR4/EL-4 obtained in 3(4) of Example 2 was cultured in 10% FCS-RPMI 1640 medium containing 0.5 mg/ml G418 to give a density of $1\times10^6$ cells/0.5 ml, 1.85 MBq equivalent of radioactive sodium chromate ($Na_2{}^{51}CrO_4$) (manufactured by Daiichi Pure Chemicals) was added thereto and the mixture was allowed to react at 37° C. for 1.5 hours to thereby isotope-label the cells. After the reaction, the cells were washed three times by their suspension in RPMI 1640 medium and centrifugation, re-suspended in the medium and then incubated in ice at 4° C. for 30 minutes to thereby spontaneously release the radioactive substance. After centrifugation, 5 ml of 10% FCS-RPMI 1640 medium was added thereto to give a density of $2\times10^5$ cells/ml, and the mixture was used as the target cell suspension.

(2) Preparation of Effector Cell Suspension

Healthy human peripheral blood (60 ml) was collected using a syringe containing 200 units (200 µl) of a heparin sodium injection (manufactured by Takeda Pharmaceutical). The entire amount was filled up to 120 ml by diluting it two times with the same volume of physiological saline (manufactured by Otsuka Pharmaceutical). Lymphoprep™ (manufactured by NYCOMED) was dispensed at 5 ml into 12 tubes of 15 ml capacity centrifugation tubes (manufactured by Sumitomo Bakelite), the diluted peripheral blood was overlayered thereon at 10 ml, and the mixture was centrifuged at room temperature and 800×g for 20 minutes. PBMC fractions between the blood plasma layer and the Lymphoprep™ layer were collected from all centrifugation tubes, suspended in 1% FCS-containing RPMI 1640 medium (manufactured by GIBCO) (hereinafter referred to as "1% FCS-RPMI"), washed twice by centrifugation at 400×g and 4° C. for 5 minutes and then re-suspended to give a density of $5\times10^6$ cells/ml to be used as the effector cells.

(3) Measurement of ADCC Activity

The target cell suspension prepared in 2(1) of Example 3 was dispensed at 50 µl ($1\times10^4$ cells/well) into wells of a 96 well U bottom plate (manufactured by Falcon). Next, the effector cell suspension prepared in 2(2) of Example 3 was dispensed at 100 μl (5×10$^5$ cells/well, the ratio of effector cells to target cells becomes 50:1). Subsequently, each anti-CCR4 chimeric antibody was added to give a final concentration of 0.01 to 10 μg/ml and the mixture was allowed to react at 37° C. for 4 hours. After the reaction, the plate was centrifuged and the amount of $^{51}$Cr in 100 μl of the supernatant in each well was measured by a γ-counter. The amount of the spontaneously dissociated $^{51}$Cr was calculated in the same manner as the above using the medium alone instead of the effector cell suspension and antibody solution and measuring the amount of $^{51}$Cr in the supernatant. The amount of the total dissociated $^{51}$Cr was calculated in the same manner as the above by adding the medium alone instead of the antibody solution, and 1 N hydrochloric acid instead of the effector cell suspension, and measuring the amount of $^{51}$Cr in the supernatant. The ADCC activity was calculated by the following equation:

$$\text{Cytotoxic activity (\%)} = \frac{(\text{amount of }^{51}\text{Cr in sample supernatant}) - (\text{amount of spontaneously released }^{51}\text{Cr})}{(\text{amount of total }^{51}\text{Cr}) - (\text{spontaneously released }^{51}\text{Cr})} \times 100$$

Figure 8:
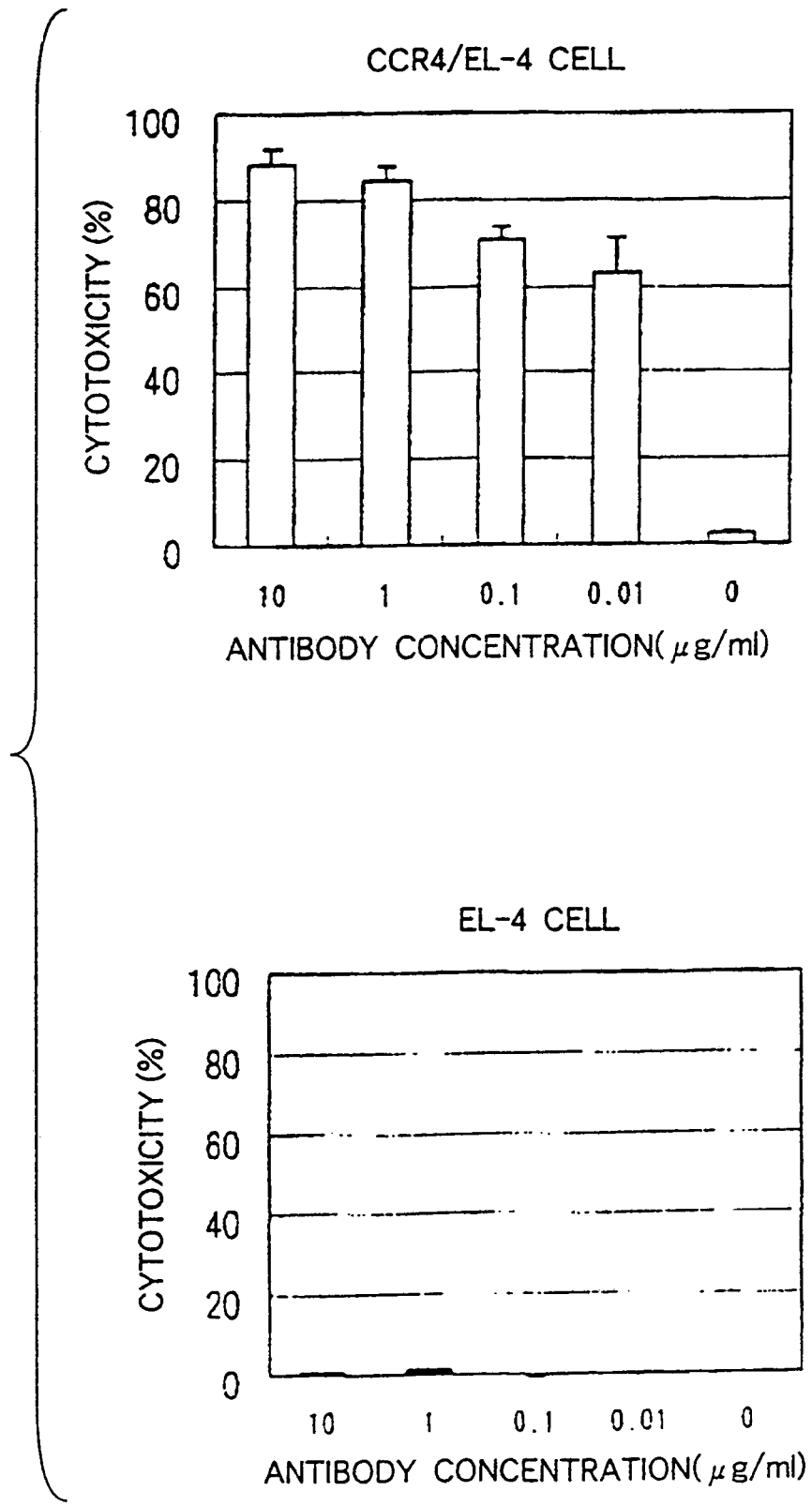
FIG. 8 is a drawing showing the cytotoxicity by ADCC activity for CCR4/EL-4 cells (upper graph) and EL-4 cells (lower graph).

The results are shown in FIG. 8. As shown in FIG. 8, the anti-CCR4 chimeric antibody showed strong cytotoxic activity antibody-concentration-dependently within a range of 0.01 to 10 μg/ml. When ADCC activity of a cell line into which no gene was incorporated, EL-4 cells, was measured in the same manner as a negative control, the activity was not found, so that it was confirmed that the cytotoxic activity is CCR4-specific. The above results show that the anti-CCR4 chimeric antibody KM2760 can reduce or deplete CCR4-expressed Th2 cells by efficiently activating human effector cells and therefore is useful for diagnosis or treatment of Th2-mediated immune diseases in human such as bronchial asthma, atopic skin inflammation, and the like.

EXAMPLE 4

Effect of anti-CCR4 chimeric antibody on human peripheral blood:

(1) Measurement of ADCC Activity on Human PBMC

Figure 9:
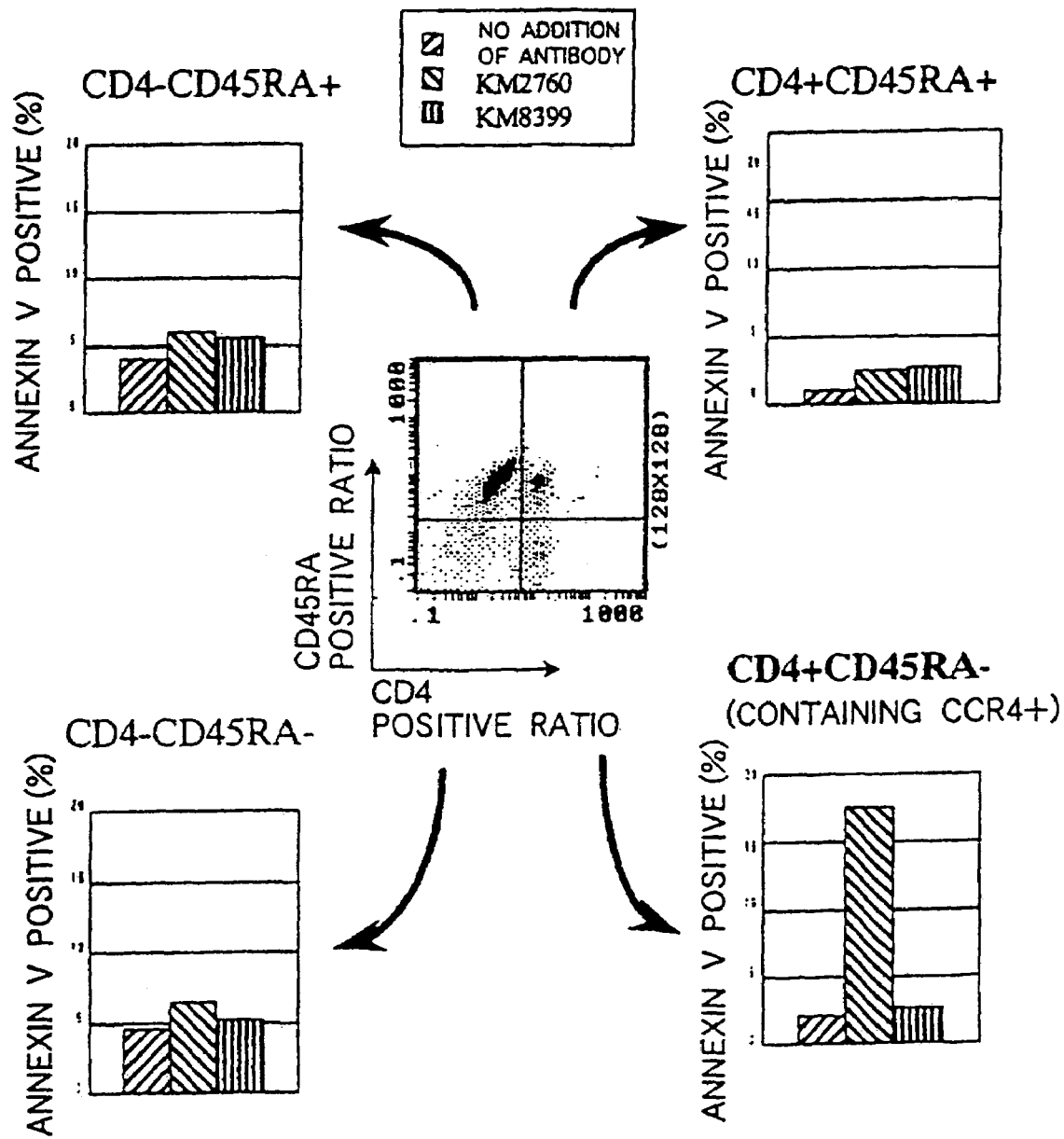
FIG. 9 is a drawing showing the cytotoxicity by ADCC activity for human PBMC, measured as annexin V positive ratio in 4 fractions having different staining abilities of CD4 and CD45RA.

PBMC was isolated in the same manner as in 2(2) of Example 3, and suspended to give a final density of 1×10$^7$ cells/ml. The mixture was dispensed at 100 μl/well into the U plate used in 2(3) of Example 3 to give a density of 1×10$^6$ cells/well. Each of KM2760 and a negative control anti-IL-5 receptor antibody (WO 97/10354) was diluted to give a concentration of 20 μg/ml and dispensed at 100 μl/well into the cell-dispensed wells. Twenty-four hours after culturing at 37° C. in a stream of 5% CO$_2$, the cells were recovered. The cytotoxicity was detected using Annexin V-EGFP Apoptosis Detection Kit™ (manufactured by MBL), and annexin V-positive cells were considered to be dead cells. The cells were centrifuged at 4° C. for 3 minutes at 400×g and suspended in the binding buffer attached to the kit to give a density of 5×10$^5$ cells/200 μl. The suspension was mixed with 1 μl of the Annexin V-EGFP reagent, followed by pipetting several times, and then the mixture was allowed to react for 5 minutes under shading. After the reaction, the mixture was centrifuged at 4° C. for 3 minutes at 400×g, and the supernatant was removed. The pellet was loosened by lightly stirring on a vortex mixer, 100 μl of 2.5 mM CaCl$_2$-containing methanol which had been cooled on ice was added thereto, and the mixture was incubated at 4° C. for 10 minutes. The mixture was centrifuged for 30 seconds at 8,000×g, and the supernatant was removed. The precipitate was suspended in 200 μl of the binding buffer and washed twice by centrifugation. To the remaining pellet after removing the supernatant, 10 μl of PC5-labeled anti-CD4 antibody (manufactured by Coulter), 20 μl of PE-labeled anti-CD45RA antibody (manufactured by Coulter) and 20 μl of FACS buffer containing 2.5 mM CaCl$_2$ were added, and the mixture was allowed to react at 4° C. for 30 minutes. Thereafter, the mixture was washed three times by centrifugation using the FACS buffer containing 2.5 mM CaCl$_2$ and analyzed by a flow cytometer (manufactured by Coulter). First, the group of cells was fractionated into 4 fractions (CD4+CD45RA+, CD4+CD45RA−, CD4−CD45RA+ and CD4−CD45RA−) based on the difference in staining properties between CD4 and CD45RA. Next, the annexin V-positive ratio in each fraction was measured and represented as cytotoxicity %. The results are shown in FIG. 9. The cytotoxicity of PBMC was observed only when co-cultured with KM2760, and the toxicity was detected specifically in the CD4+CD45RA− fraction to which CCR4-positive cells belong.

(2) Effect of Inhibiting Production of Cytokine from Human PBMC

In the same manner as described in 2(3) of Example 3, ADCC activity was induced by co-culturing PBMC and KM2760 (final concentration: 10 μg/ml) for 24 hours. After culturing, 100 μl of the supernatant was removed and 100 μl of a medium containing 1 μg/ml PMA (phorbol myristate acetate) and 200 ng/ml A23187 (calcimycin: manufactured by RBI) was added instead thereof, so that final concentrations of PMA and A23187 became 0.5 μg/ml and 100 ng/ml, respectively, and then the cytokine production was induced by stimulating the cells (Condition (i)). As another stimulation conditions, the cytokine production was induced using 50 ng/ml at a final concentration of an anti-CD3 antibody OKT-3 (ATCC CRL-8001) instead of A23187 (Condition (ii)). Each stimulating agent was introduced, and then, twenty-four hours after culturing, the culture supernatant was recovered to measure IL-4, IL-5, IL-13 and interferon (IFN)-γ using a cytokine measuring kit (manufactured by BioSource). As shown in FIG. 10, production of a Th2 cytokine IL-4, IL-5 or IL-13 was inhibited in the KM2760-added group, but production of a Th1 cytokine IFN-γ was not influenced.

EXAMPLE 5

Reactivity of anti-CCR4 chimeric antibody with human T cell leukemia cell line:

(1) Binding Ability to Membrane Surface (Immunofluorescent Method)

Figure 11:
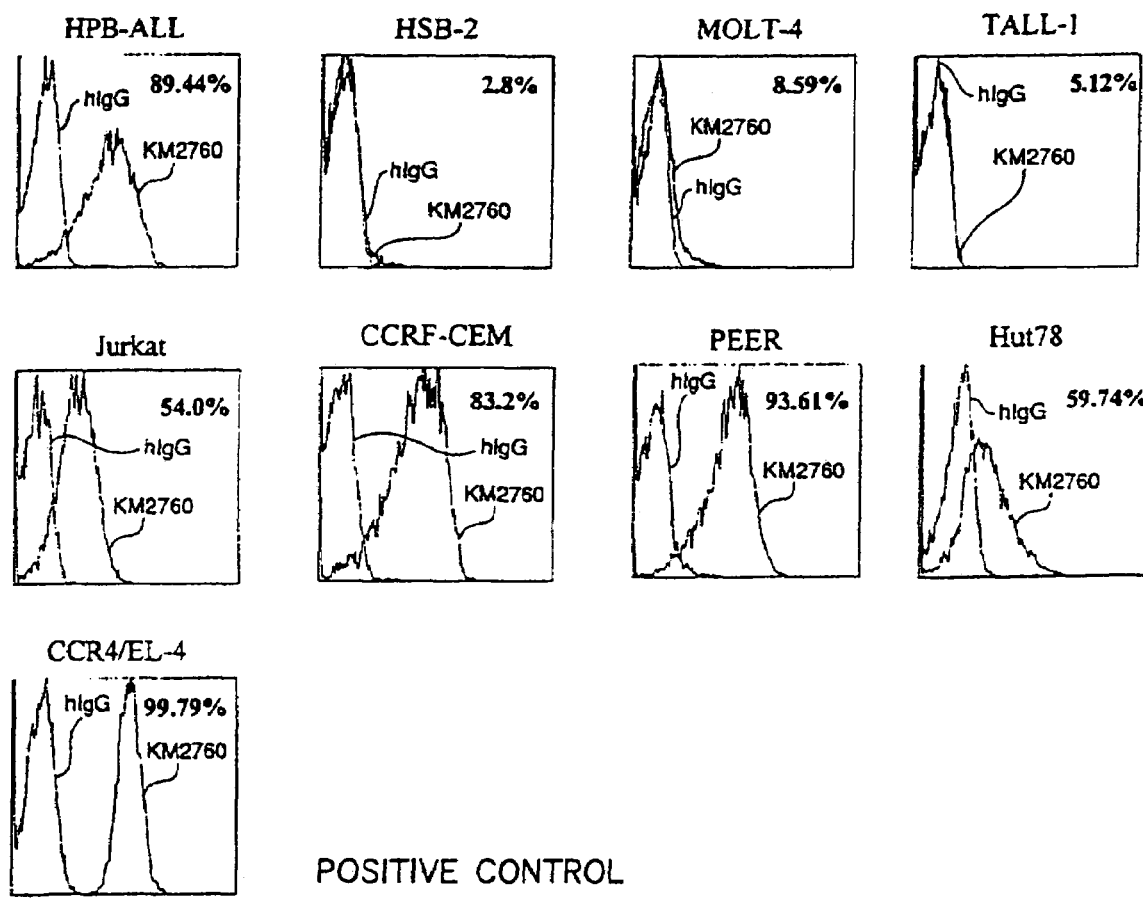
FIG. 11 is a drawing showing the reactivity of anti-CCR4 chimeric antibody KM2760 with human T cell leukemia cell lines.

Reactivity of the anti-CCR4 chimeric antibody KM2760 to the following 8 human T cell leukemia cell lines: HPB-ALL (*Cancer Research*, 54: 1511 (1994); acute T cell leukemia), HSB-2 (ATCC CCL-120.1; leukemia (T cell)), MOLT-4 (JCRB9031; lymphoma (T cell)), TALL-1 (JCRB 0086; leukemia (T cell)), Jurkat (ATCC TIB-152; acute T cell leukemia), CCRF-CEM (ATCC CCL-119; acute T cell leukemia), PEER (JCB 0830; leukemia (T cell)) and Hut78 (ATCC TIB-161; cutaneous T cell lymphoma), was measured in the same manner as in 3(4) of Example 2. In this case, the concentration of the biotinylated KM2760 was changed to 10 μg/ml. As shown in FIG. 11, the anti-CCR4 chimeric antibody KM2760 showed strong reactivity with 5 lines (HPB-ALL, Jurkat, CCRF-CEM, PEER and Hut78) among the 8 lines tested.

(2) ADCC Activity

Figure 12:
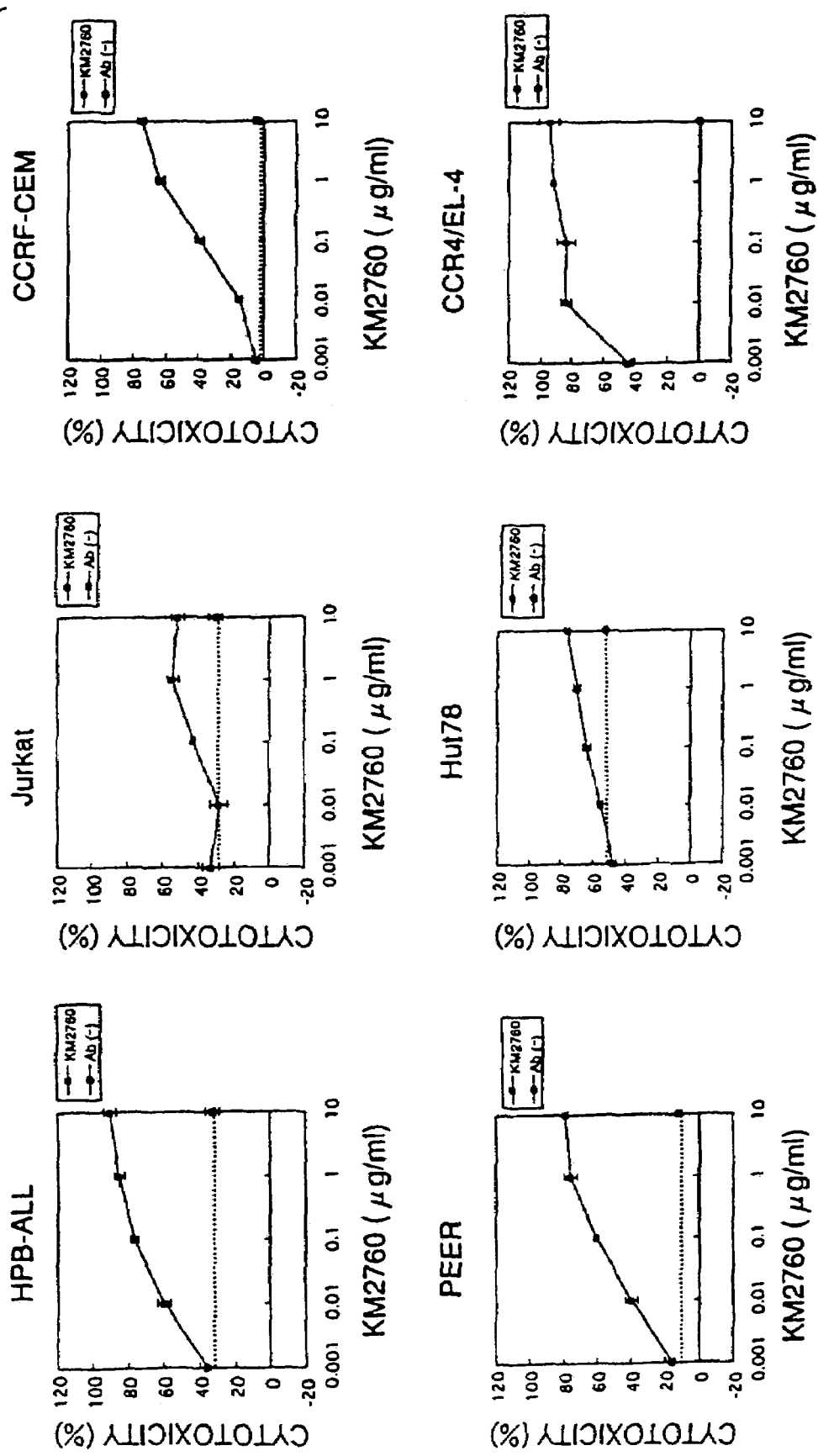
FIG. 12 is a drawing showing the cytotoxicity by anti-CCR4 chimeric antibody KM2760 for human T cell leukemia cell lines, which reactivity with anti-CCR4 chimeric antibody KM2760 was confirmed.

ADCC activity for the five cell lines whose reactivity with the anti-CCR4 chimeric antibody KM2760 had been confirmed in 1 of Example 5 was measured in the same manner as in 2 of Example 3. As shown in FIG. 12, the anti-CCR4 chimeric antibody KM2760 injured all of the tested cells concentration-dependently.

EXAMPLE 6

Evaluation of in vivo activity of anti-CCR4 chimeric antibody KM2760 (inhibition of Th2 cytokine production):

In order to evaluate in vivo activity of the purified anti-CCR4 chimeric antibody KM2760 obtained in 2(4) of Example 2, the antibody was administered to *Macaca fascicularis* by single intravenous injection and blood samples were periodically collected for about 1 month, cytokine production was induced in the peripheral leukocytes by stimulation with PMA (Phorbol 12-Myristate 13-Acetate, manufactured by Sigma) and IONOMYCIN™ (manufactured by Sigma), and Th2 cytokines, IL-4 and IL-13, and Th1 cytokine, IFN-γ, were measured. The methods and results are described below.

Figure 13:
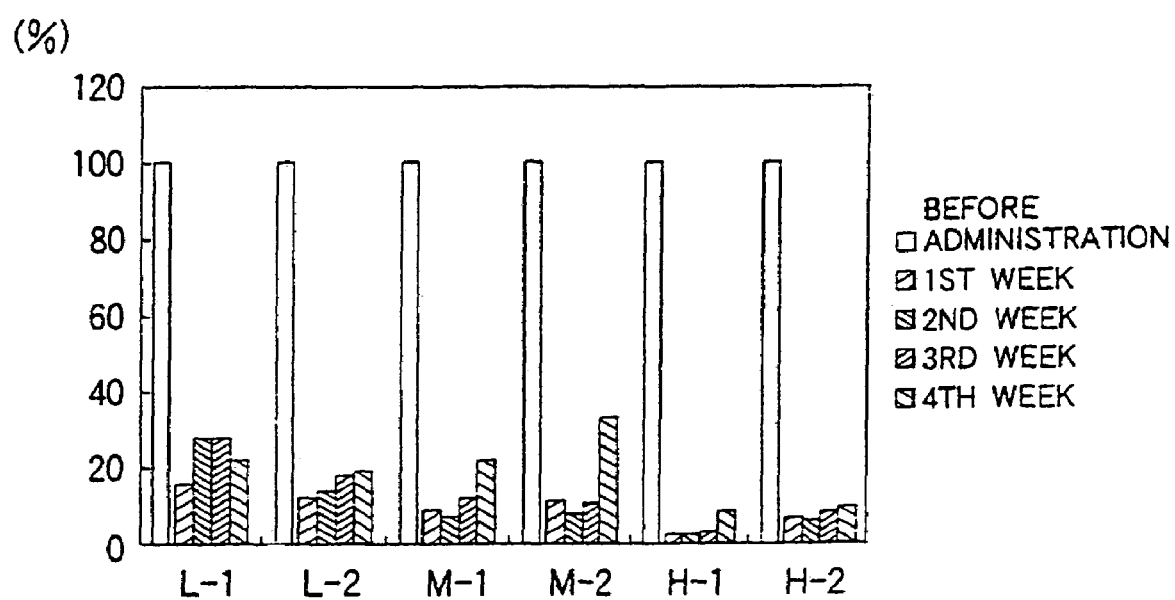
FIG. 13 is a drawing showing the changes in characteristics with time in a produced amount of IL-4 when an anti-CCR4 chimeric antibody KM2760 was administered to *Macaca fascicularis*.
Figure 14:
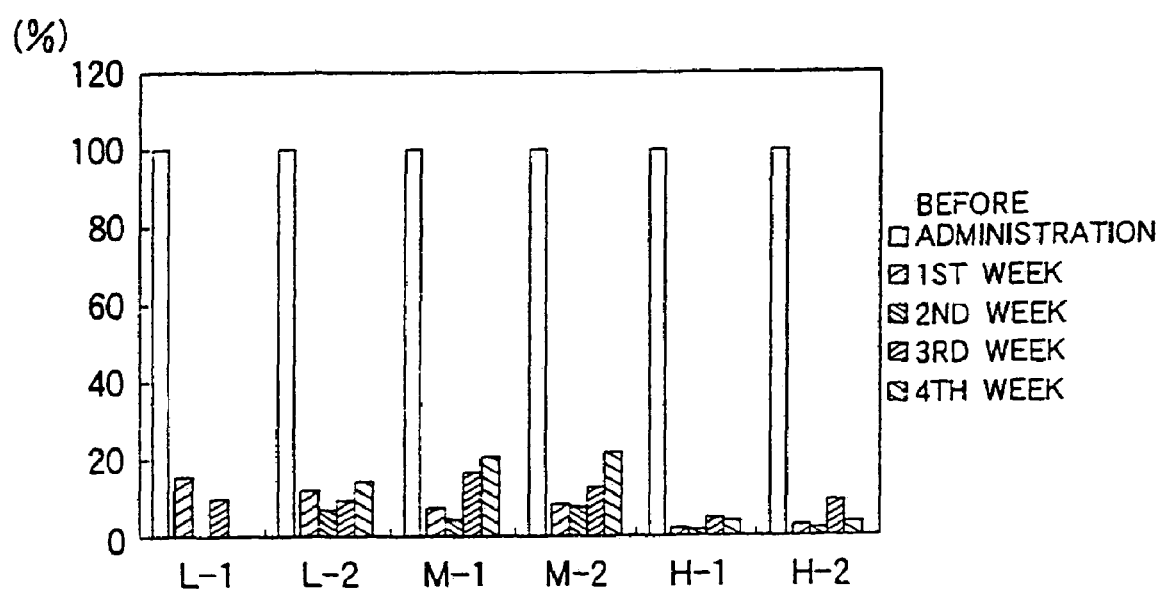
FIG. 14 is a drawing showing the changes with time in a produced amount of IL-13 when an anti-CCR4 chimeric antibody KM2760 was administered to *Macaca fascicularis*.
Figure 15:
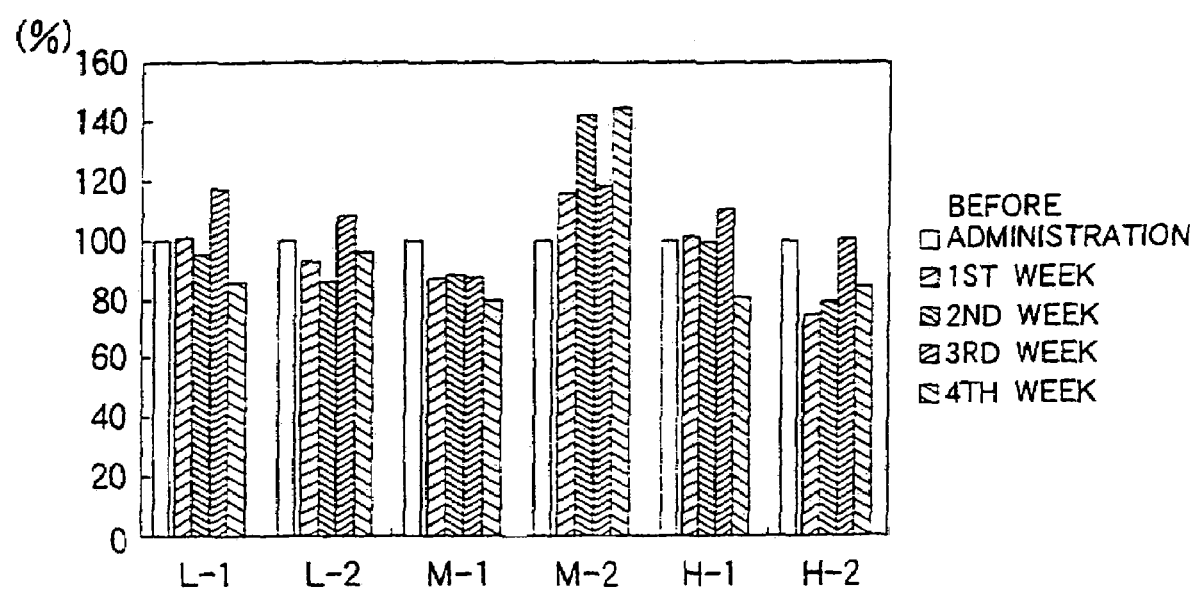
FIG. 15 is a drawing showing the changes in characteristics with time in a produced amount of IFN-γ when an anti-CCR4 chimeric antibody KM2760 was administered to *Macaca fascicularis*.

The dose (protein content) of the purified anti-CCR4 chimeric antibody KM2760 was 0.1 mg/kg, 1.0 mg/kg or 10 mg/kg, and the antibody was administered to 2 animals of four-year-old male *Macaca fascicularis* by single intravenous injection in each of the dose groups. Blood samples were collected from the femoral vein before the administration and on the 1st, 2nd, 3rd and 4th weeks after the administration. Heparin (Heparin Sodium Injection, 1,000 units/ml, manufactured by Shimizu Pharmaceutical) was used as the anticoagulant and added to 1 ml of blood to give a concentration of 25 units/ml. Using a flat bottom 24 well plate, peripheral blood of each individual was dispensed at 500 μl/well into 2 wells. A medium containing the stimulating agent (PMA final concentration 50 ng/ml, IONOMYCIN™ final concentration 1 μg/ml) was added to one well, and the medium containing no stimulating agent to another well, each at 500 μl/well, and the mixture was lightly stirred and cultured at 37° C., 5% $CO_2$ and 95% air for 24 hours. Also, the medium used was prepared by adding 0.5 ml of a penicillin-streptomycin solution (manufactured by GIBCO BRL) and 5.6 ml of immobilized fetal calf serum (manufactured by PAA Laboratories) to 100 ml of RPMI 1640 (GIBCO BRL). After completion of culturing, the culture broth containing blood cells was recovered from each well and centrifuged (6,700×g, 5 minutes, 4° C.) to obtain a supernatant. IL-4, IL-13 and IFN-γ contained in the resulting culture supernatant were determined using respective cytokine measuring kits (IL-4: OptEIA Human IL-4 Kit™, manufactured by PharMingen; IL-13: Cyto screen Human IL-13 Immunoassay Kit™ manufactured by BioSource International; IFN-γ: Cyto screen Human IFN-γ Immunoassay Kit™, manufactured by BioSource International). The produced amount of cytokine by each individual is a value calculated by subtracting the amount obtained by not adding the stimulating agent from the amount obtained by adding the stimulating agent (0.1 mg/kg group, individual Nos. L-1 and L-2; 1.0 mg/kg group, individual Nos. M-1 and M-2; 10 mg/kg group, individual Nos. H-1 and H-2). The results are shown in FIGS. 13 to 15. In these drawings, the value of each of IL-4, IL-13 and IFN-γ in each individual before the administration was used as 100%, and the produced amount after the administration was shown by percentage. Th2 cytokines, IL-4 (FIG. 13) and IL-13 (FIG. 14), significantly decreased on the 1st week after the administration in all administered groups, and the inhibition continued even on the 4th week after the administration. On the other hand, influence upon Th1 cytokine, IFN-γ (FIG. 15), was extremely small.

Based on these results, it was found that production of Th2 cytokine from peripheral blood mononuclear cells is inhibited at least for 4 weeks when the anti-CCR4 chimeric antibody KM2760 is administered to *Macaca fascicularis*. It was also shown that the anti-CCR4 chimeric antibody KM2760 reduced or depleted CCR4-expressing Th2 cells in peripheral blood in the body of *Macaca fascicularis*.

EXAMPLE 7

In vivo antitumor activity of anti-CCR4 chimeric antibody:

(1) Antitumor Effect of Anti-CCR4 Chimeric Antibody KM2760 on Syngenic Intraperitoneal Graft Model Antitumor effect of the anti-CCR4 chimeric antibody KM2760 on a mouse syngenic tumor model in which the hCCR4-high-expressing mouse-derived CCR4/EL-4 cells obtained in 2(4) of Example 2 was grafted into the abdominal cavity of mouse was measured. Eight-weeks-old male C57BL/6 mice (CLEA Japan) were used. The CCR4/EL-4 cells were suspended in PBS(−) (manufactured by Gibco BRL) to give a density of $1 \times 10^5$ cells/ml and grafted into the abdominal cavity of each of 10 C57BL/6 mice at a dose of 200 μl/animal. Four hours, three days, six days and ten days after the transplantation, 200 μl of KM2760 diluted to 2 mg/ml with a citrate buffer (an aqueous solution of 10 mmol/l citric acid and 150 mmol/l sodium chloride, adjusted to pH 6) was administered into the abdominal cavity of each of 5 animals among them. The remaining 5 animals were used as a negative control group to which the chimeric antibody was not administered. The number of days from the day of transplantation until mice of each group died due to proliferation of tumor cells accompanied by ascites is shown in Table 1. The average number of survival days was 16.4 day in the negative control group, whereas the average number of survival days in the KM2760-administered group was 26.2 day. Since 59.8% of survival period prolongation was found by the KM2760 administration, KM2760 has a life prolongation effect on the syngenic intraperitoneal graft model of CCR4 expressing leukemia cells.

TABLE 1

| | Days survived | Average value (day) | Survival ratio (%) |
|---|---|---|---|
| Negative control group | 14/14/16/18/20 | 16.4 | |
| KM2760-administered group | 21/22/23/29/36 | 26.2 | 59.8 |

(2) Antitumor Effect of Anti-CCR4 Chimeric Antibody KM2760 on Syngenic Subcutaneous Graft Model Antitumor effect of the anti-CCR4 chimeric antibody KM2760 on a mouse syngenic tumor model in which the hCCR4-high-expressing mouse-derived CCR4/EL-4 cells obtained in 2(4) of Example 2 was subcutaneously grafted into a mouse was measured. Eight-weeks-old male C57BL/6 mice (CLEA Japan) were used. The CCR4/EL-4 cells were suspended in PBS(−) (manufactured by Gibco BRL) to give a density of $1 \times 10^6$ cells/ml and grafted under the ventral side skin of each of 18 C57BL/6 mice at a dose of 50 μl/animal. Regarding 5 animals among them, 100 μl of KM2760 diluted to 2 mg/ml with a citrate buffer (an aqueous solution of 10 mmol/l citric acid and 150 mmol/l sodium chloride, adjusted to pH 6) was administered in the tail vein after 4 hours of the transplantation once a day for continuous 5 days. In this case, the dose per administration is 200 μg/animal. Regarding another 6 animals, 4 hours, 7 days and 14 days after the transplantation, 200 μl of KM2760 diluted to 2 mg/ml with the citrate buffer was administered in the tail vein. In this case, the dose per administration is 400 μg/animal. The remaining 7 animals were used as a negative control group to which the chimeric antibody was not administered. Six days after the transplantation, tumor diameter was periodically measured using slide calipers, and the antitumor effect was judged by the ratio of the average value of tumor volume in each administered group to the average value of tumor volume in each non-administered group. The tumor volume was calculated by the following equation:

Tumor volume=(breadth)$^2$×length×0.5

Figure 16:
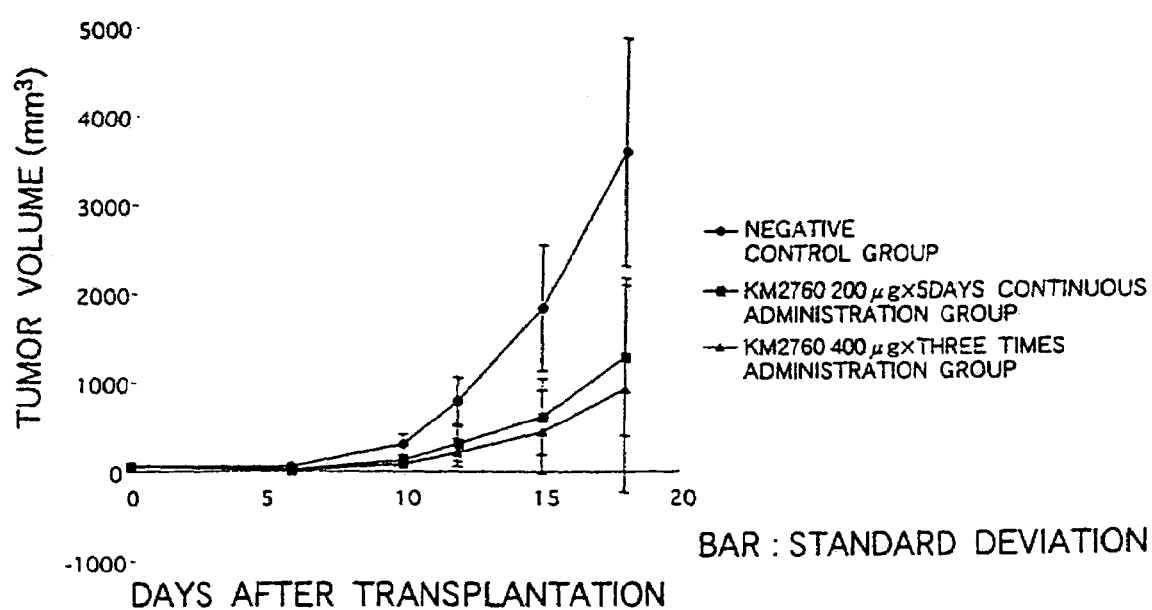
FIG. 16 is a drawing showing the changes in characteristics with time in the average value of tumor volumes when an anti-CCR4 chimeric antibody KM2760 was administered to mice to which hCCR4-high-expressing mouse-derived cells, CCR4/EL-4 cells, had been subcutaneously grafted.
Figure 17:
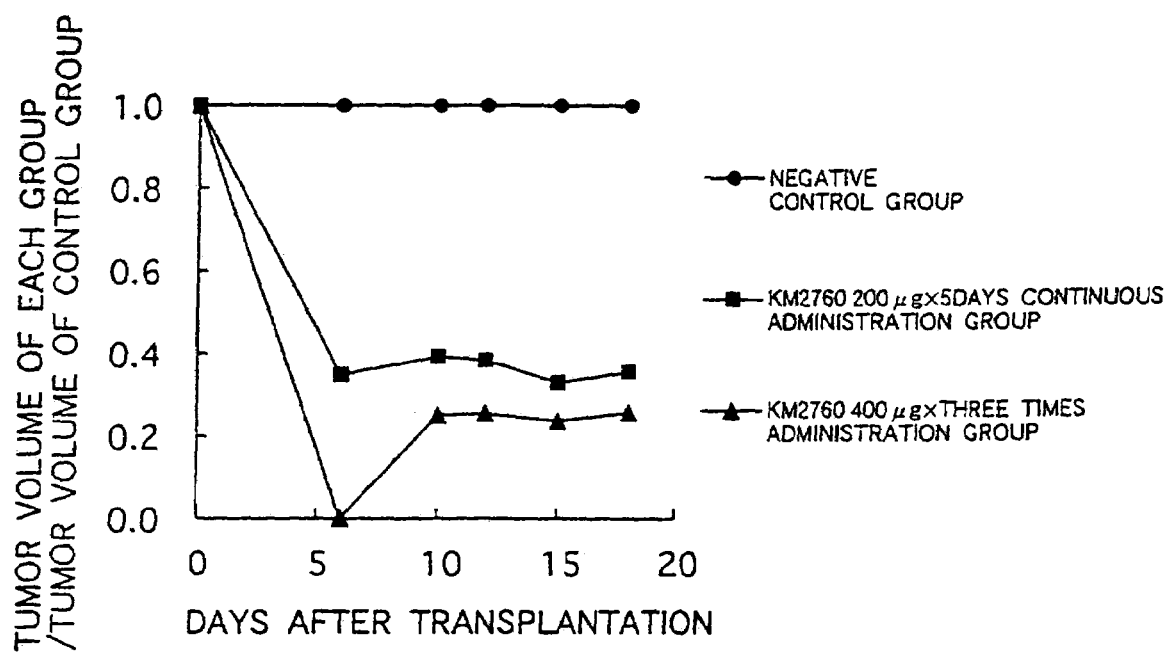
FIG. 17 is a drawing showing the ratio of the average value of tumor volumes in an administered group to the average value of tumor volumes in a non-administered group when an anti-CCR4 chimeric antibody KM2760 was administered to mice to which hCCR4-high-expressing mouse-derived cells, CCR4/EL-4 cells, had been subcutaneously grafted.

The average value of tumor volumes in each group is shown in Table 2 and FIG. 16, and results of the ratio of the average value of tumor volumes in each administered group to the average value of tumor volumes in the non-administered group are shown in Table 3 and FIG. 17. The ratio of the average value of tumor volumes in each KM2760-administered group to the average value of tumor volumes in the non-administered group on the 18th day after the transplantation was 0.356 in the group in which 200 μg was administered continuously for 5 days and 0.257 in the group in which 400 μg was administered three times, so that KM2760 showed a growth inhibition effect on the syngenic subcutaneous graft model of CCR4-positive leukemia cells by each of the administration schedules.

(3) Antitumor Effect of Anti-CCR4 Chimeric Antibody KM2760 on Xenograft Model

Antitumor effect of the anti-CCR4 chimeric antibody KM2760 on a mouse subcutaneous tumor xenograft model in which the hCCR4-expressing human T cell leukemia line CCRF-CEM cell (ATCC CCL-119) was subcutaneously grafted into nude mouse was measured. Eight-weeks-old male Balb/c nude mice (CLEA Japan) were used. The CCRF-CEM cells were suspended in RPMI 1640 medium (manufactured by Gibco BRL) to give a density of $1\times10^8$ cells/ml and grafted under the ventral side skin of each of 20 Balb/c nude mice at a dose of 200 μl/animal. Thereafter, they were divided into 4 groups of 5 animals per group, and 200 μl of KM2760 diluted to 2 mg/ml, 0.5 mg/ml or 0.2 mg/ml with the citrate buffer was administered to the three groups in the tail vein after 4 hours, 3 days and 6 days of the transplantation. In this case, the administered doses of KM2760 in respective groups are 400 μg/animal/day, 100 μg/animal/day and 40 μg/animal/day. The remaining one group was used as a negative control group by administering 200 μl of human immunoglobulin G (hereinafter referred to as "hIgG", manufactured by Welfide) diluted to 2 mg/ml with the citrate buffer in the tail vein (400 μg/animal/day). Four days after the transplantation, the tumor diameter was periodically measured using slide calipers, and the antitumor effect was judged by the tumor volume in each group. The tumor volume was calculated by the following equation:

Tumor volume=(breadth)$^2$×length×0.5

Figure 18:
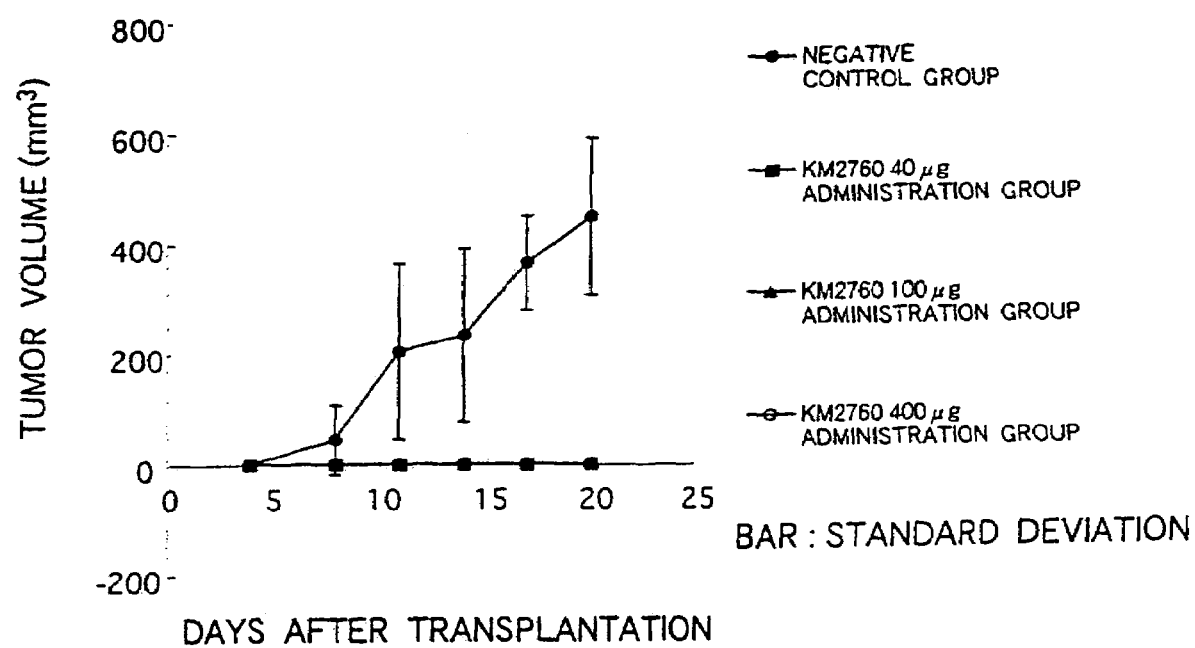
FIG. 18 is a drawing showing the changes in characteristics with time in the average value of tumor volumes when an anti-CCR4 chimeric antibody KM2760 was administered to mice to which CCR4-expressing human T cell leukemia line CCRF-CEM cells (ATCC CCL-119) had been subcutaneously grafted.

Changes with time in the average values of tumor volume in each group are shown in Table 4 and FIG. 18. Complete inhibition of tumor growth was observed in all of the KM2760-administered groups, so that KM2760 showed a growth inhibition effect on the subcutaneous tumor xenograft model of CCR4-positive leukemia cells.

TABLE 2

| Group constitution | Days after transplantation | | | | | |
| --- | --- | --- | --- | --- | --- | --- |
| | 0 | 6 | 10 | 12 | 15 | 18 |
| Negative control group | 50 ± 0 | 46 ± 28 | 294 ± 114 | 778 ± 263 | 1825 ± 708 | 3581 ± 1279 |
| KM2760 200 μg × 5 days continuous administration group | 50 ± 0 | 16 ± 20 | 115 ± 60 | 299 ± 194 | 601 ± 429 | 1274 ± 886 |
| KM2760 400 μg × three times administration group | 50 ± 0 | 0 ± 0 | 73 ± 49 | 198 ± 158 | 431 ± 467 | 920 ± 1163 |

Unit: mm$^3$ ± standard deviation

TABLE 3

| Group constitution | Days after transplantation | | | | | |
| --- | --- | --- | --- | --- | --- | --- |
| | 0 | 6 | 10 | 12 | 15 | 18 |
| Negative control group | 1.000 | 1.000 | 1.000 | 1.000 | 1.000 | 1.000 |
| KM2760 200 μg × 5 days continuous administration group | 1.000 | 0.348 | 0.393 | 0.384 | 0.330 | 0.356 |
| KM2760 400 μg × three times administration group | 1.000 | 0.000 | 0.250 | 0.254 | 0.236 | 0.257 |

TABLE 4

| Group constitution | Days after transplantation | | | | | |
|---|---|---|---|---|---|---|
| | 0 | 6 | 10 | 12 | 15 | 18 |
| Negative control group | 0 ± 0 | 44 ± 63 | 204 ± 159 | 233 ± 157 | 364 ± 86 | 448 ± 142 |
| KM2760 40 μg administered group | 0 ± 0 | 0 ± 0 | 0 ± 0 | 0 ± 0 | 0 ± 0 | 0 ± 0 |
| KM2760 100 μg administered group | 0 ± 0 | 0 ± 0 | 0 ± 0 | 0 ± 0 | 0 ± 0 | 0 ± 0 |
| KM2760 400 μg administered group | 0 ± 0 | 0 ± 0 | 0 ± 0 | 0 ± 0 | 0 ± 0 | 0 ± 0 |

Unit: mm$^3$ ± standard deviation

While the invention has been described in detail and with reference to specific embodiments thereof, it will be apparent to one of skill in the art that various changes and modifications can be made therein without departing from the spirit and scope thereof. All references cited herein are incorporated in their entirety.

---

What is claimed is:

1. A method for treating inflammation mediated by cytokines released from Th2 cells, comprising:
   administering, to a patient in need thereof, a therapeutically effective amount of a monoclonal antibody or antibody fragment thereof, wherein said antibody or antibody fragment specifically binds to the epitope recognized by antibody KM2160 produced by hybridoma FERM BP-10090, and wherein said antibody or antibody fragment exhibits antibody-dependent cell-mediated cytotoxic activity against a cell which expresses CCR4.

2. The method according to claim 1, wherein said antibody or antibody fragment specifically binds a CCR4-expressing cell.

3. The method according to claim 1, wherein said antibody or antibody fragment has an activity of inducing apoptosis of a Th2 cell.

4. The method according to claim 1, wherein said antibody or antibody fragment has an activity of depleting a Th2 cell.

5. The method according to claim 1, wherein said antibody or antibody fragment has an activity of inhibiting production of Th2 cytokines.

6. The method according to claim 5, wherein the Th2 cytokines are IL-4, IL-5 and IL-13.

7. The method according to claim 1, wherein said antibody is selected from the group consisting of a humanized antibody and a human antibody.

8. The method according to claim 7, wherein the humanized antibody is a human chimeric antibody or a human CDR-grafted antibody.

9. The method according to claim 1, wherein said antibody is a human IgG antibody.

10. The method according to claim 7, wherein the humanized antibody comprises:
    CDR1, CDR2 and CDR3 of an antibody H chain V region having the amino acid sequences of SEQ ID NOS:5, 6 and 7, respectively; and
    CDR1, CDR2 and CDR3 of an antibody L chain V region having the amino acid sequences of SEQ ID NOS:8, 9 and 10, respectively.

11. The method according to claim 8, wherein the human chimeric antibody comprises: an antibody H chain V region and antibody L chain V region of a monoclonal antibody which specifically binds CCR4; and an H chain C region and L chain C region of a human antibody.

12. The method according to claim 11, wherein the human chimeric antibody comprises:
    a CDR1, CDR2 and CDR3 of an H chain V region having the amino acid sequence of SEQ ID NOS:5, 6 and 7, respectively; and
    CDR1, CDR2 and CDR3 of an L chain V region having the amino acid sequences of SEQ ID NOS:8, 9 and 10, respectively.

13. The method according to claim 8, wherein the human chimeric antibody comprises:
    an H chain V region having amino acids of positions 20-138 in SEQ ID NO: 15; and
    an L chain V region having amino acids of positions 20-132 in SEQ ID NO: 16.

14. The method according to claim 8, wherein the human chimeric antibody is an antibody KM2760 produced by a transformant KM2760 (FERM BP-70541, and which H chain C region belongs to human IgG1 subclass.

15. The method according to claim 8, wherein the human CDR-grafted antibody comprises: CDRs of an antibody H chain V region and an antibody L chain V region of a monoclonal antibody which specifically binds CCR4; and C regions of an H chain and an L chain and a V region framework region of a human antibody.

16. The method according to claim 15, wherein the human CDR-grafted antibody comprises:
    CDR1, CDR2 and CDR3 of an H chain V region having the amino acid sequences of SEQ ID NOS:5, 6 and 7, respectively; and
    CDR1, CDR2 and CDR3 of an L chain V region having the amino acid sequences of SEQ ID NOS:8, 9 and 10, respectively.

17. The method according to claim 7, wherein the human antibody comprises an antibody H chain V region and an antibody L chain V region.

18. The method according to claim 17, wherein CDRs of the H chain V region and L chain V region of the human antibody comprise: amino acid sequences which are the same as amino acid sequences of CDRs of an H chain V region and an L chain V region, respectively, of a monoclonal antibody which specifically binds CCR4.

19. The method according to claim 18, wherein the human antibody comprises:
CDR1, CDR2 and CDR3 of an H chain V region having the amino acid sequences of SEQ ID NOS:5, 6 and 7, respectively, and
CDR1, CDR2 and CDR3 of an L chain V region having the amino acid sequences of SEQ ID NOS:8, 9 and 10, respectively.

20. The method according to claim 17, wherein the human antibody comprises amino acid sequences which are the same as amino acid sequences of an H chain V region and an L chain V region, respectively, of a monoclonal antibody which specifically binds CCR4.

21. The method according to claim 20, wherein the human antibody comprises:
an H chain V region having amino acids of positions 20-138 in SEQ ID NO: 15; and
an L chain V region having amino acids of positions 20-132 in SEQ ID NO: 16.

22. The method according to claim 17, wherein the human antibody is an antibody obtained from a human antibody phage library or a transgenic animal which produces a human antibody.

23. The method according to claim 1, wherein the antibody fragment is selected from Fab, Fab', F(ab')$_2$, a single chain antibody, or a disulfide stabilized V region fragment.

24. The method according to claim 23, wherein the antibody fragment comprises an antibody H chain V region and an antibody L chain V region of an antibody.

25. The method according to claim 24, wherein CDRs of the H chain V region and L chain V region of the antibody fragment comprise: amino acid sequences which are the same as amino acid sequences of CDRs of an H chain V region and an L chain V region, respectively, of a monoclonal antibody which specifically binds CCR4.

26. The method according to claim 25, wherein the antibody fragment comprises CDR1, CDR2 and CDR3 of the H chain V region having the amino acid sequences of SEQ ID NOS:5, 6 and 7, respectively; and CDR1, CDR2 and CDR3 of the L chain V region having the amino acid sequences of SEQ ID NOS:8, 9 and 10, respectively.

27. The method according to claim 24, wherein the H chain V region and L chain V region of the antibody fragment comprise amino acid sequences which are the same as amino acid sequences of an H chain V region and an L chain V region, respectively, of a monoclonal antibody which specifically binds CCR4.

28. The method according to claim 27, wherein the antibody fragment comprises:
an H chain V region having amino acids of positions 20-138 in SEQ ID NO:15; and
an L chain V region having amino acids of positions of 20-132 in SEQ ID NO: 16.

29. The method according to claim 1, wherein said antibody or antibody fragment is chemically or genetically conjugated to a radioisotope, a protein, an anticancer agent or an anti-inflammatory agent.

30. The method according to claim 15, wherein the human CDR-grafted antibody comprises:
CDR1, CDR2 and CDR3 of an H chain V region, and CDR1, CDR2 and CDR3 of an L chain V region having the amino acid sequences of SEQ ID NOS:5-10, respectively.

31. The method according to claim 18, wherein the human antibody comprises:
CDR1, CDR2 and CDR3 of an H chain V region, and CDR1, CDR2 and CDR3 of an L chain V region having the amino acid sequences of SEQ ID NOS:5-10, respectively.

32. The method according to claim 25, wherein the antibody fragment comprises:
CDR1, CDR2 and CDR3 of an H chain V region, and CDR1, CDR2 and CDR3 of an L chain V region having the amino acid sequences of SEQ ID NOS:5-10, respectively.

* * * * *